(12) United States Patent
Mittelman et al.

(10) Patent No.: US 8,183,373 B2
(45) Date of Patent: May 22, 2012

(54) SOLID STATE FORMS OF SITAGLIPTIN SALTS

(75) Inventors: Ariel Mittelman, Elad (IL); Nada Kosutic Hulita, Zagreb (HR); Nurit Perlman, Kfar Saba (IL); Motti Erlich, Petach-Tikva (IL); Luna Ben-Sahel Katzav, Kiryat Ono (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 13/077,119

(22) Filed: Mar. 31, 2011

(65) Prior Publication Data

US 2011/0245498 A1    Oct. 6, 2011

Related U.S. Application Data

(60) Provisional application No. 61/319,439, filed on Mar. 31, 2010, provisional application No. 61/328,783, filed on Apr. 28, 2010, provisional application No. 61/330,647, filed on May 3, 2010, provisional application No. 61/331,988, filed on May 6, 2010, provisional application No. 61/350,145, filed on Jun. 1, 2010, provisional application No. 61/362,356, filed on Jul. 8, 2010, provisional application No. 61/365,491, filed on Jul. 19, 2010, provisional application No. 61/370,909, filed on Aug. 5, 2010, provisional application No. 61/429,271, filed on Jan. 3, 2011, provisional application No. 61/441,355, filed on Feb. 10, 2011.

(51) Int. Cl.
*C07D 487/04* (2006.01)
(52) U.S. Cl. ....................................................... 544/350
(58) Field of Classification Search .................... 544/350
See application file for complete search history.

(56) References Cited

U.S. PATENT DOCUMENTS

| | | | |
|---|---|---|---|
| 6,699,871 B2 | 3/2004 | Edmondson et al. | |
| 7,125,873 B2 | 10/2006 | Edmondson et al. | |
| 7,326,708 B2 | 2/2008 | Cypes et al. | |
| 7,612,072 B2 | 11/2009 | Ferlita et al. | |
| 2008/0280913 A1 | 11/2008 | Harbeson | |
| 2010/0249140 A1* | 9/2010 | Pilarski et al. | 514/249 |

FOREIGN PATENT DOCUMENTS

| | | |
|---|---|---|
| WO | WO 03/082817 | 10/2003 |
| WO | WO 2004/085378 | 10/2004 |
| WO | WO 2004/085661 | 10/2004 |
| WO | WO 2004/087650 | 10/2004 |
| WO | WO 2005/003135 | 1/2005 |
| WO | WO 2005/020920 | 3/2005 |
| WO | WO 2005/030127 | 4/2005 |
| WO | WO 2005/072530 | 8/2005 |
| WO | WO 2006/033848 | 3/2006 |
| WO | WO 2006/081151 | 8/2006 |
| WO | WO 2006/119260 | 11/2006 |
| WO | WO 2007/035198 | 3/2007 |
| WO | WO 2009/045507 | 4/2009 |
| WO | WO 2009/070314 | 6/2009 |
| WO | WO 2009/085990 | 7/2009 |
| WO | WO 2010/000469 | 1/2010 |
| WO | WO 2010/012781 | 2/2010 |
| WO | WO2010092090 | * 8/2010 |
| WO | WO 2010/117738 | 10/2010 |

OTHER PUBLICATIONS

IP.com publication 160623D, 2011.
Caira, Mino R., "Crystalline Polymorphism of Organic Compounds", Topics in Current Chemistry, 1998, vol. 198, pp. 163-208.

* cited by examiner

*Primary Examiner* — Andrew D Kosar
*Assistant Examiner* — Karen Cheng
(74) *Attorney, Agent, or Firm* — Kenyon & Kenyon LLP

(57) ABSTRACT

Crystalline forms of Sitagliptin salts, processes for preparing crystalline forms of Sitagliptin salts, and pharmaceutical compositions of Sitagliptin salts are provided.

9 Claims, 42 Drawing Sheets

SOLID STATE FORMS OF SITAGLIPTIN SALTS

RELATED APPLICATIONS

This application claims the benefit under 35 U.S.C. §119 (e) of U.S. Provisional Application Nos. 61/319,439, filed Mar. 31, 2010; 61/328,783, filed Apr. 28, 2010; 61/330,647 filed May 3, 2010; 61/331,988 filed May 6, 2010; 61/350,145 filed Jun. 1, 2010; 61/362,356 filed Jul. 8, 2010; 61/365,491 filed Jul. 19, 2010; 61/370,909 filed Aug. 5, 2010; 61/429,271 filed Jan. 3, 2011; 61/441,355 filed Feb. 10, 2011, each of which is incorporated herein by reference in its entirety.

FIELD OF THE INVENTION

The invention relates to crystalline forms of Sitagliptin salts, processes for preparing the crystalline forms, and pharmaceutical compositions thereof.

BACKGROUND OF THE INVENTION

Sitagliptin, (3R)-3-amino-1-[9-(trifluoromethyl)-1,4,7,8-tetrazabicyclo-[4.3.0]nona-6,8-dien-4-yl]-4-(2,4,5-trifluorophenyl)butan-1-one, has the following chemical structure:

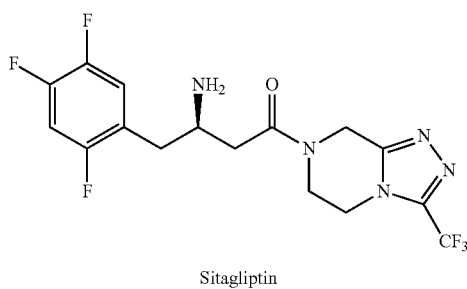

Sitagliptin

Sitagliptin phosphate is a glucagon-like peptide 1 metabolism modulator, hypoglycemic agent, and dipeptidyl peptidase IV inhibitor. Sitagliptin is currently marketed in the United States as its phosphate salt in its monohydrate form under the trade name JANUVIA™. JANUVIA™ is indicated to improve glycemic control in patients with type 2 diabetes mellitus.

The following PCT Publications describe the synthesis of Sitagliptin via stereoselective reduction: WO 2004/087650, WO 2004/085661, and WO 2004/085378.

Several crystalline forms of Sitagliptin phosphate are described in the literature. WO 2005/020920 describes crystalline forms I, II, III, and an ethanol solvate; WO 2005/030127 describes crystalline form IV; WO 2005/003135 describes a monohydrate form; and WO 2006/033848 described the amorphous form.

Crystalline forms of certain Sitagliptin salts are described in PCT publications nos. WO 2009/085990, WO 2010/000469, and WO 2010/012781.

Polymorphism, the occurrence of different crystal forms, is a property of some molecules and molecular complexes. A single molecule may give rise to a variety of polymorphs having distinct crystal structures and physical properties like melting point, thermal behaviors (e.g., measured by thermogravimetric analysis—"TGA", or differential scanning calorimetry—"DSC"), x-ray diffraction pattern, infrared absorption fingerprint, and solid state NMR spectrum. One or more of these techniques may be used to distinguish different polymorphic forms of a compound.

Discovering new polymorphic forms and solvates of a pharmaceutical product can provide materials having desirable processing properties, such as ease of handling, ease of processing, storage stability, and ease of purification or as desirable intermediate crystal forms that facilitate conversion to other polymorphic forms. New polymorphic forms and solvates of a pharmaceutically useful compound or salts thereof can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, or improved shelf-life. For at least these reasons, there is a need for additional polymorphs of Sitagliptin (or a salt thereof).

The present invention discloses solid state forms of Sitagliptin salts.

SUMMARY OF THE INVENTION

The present invention provides crystalline forms of Sitagliptin salts and processes for preparing them. The present invention also provides the use of these salts for the preparation of Sitagliptin phosphate.

The invention further provides pharmaceutical compositions comprising the below described crystalline forms of Sitagliptin salts. This pharmaceutical composition may additionally comprise at least one pharmaceutically acceptable excipient.

The invention further provides the use of the solid state forms described below for the manufacture of a medicament for the treatment of type 2 diabetes mellitus.

DETAILED DESCRIPTION OF THE INVENTION

Figure 1:
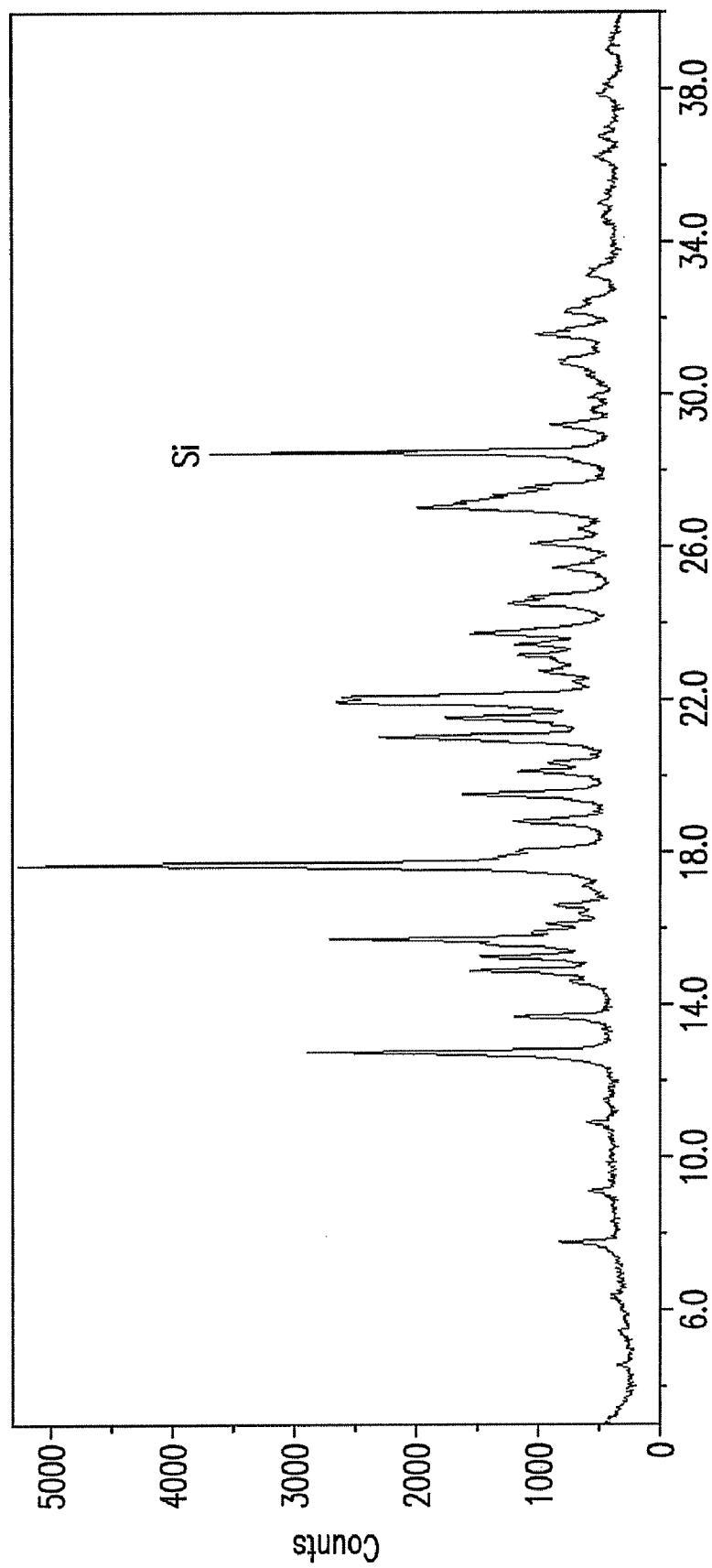
FIG. 1 provides a powder XRD pattern of crystalline Form S9 of Sitagliptin sulfate.

The present application relates to new polymorphic forms of Sitagliptin salts.

A crystal form (or polymorph) may be referred to herein as substantially free of any other crystalline (or polymorphic) forms. As used herein in this context, the expression "substantially free" will be understood to mean that the crystalline form contains 20% or less, 10% or less, 5% or less, 2% or less, or 1% or less of any other form of the subject compound as measured, for example, by XRPD. Thus, polymorphs of Sitagliptin salts described herein as substantially free of any other polymorphic forms would be understood to contain greater than 80% (w/w), greater than 90% (w/w), greater than 95% (w/w), greater than 98% (w/w), or greater than 99% (w/w) of the subject polymorphic form of Sitagliptin. Accordingly, in some embodiments of the invention, the described polymorphs of Sitagliptin salts may contain from 1% to 20% (w/w), from 5% to 20% (w/w), or from 5% to 10% (w/w) of one or more other crystal forms of Sitagliptin.

A crystal form may be referred to herein as being characterized by graphical data "as shown in" a Figure. Such data include, for example, powder X-ray diffractograms and solid state NMR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form, and confirm whether the two sets of graphical data are characterizing the same crystal form or two different crystal forms.

As used herein, the abbreviation "STG" refers to Sitagliptin.

As used herein, the abbreviation "XRD" is used to refer to "X-ray diffraction," for example when stating that a crystalline form is characterized by a "powder XRD pattern with peaks at . . . . " The abbreviation "XRD" is also used as an abbreviation for the expression "X-ray diffractogram," for example, when stating that a crystalline form is characterized by "a powder XRD as shown in Figure A."

As used herein, the term "room temperature" refers to a temperature of about 20° C. to about 35° C., or about 25° C. to about 35° C., or about 25° C. to about 30° C., for example, about 25° C.

As used herein, the term "overnight" refers to a time interval from about 14 hours to about 24 hours, or about 14 hours to about 20 hours, for example, about 16 hours.

As used herein, the expression "chemical shift difference" refers to the difference in chemical shifts between a reference signal and another signal in the same NMR spectrum. These chemical shift differences serve to provide an additional analytical measurement for a substance, for example a crystalline form of Sitagliptin salt according to the present invention, which will compensate for a phenomenon that may occur in NMR spectroscopy wherein a shift in the solid-state NMR "fingerprint" is observed. Such a shift in the NMR peaks may occur, for example as a result of variations in the instrumentation, the temperature, or the calibration method used in the NMR analysis. This shift in the solid-state NMR "fingerprint", having chemical shift resonances at a certain positions, is such that even though the individual chemical shifts of signals have moved, all the peaks in the spectrum are moved by the same amount, such that the difference between chemical shifts of each signal and another selected signal is retained. This chemical shift difference provides data that may thus be used as a reliable characterization of the material being analyzed even when there is a shift in the overall solid-state NMR "fingerprint".

In the present patent application the chemical shift differences were calculated by subtracting the chemical shift value of the signal exhibiting the lowest chemical shift (reference signal) in the solid state $^{13}$C NMR spectrum in the range of 100 to 190 ppm from chemical shift value of another (observed) signal in the same $^{13}$CNMR spectrum in the range of 100 to 190 ppm.

Unless indicated otherwise, the solid state forms of the present invention can be dried. Drying may be carried out, for example, at elevated temperature under reduced pressure. The crystalline form can be dried at a temperature from about 40° C. to about 60° C., or about 40° C. to about 50° C., for example, about 40° C. The drying can be carried out under reduced pressure (i.e., less than 1 atmosphere, for example, about 10 mbar to about 100 mbar, or about 10 mbar to about 25 mbar). The drying can take place over a period of about 8 hours to about 36 hours, or about 10 hours to about 24 hours, for example, about 16 hours. Drying can be carried out overnight.

As used herein, Sitagliptin sulfate Form S2 refers to a crystalline Sitagliptin sulfate characterized by a powder XRD pattern with peaks at 9.3°, 9.7°, 15.2°, 15.6°, and 25.4°±0.2° 2θ. Sitagliptin sulfate Form S2 can be obtained, for example, by forming a solution of Sitagliptin base in acetonitrile; combining the solution with sulfuric acid to form a precipitate; and isolating the obtained precipitate; wherein, the sulfuric acid is used at a mol ratio of about 1:0.5 of Sitagliptin base to sulfuric acid, e.g., as indicated in PCT application No. PCT/US10/29098.

Figure 41:
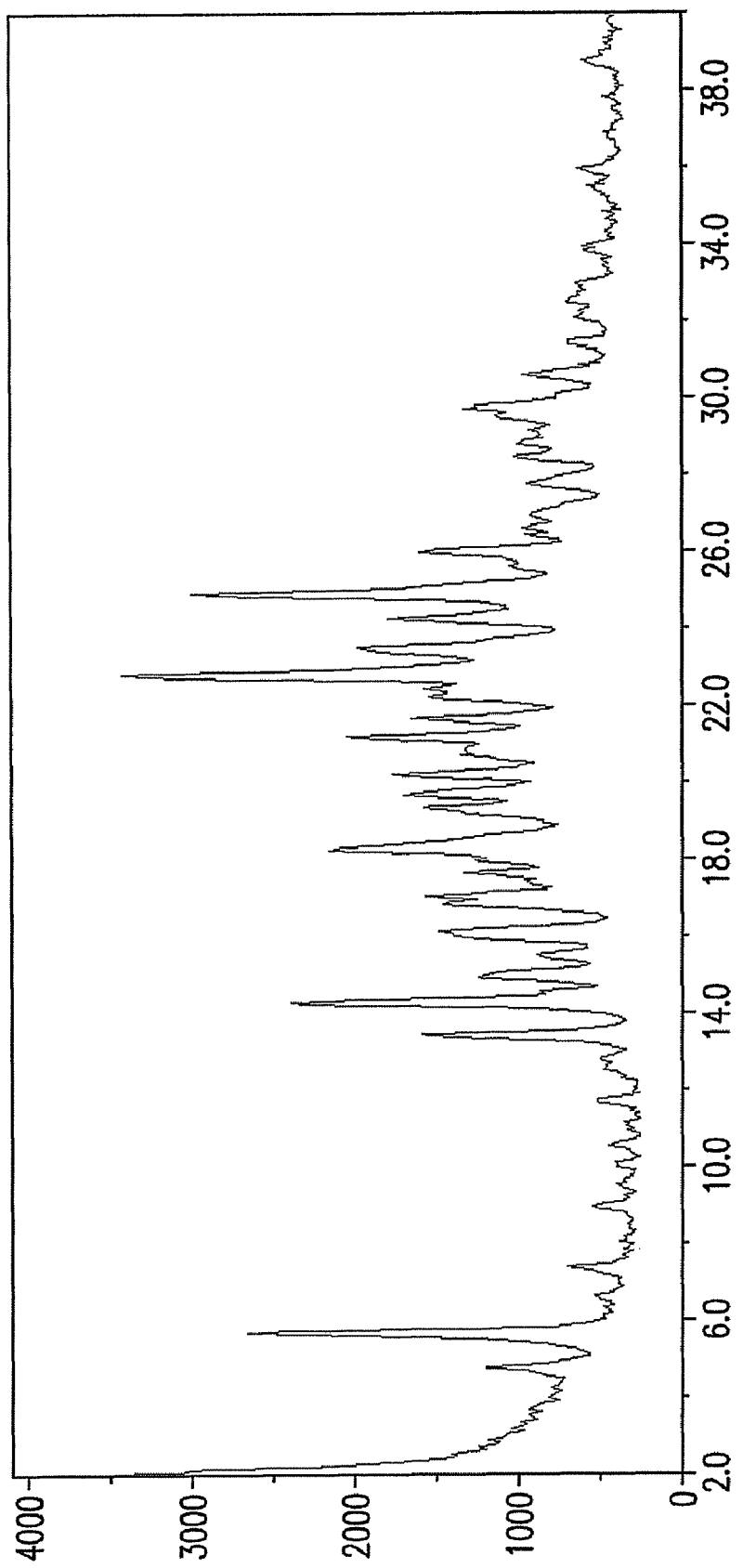
FIG. 41 provides a powder XRD pattern of crystalline Form S3 of Sitagliptin sulfate.

As used herein, Sitagliptin sulfate Form S3 refers to a crystalline Sitagliptin sulfate characterized as shown in FIG. 41. It can be also characterized by a powder XRD pattern with peaks at 7.4°, 16.1°, 18.3°, and 24.9°±0.2° 2θ. Sitagliptin sulfate Form S3 can be obtained, for example, by forming a solution of Sitagliptin base in ethyl acetate; combining the solution with sulfuric acid to form a precipitate; and isolating the thus-obtained precipitate; wherein, the sulfuric acid is used at a mol ratio of about 1:0.5 of Sitagliptin base to sulfuric acid, e.g., as indicated in PCT application No. PCT/US10/29098.

Figure 37:
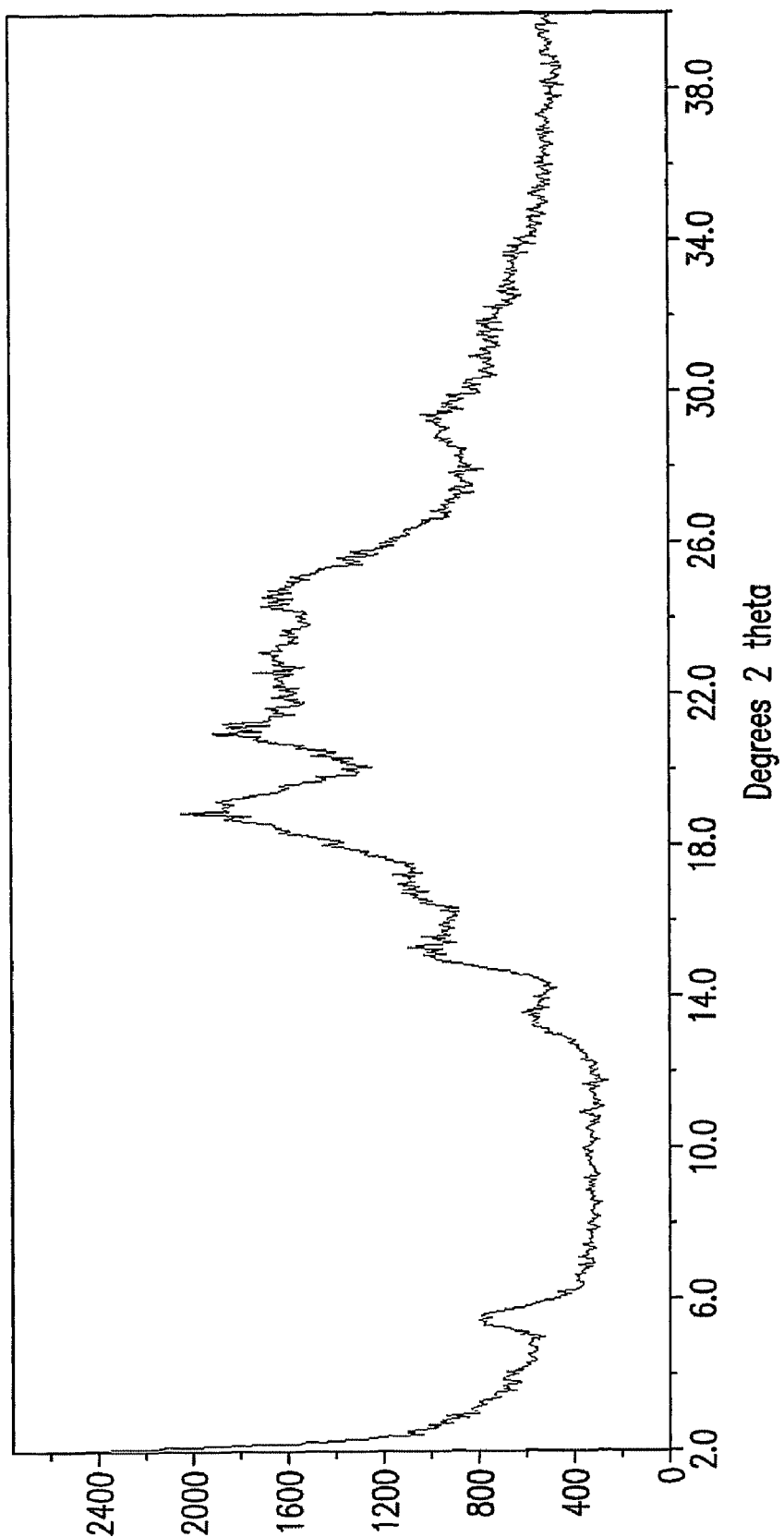
FIG. 37 provides a powder XRD pattern of crystalline Form S6 of Sitagliptin sulfate.

As used herein, Sitagliptin sulfate Form S6 refers to a crystalline Sitagliptin sulfate characterized by a powder XRD pattern as shown in FIG. 37. It can be also characterized by a powder XRD pattern with peaks at 5.5°, 13.4°, 15.1°, 19.0°, and 21.1°±0.3° 2θ. Sitagliptin sulfate Form S6 can be obtained, for example, by forming a solution of Sitagliptin base in ethyl acetate; combining the solution with sulfuric acid to form a precipitate; and isolating the obtained precipitate; wherein the sulfuric acid is used at a mol ratio of about 1:0.5 of Sitagliptin base to sulfuric acid. The obtained precipitate can be further dried, e.g., as indicated in PCT application No. PCT/US10/29098.

Figure 38:
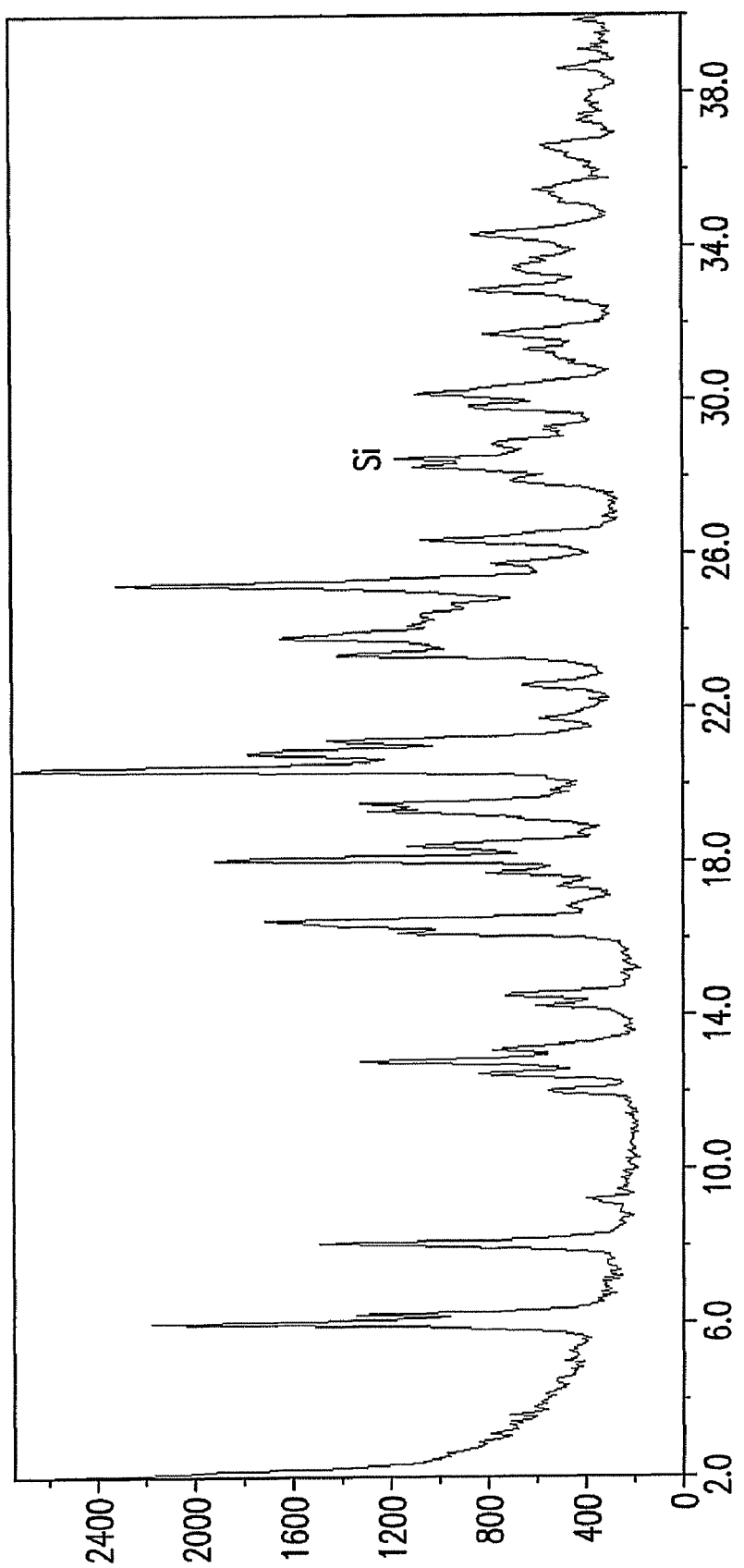
FIG. 38 provides a powder XRD pattern of crystalline Form I1 of Sitagliptin L-malate.

As used herein, Sitagliptin L-malate Form I1 refers to a crystalline Sitagliptin L-malate characterized by a powder XRD pattern as shown in FIG. 38. It can be also characterized by a powder XRD pattern with peaks at 6.0°, 8.0°, 12.8°, 18.0°, and 20.4°±0.2° 2θ. Form I1 can be prepared, for example, by forming a solution of Sitagliptin base in acetonitrile; combining the solution with L-malic acid to form a precipitate; and isolating the obtained precipitate; wherein the sulfuric acid is used at a mol ratio of about 1:1 of Sitagliptin base to L-malic acid. The obtained precipitate can be further dried, e.g., as indicated in PCT application No. PCT/US10/29098.

Figure 39:
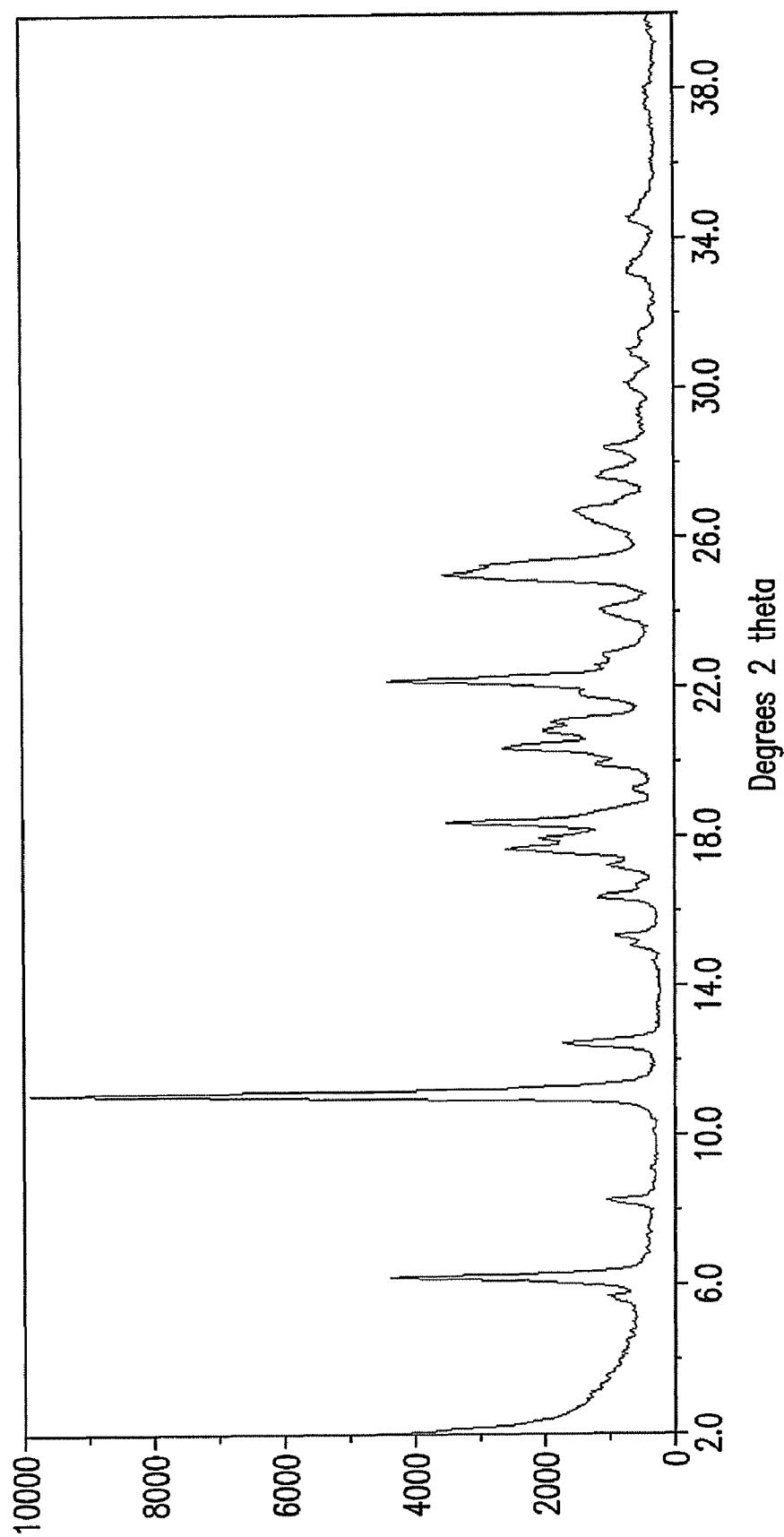
FIG. 39 provides a powder XRD pattern of crystalline Form E1 of Sitagliptin acetate.

As used herein, Form E1 refers to a crystalline form of Sitagliptin acetate, characterized by a powder XRD pattern as shown in FIG. 39. It can be also characterized by a powder XRD pattern with peaks at 6.2°, 11.1°, 12.5°, 17.7°, and 18.4°±0.2° 2θ. Form E1 can be prepared, for example, by a process comprising forming a solution or a slurry of Sitagliptin base in ethyl acetate; combining the solution or the slurry with acetic acid to form a precipitate; and isolating the obtained precipitate, e.g., as indicated in PCT application No. PCT/US10/29098.

Figure 40:
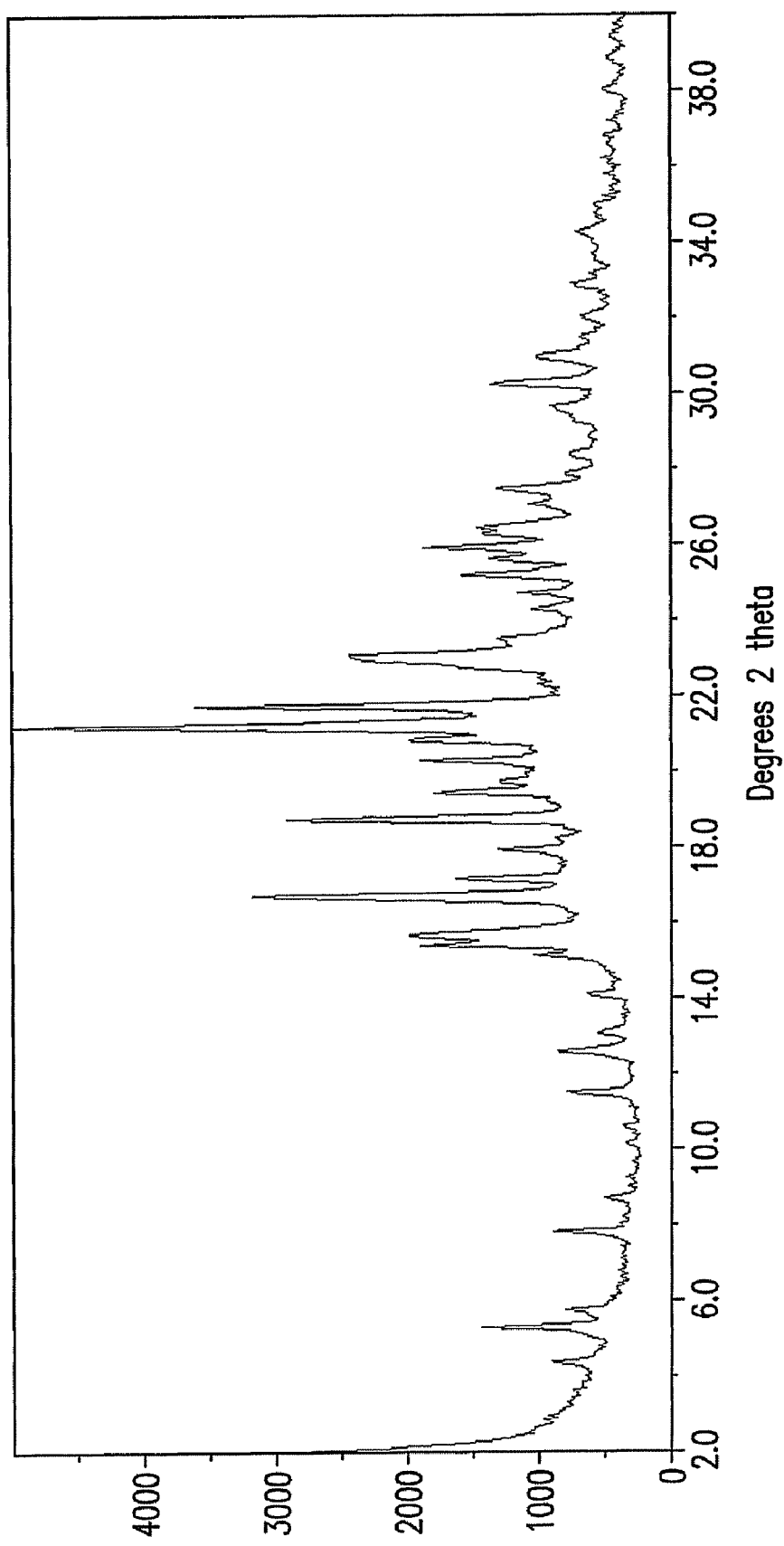
FIG. 40 provides a powder XRD pattern of crystalline Form S7 of Sitagliptin sulfate.

As used herein, Form S7 refers to a crystalline form of Sitagliptin sulfate characterized by a powder XRD pattern as shown in FIG. 40. It can be also characterized by a powder XRD pattern with peaks at 5.2°, 15.6°, 16.6°, 18.7°, and 21.1°±0.2° 2θ, as indicated in PCT application No. PCT/US10/29098.

As used herein, Sitagliptin L-malate Form II refers to a crystalline form of Sitagliptin L-malate as described in PCT Publication No. WO20100000469.

The present invention provides novel crystalline forms of Sitagliptin sulfate. The provided new forms of Sitagliptin sulfate preferably have advantageous properties selected from at least one of: high crystallinity, solubility, dissolution rate, morphology, thermal and mechanical stability to polymorphic conversion and/or to dehydration, storage stability, low content of residual solvent, a lower degree of hygroscopicity, flowability, and advantageous processing and handling characteristics such as compressibility, and bulk density.

In particular, the crystalline forms of Sitagliptin sulfate disclosed herein are advantageous in combining the two properties: high crystallinity and high water solubility.

In one embodiment, the present invention provides a crystalline Sitagliptin sulfate, designated Form S9. Form S9 can be characterized by a powder XRD pattern with peaks at 12.7°, 15.7°, 17.7°, 21.0°, and 21.9°±0.2° 2θ; or by a powder XRD pattern as shown in FIG. 1; or by combinations thereof.

Alternatively, Sitagliptin sulfate Form S9 can be characterized by a powder XRD pattern with peaks at 7.8°, 12.7°, 13.7°, 14.9°, 15.3°, 15.7°, 17.7°, 19.5°, 21.0°, and 21.9°±0.2° 2θ. In addition, Sitagliptin sulfate Form S9 can be characterized by any combination of the above data.

Figure 7:
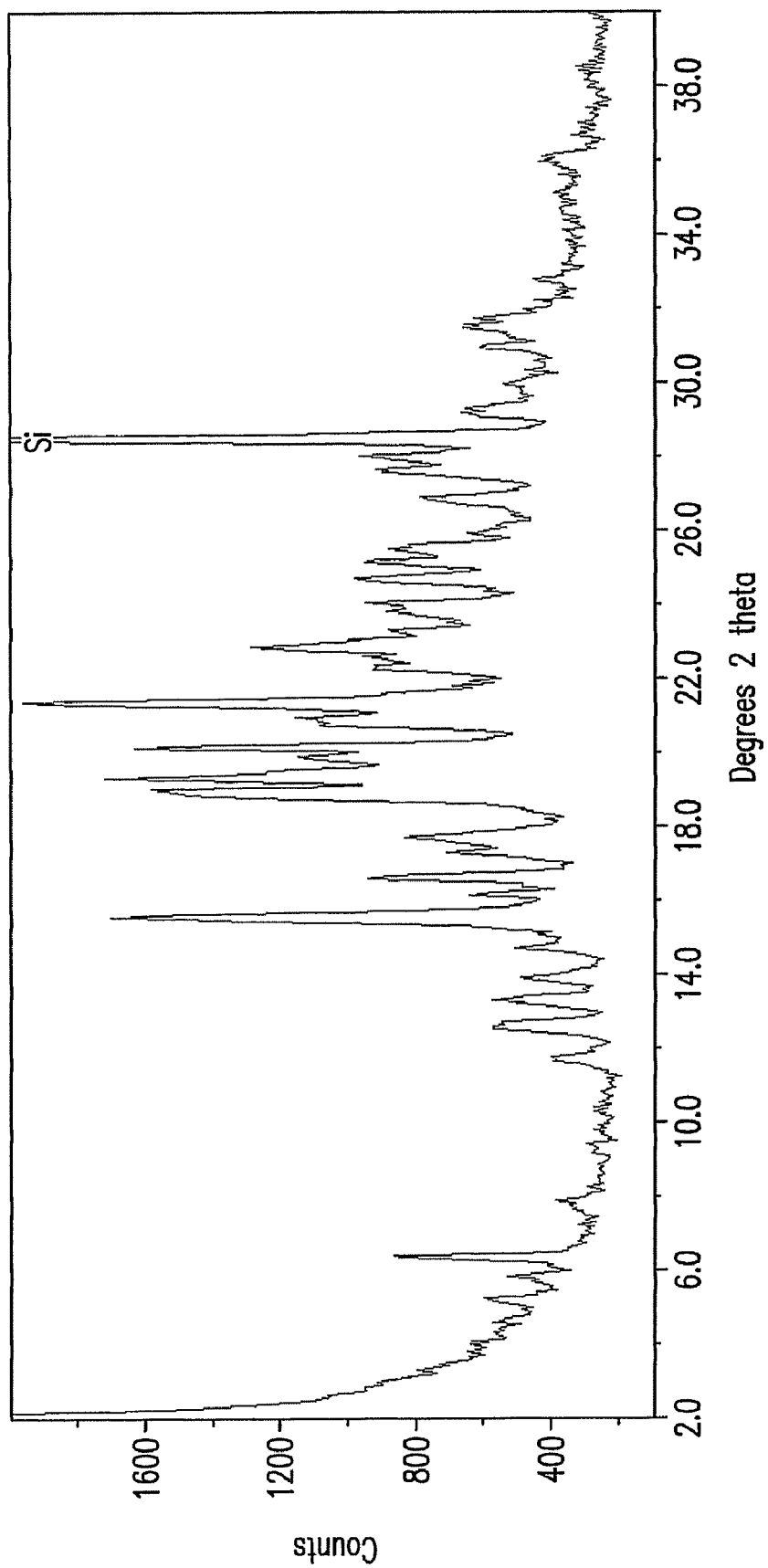
FIG. 7 provides a powder XRD pattern of crystalline Form S10 of Sitagliptin sulfate.

In another embodiment, the invention provides a crystalline Sitagliptin sulfate, designated as Form S10. Form S10 can be characterized by a powder XRD pattern with peaks at 6.4°, 15.5°, 16.6°, 19.3°, and 21.3°±0.2° 2θ; or by a powder XRD as shown in FIG. 7; or by combinations thereof.

Alternatively, Form S10 can be characterized by a powder XRD pattern with peaks at 6.4°, 15.5°, 16.6°, 18.9°, 19.3°, 19.8°, 20.1°, 20.8°, 21.3°, and 22.8°±0.2° 2θ. In addition, Sitagliptin sulfate Form S10 can be characterized by any combination of the above data.

Figure 8:
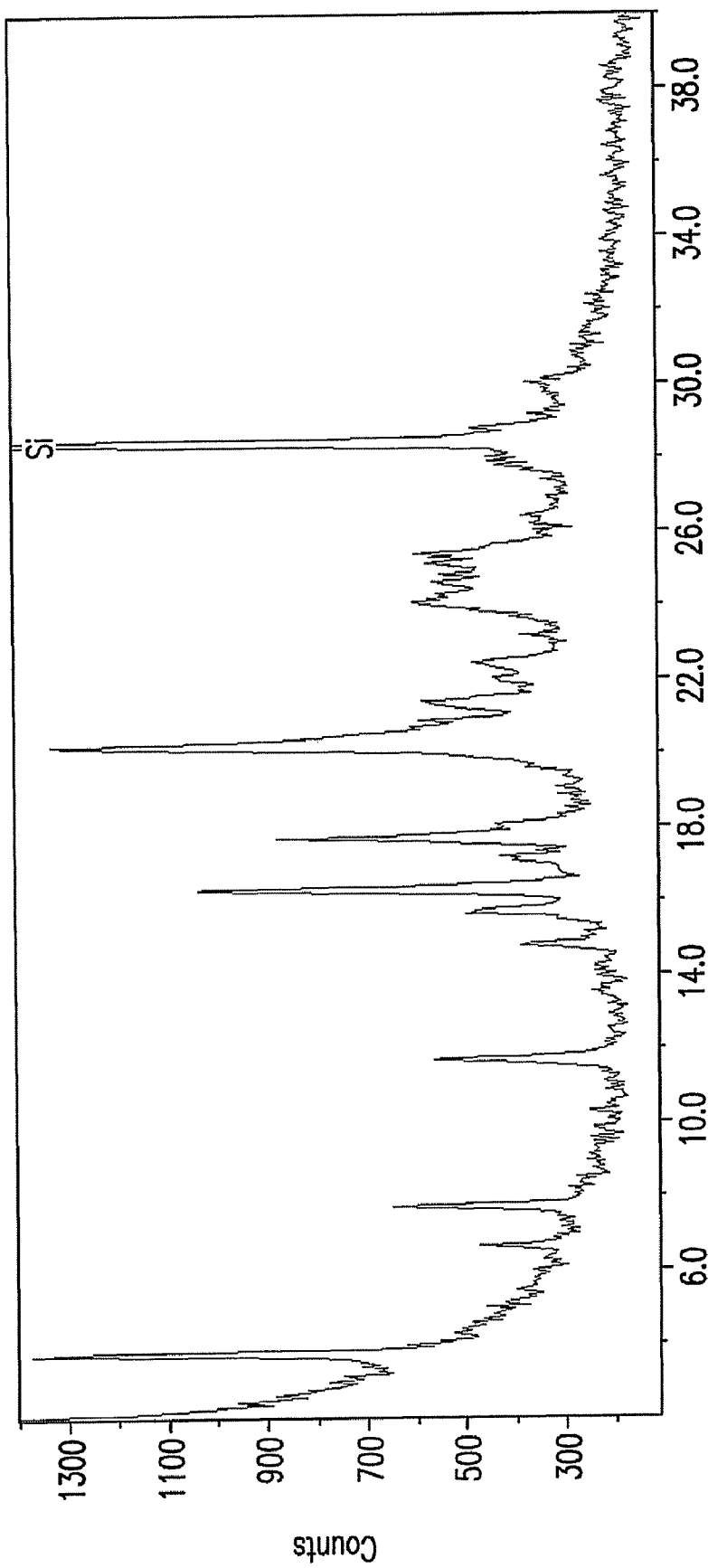
FIG. 8 provides a powder XRD pattern of crystalline Form S11 of Sitagliptin sulfate.

In another embodiment, the invention provides a crystalline Sitagliptin sulfate, designated as Form S11. Form S11 can be characterized by a powder XRD pattern with peaks at 3.9°, 7.9°, 11.8°, 16.4°, and 17.8°±0.2° 2θ; or by a powder XRD as shown in FIG. 8; or by combinations thereof.

Alternatively, Form S11 can be characterized by a powder XRD pattern with peaks at 3.9°, 7.9°, 11.8°, 15.8°, 16.4°, 17.8°, 20.3°, 21.4°, and 24.1°±0.2° 2θ. In addition, Sitagliptin sulfate Form S11 can be characterized by any combination of the above data.

Figure 9:
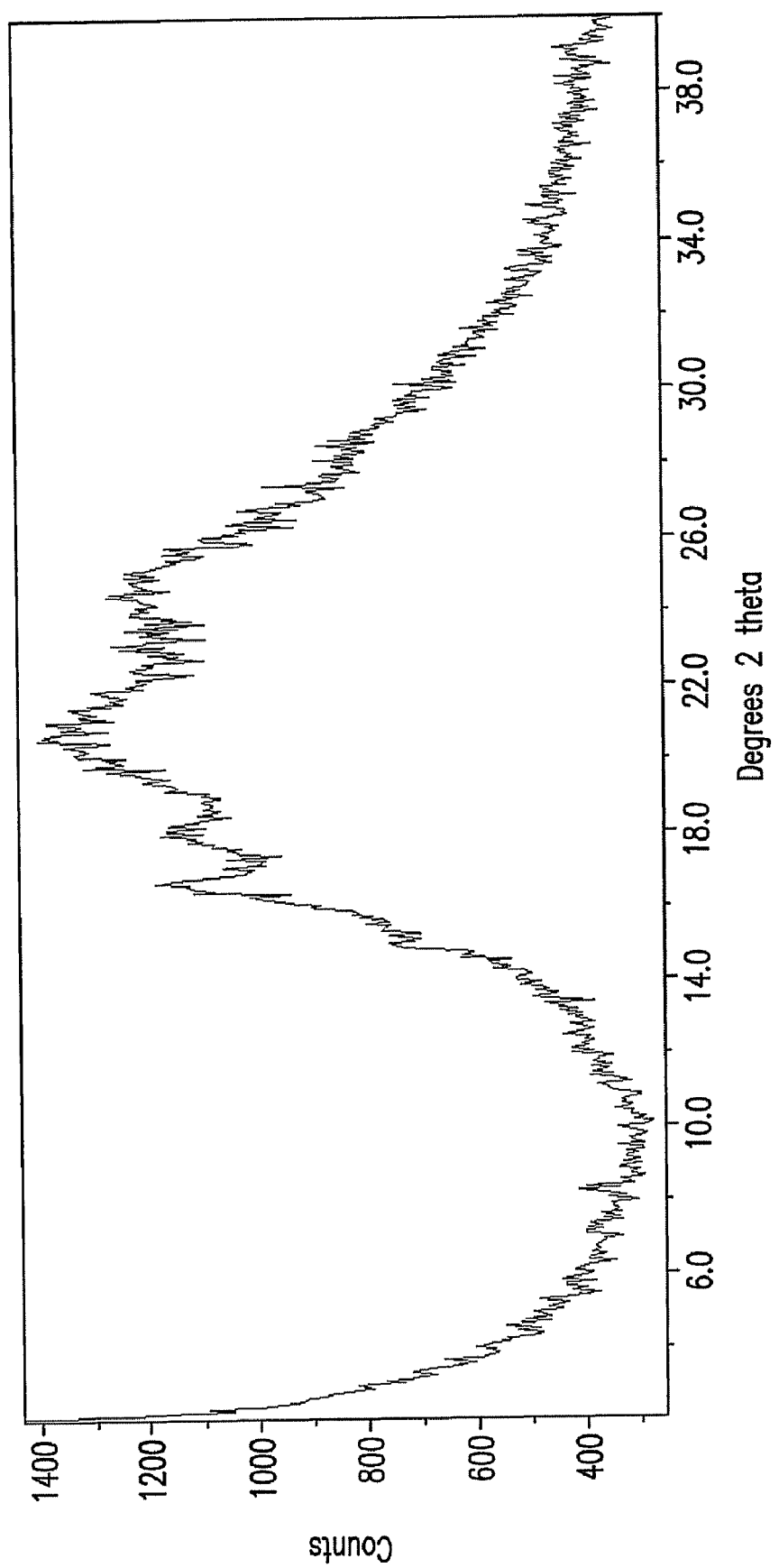
FIG. 9 provides a powder XRD pattern of crystalline Form S12 of Sitagliptin sulfate.
Figure 10:
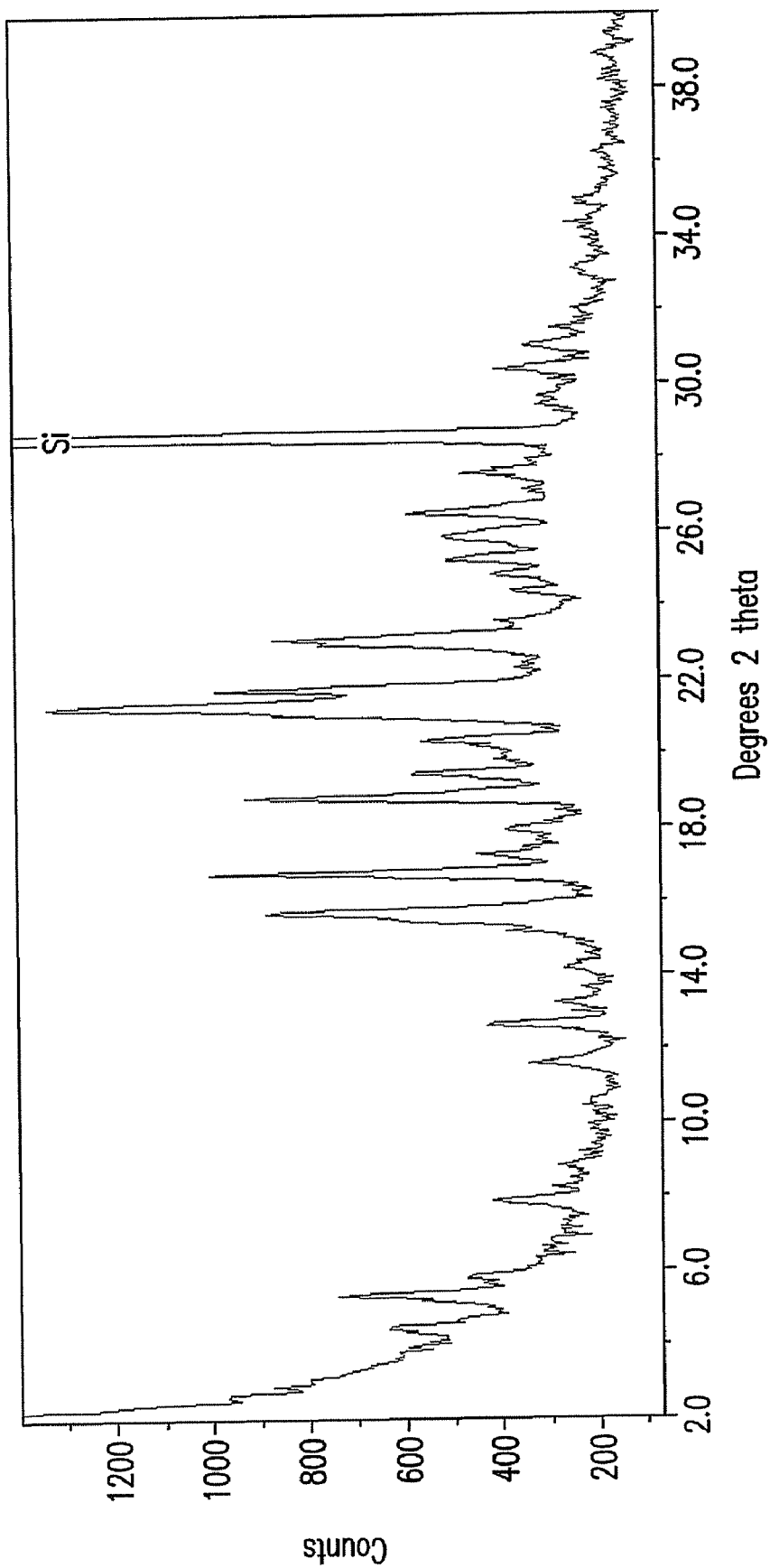
FIG. 10 provides a powder XRD pattern of crystalline Form S7 of Sitagliptin sulfate.

In another embodiment, the invention provides a crystalline Sitagliptin sulfate, designated as Form S12. Form S12 can be characterized by a powder XRD as shown in FIG. 9.

Figure 18:
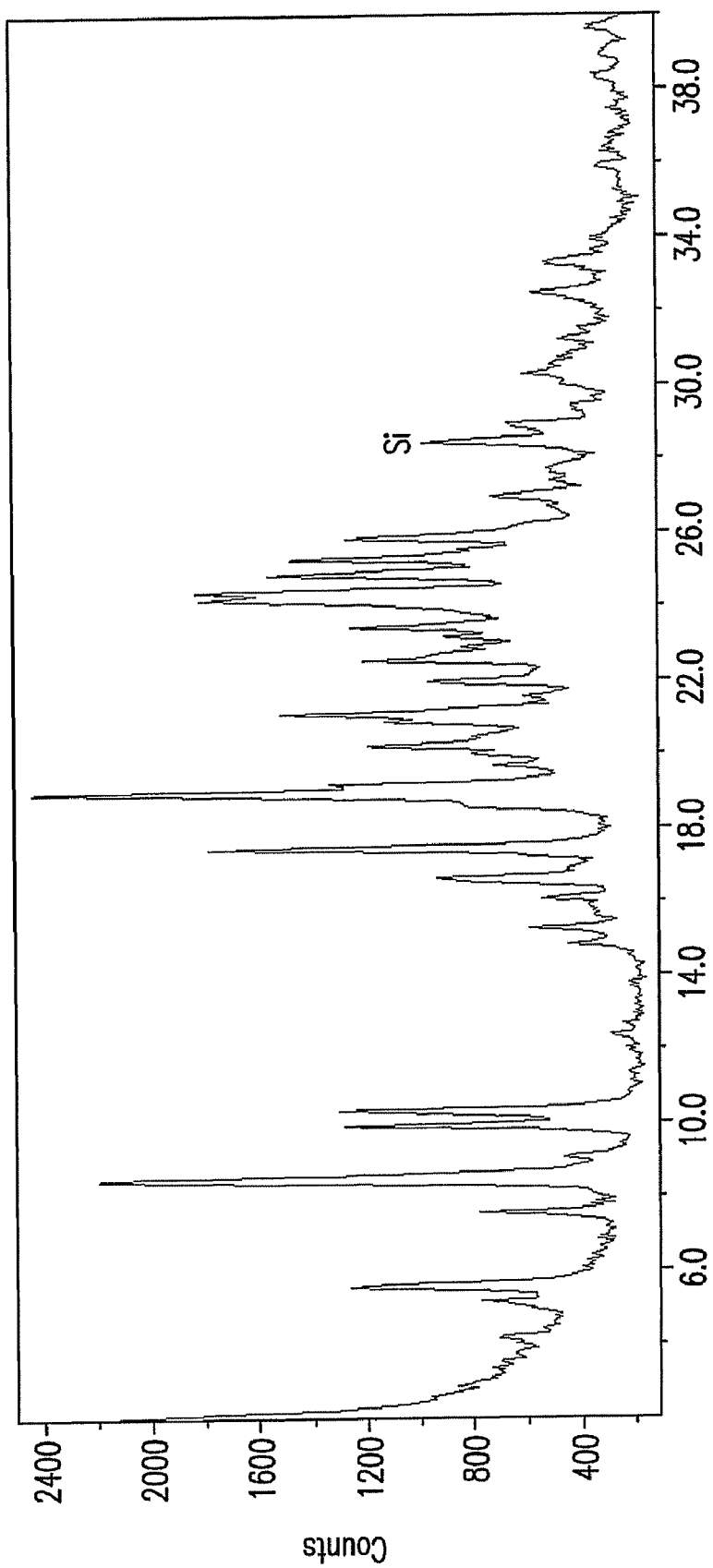
FIG. 18 provides a powder XRD pattern of crystalline Form S13 of Sitagliptin sulfate.

In another embodiment, the invention provides a crystalline Sitagliptin sulfate, designated as Form S13. Form S13 is methanol solvate. Form S13 can be characterized by a powder XRD pattern with peaks at 5.6°, 8.5°, 16.6°, 17.4°, and 19.0°±0.2° 2θ; or by a powder XRD as shown in FIG. 18; or by combinations thereof.

Alternatively, Form S13 can be characterized by a powder XRD pattern with peaks at 5.6°, 8.5°, 9.9°, 10.3°, 16.6°, 17.4°, 18.6°, 19.0°, 21.0°, and 25.2°±0.2° 2θ. In addition, Sitagliptin sulfate Form S13 can be characterized by any combination of the above data.

Alternatively, Form S13 can be characterized by a powder XRD pattern with peaks at 5.6°, 8.5°, 9.9°, 10.3°, 16.6°, 17.4°, 19.0°, 21.0°, and 25.2°±0.2° 2θ. In addition, Sitagliptin sulfate Form S13 can be characterized by any combination of the above data.

Figure 11:
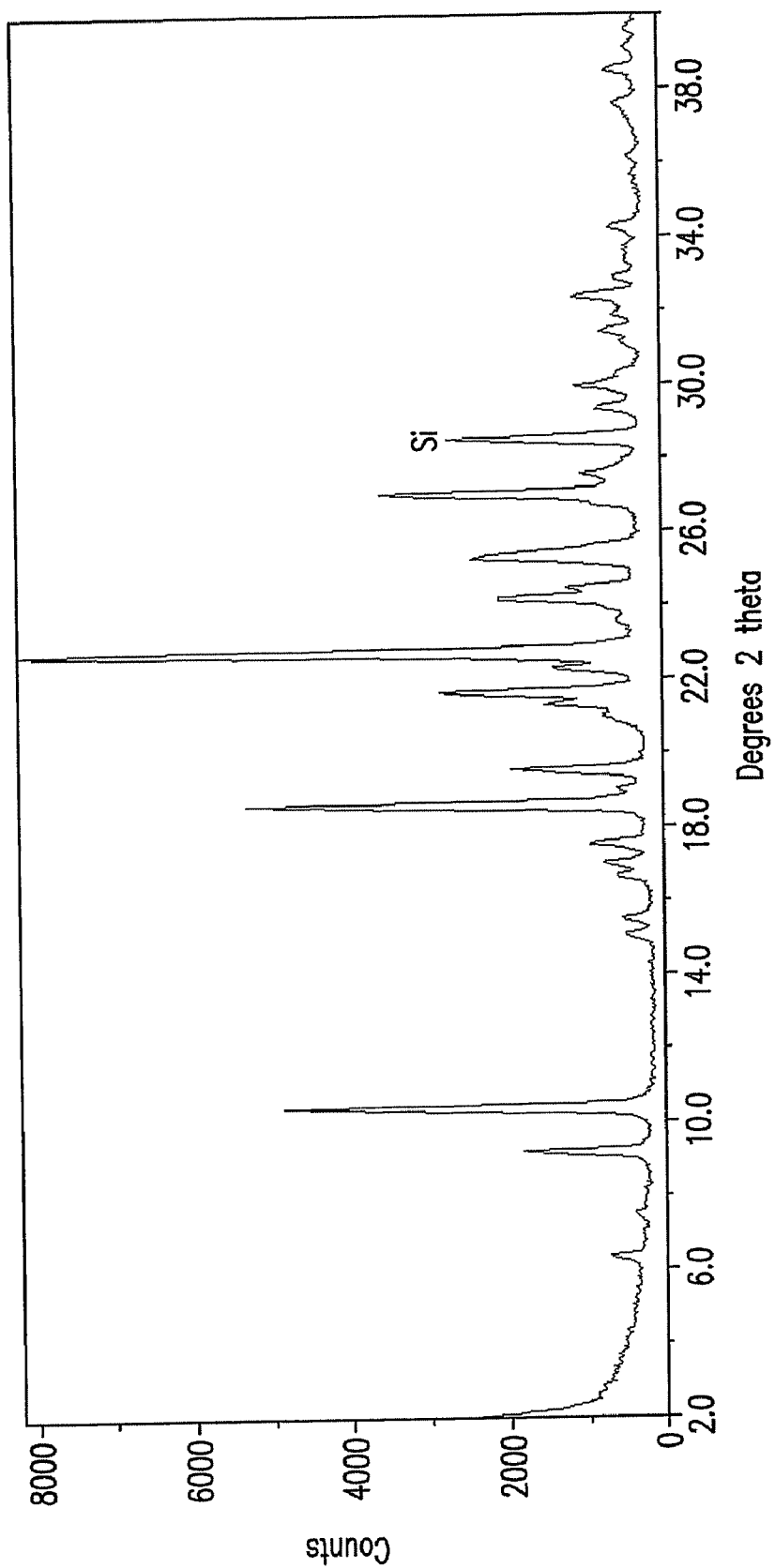
FIG. 11 provides a powder XRD pattern of crystalline Form S14 of Sitagliptin sulfate.
Figure 12:
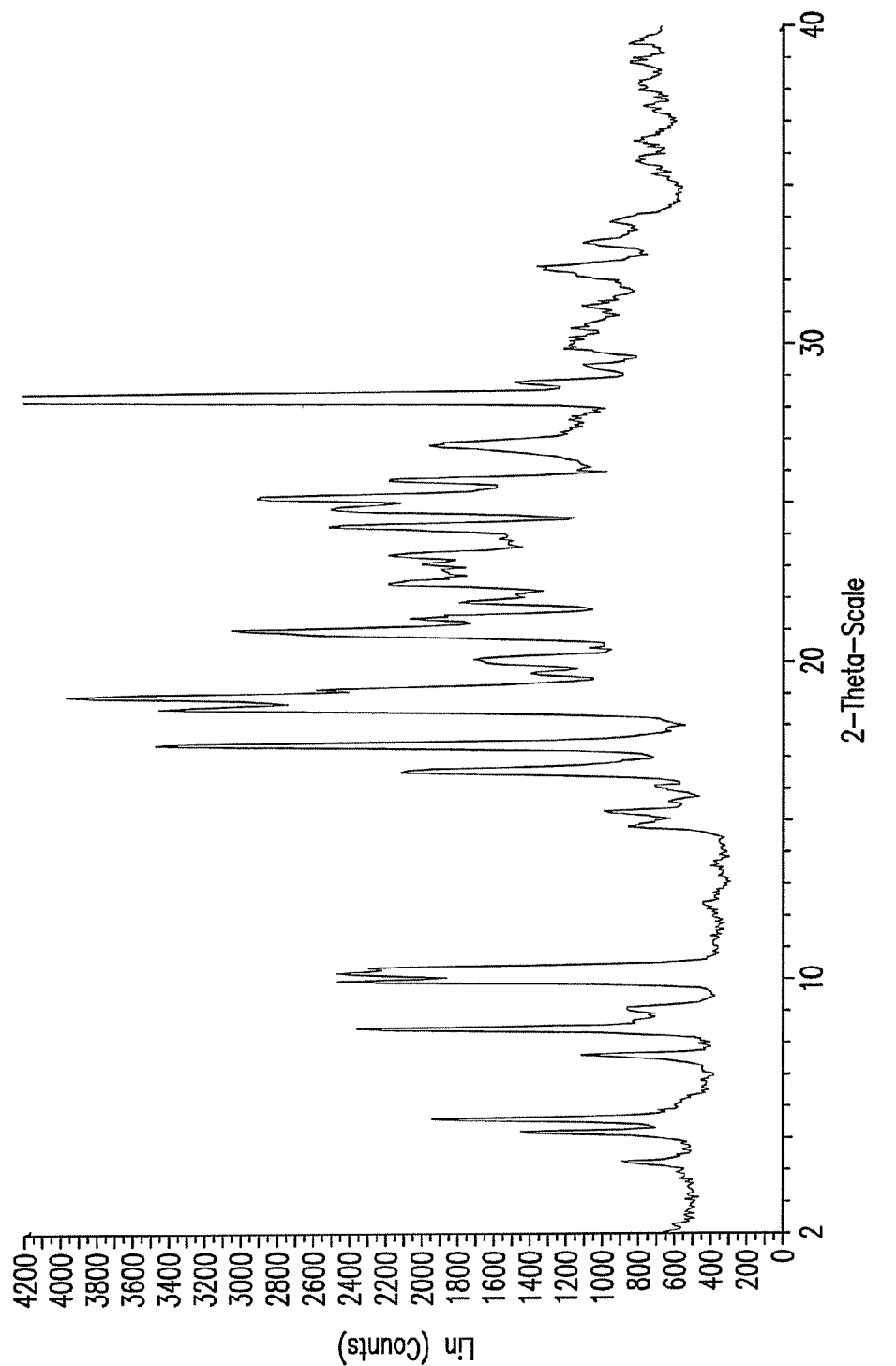
FIG. 12 provides a powder XRD pattern of crystalline Form S13 of Sitagliptin sulfate.
Figure 23:
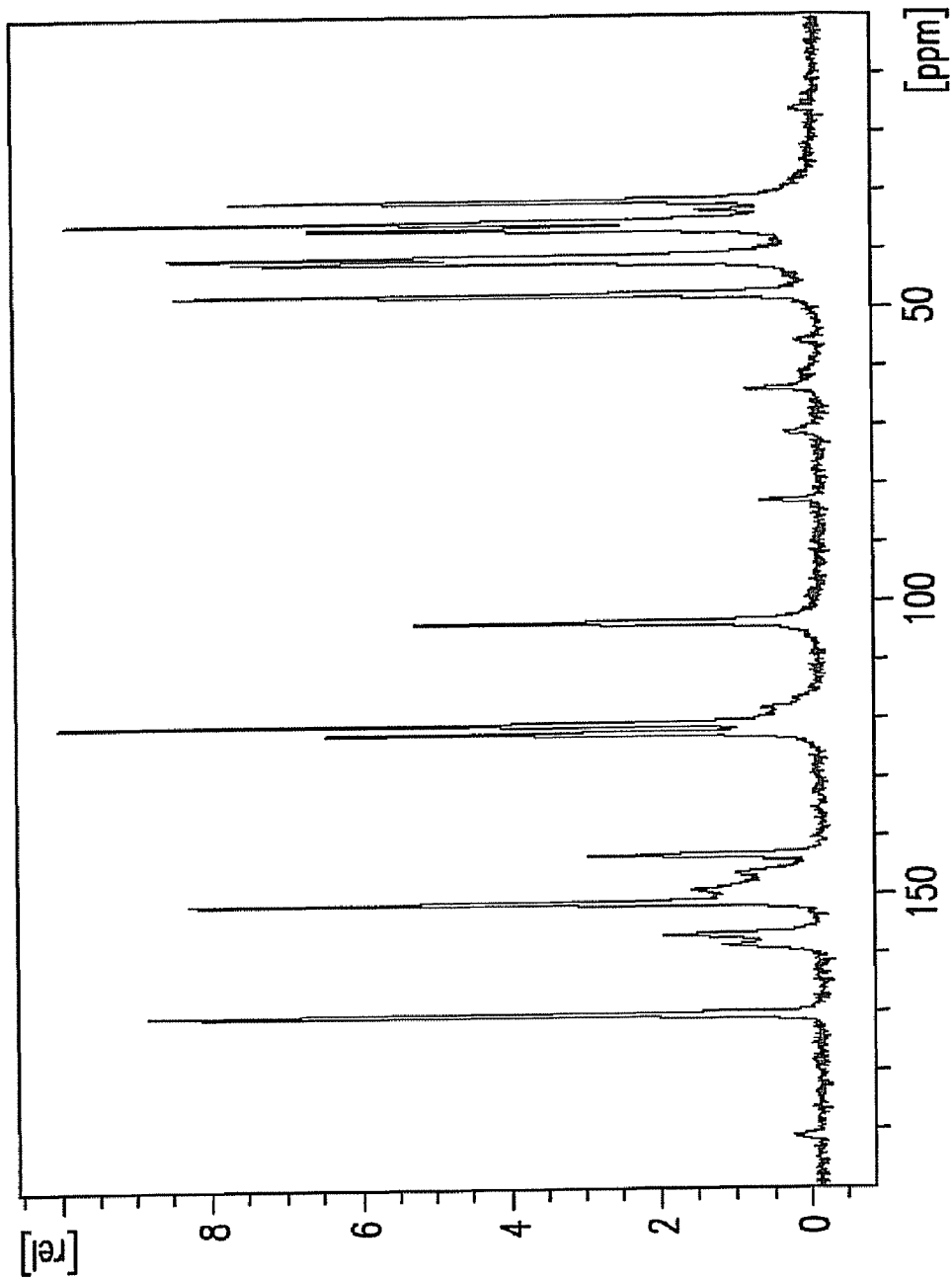
FIG. 23 provides a solid state $^{13}C$ NMR spectrum of crystalline Form S14 of Sitagliptin sulfate in the 0-200 ppm range.
Figure 24:
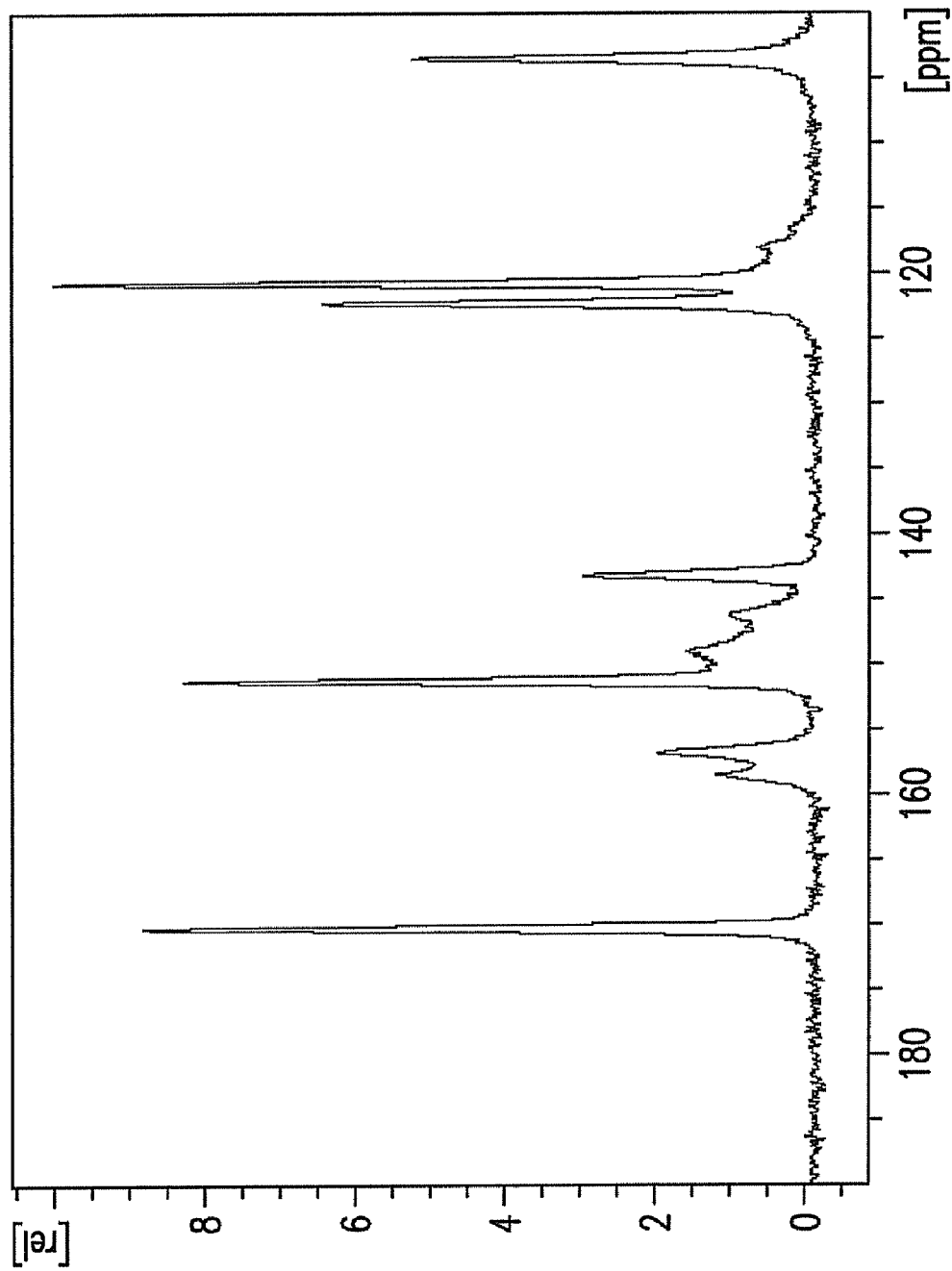
FIG. 24 provides a solid state $^{13}C$ NMR spectrum of crystalline Form S14 of Sitagliptin sulfate in the 100-190 ppm range.

In another embodiment, the invention provides a crystalline Sitagliptin sulfate, designated as Form S14. Form S14 is a hydrate, for example, a monohydrate. Form S14 can be characterized by data selected from: a powder XRD pattern with peaks at 9.1°, 10.3°, 18.6°, 21.6°, and 22.7°±0.2° 2θ; a powder XRD as shown in FIG. 11; a solid-state $^{13}$C NMR spectrum with signals at 122.3, 151.2 and 170.2±0.2 ppm; a solid-state $^{13}$C NMR spectrum having chemical shift differences between the signal exhibiting the lowest chemical shift and another in the chemical shift range of 100 to 190 ppm of 18.8, 47.7 and 66.7±0.1 ppm; a solid-state $^{13}$C NMR spectrum is depicted in FIG. 23 or 24; and any combinations thereof. In the above embodiment, the signal exhibiting the lowest chemical shift in the chemical shift area of 100 to 190 ppm is typically at about 103.5±1 ppm.

Alternatively, Form S14 can be characterized by a powder XRD pattern with peaks at 9.1°, 10.3°, 18.6°, 19.5°, 21.6°, 22.7°, 24.1°, 25.2°, and 27.0°±0.2° 2θ. In addition, Sitagliptin sulfate Form S14 can be characterized by any combination of the above data.

As discussed above, a high degree of crystallinity is generally a desired property for pharmaceutical materials, primarily because in general, crystalline materials demonstrate higher chemical stability compared to their less-ordered counterparts. On the other hand, a significant advantage of disordered materials is their higher solubility relatively to their crystalline counterparts.

Crystalline form S14 of Sitagliptin sulfate demonstrated both of these two properties, i.e., it possesses both high crystallinity and high water solubility.

For example, the X-ray powder diffraction pattern of Form S14 indicates that it is highly crystalline. In addition Form S14 was found to be highly soluble in different aqueous media, as summarized in the following table:

| Medium | Concentration (g/mL) |
|---|---|
| pH 1.2, 37° C. | 0.50 |
| pH 4.5 37° C. | 0.50 |
| pH 6.8 37° C. | 0.33 |
| pH 7.8 37° C. | 0.30 |
| Water 37° C. | 0.30 |

Solubility was tested by addition of portions of 25 mL solution to 25 mg of STG salt and stirring it at 37° C. for 1-2 minutes till dissolved. Form S14 was also found to be chemically and polymorphically stable. No degradation or polymorphic transformation was observed after six months at 25° C.

Figure 13:
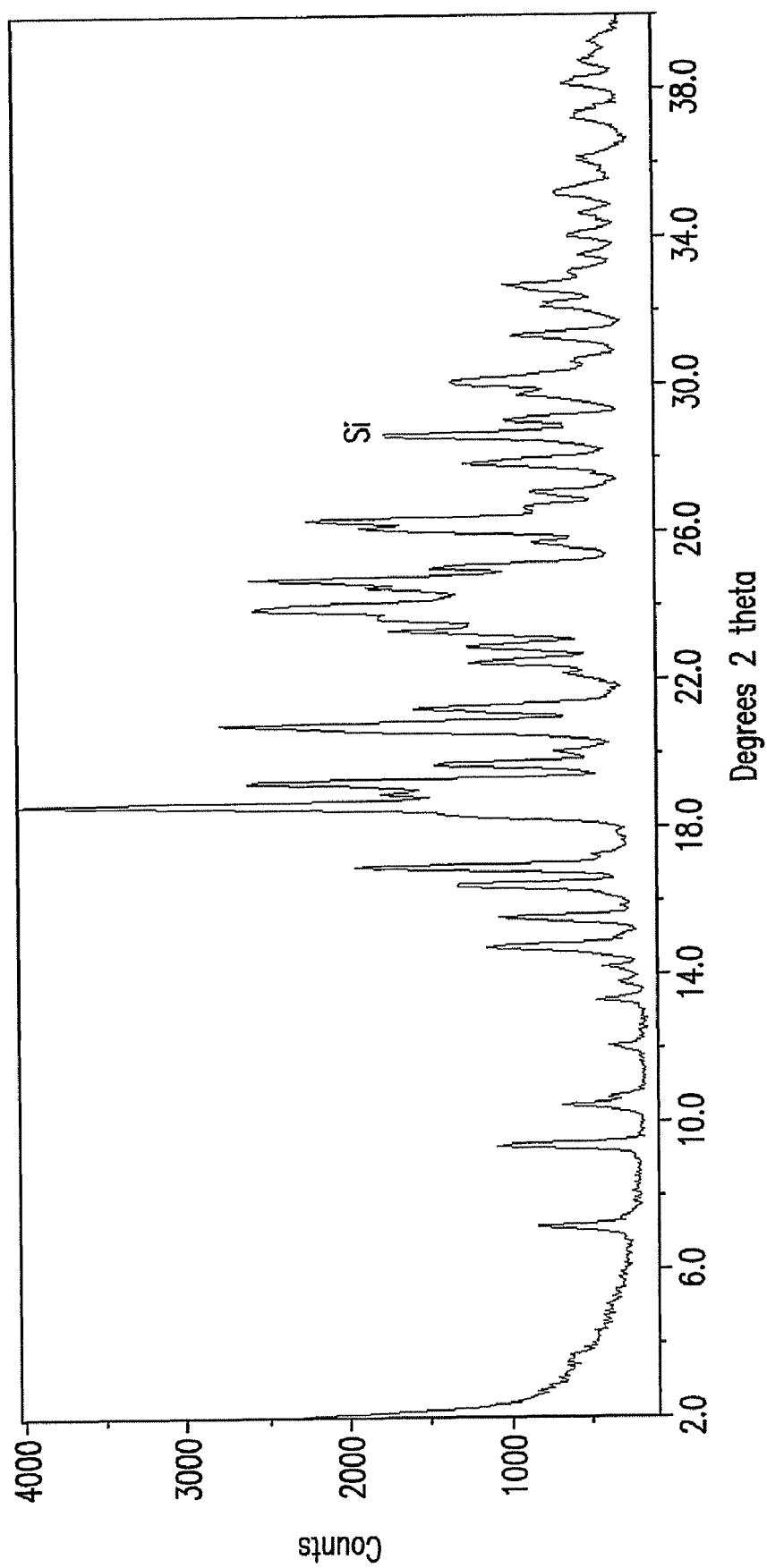
FIG. 13 provides a powder XRD pattern of crystalline Form S16 of Sitagliptin sulfate FIG. 14 provides a powder XRD pattern of crystalline Form E3 of Sitagliptin acetate.
Figure 25:
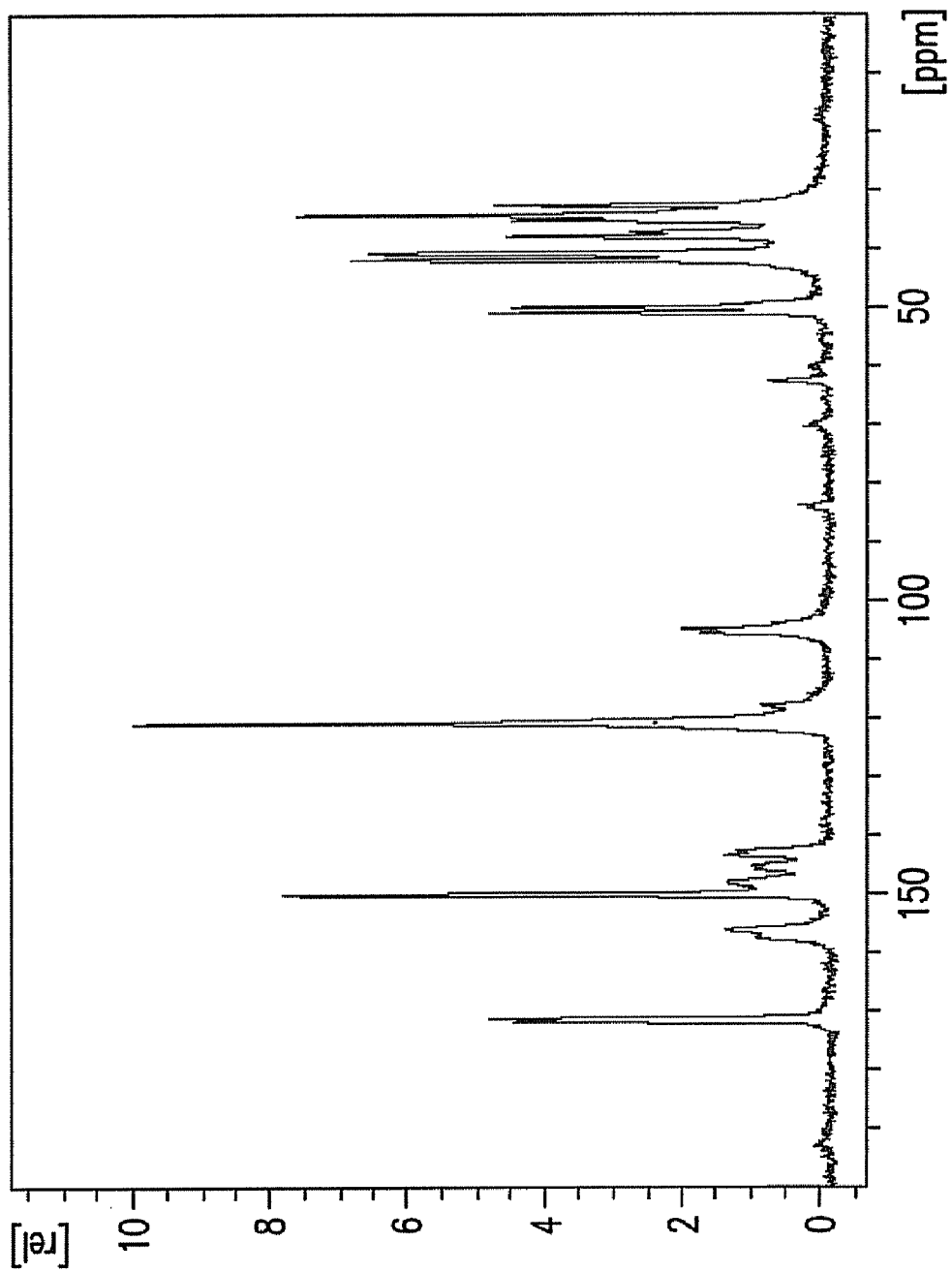
FIG. 25 provides a solid state $^{13}C$ NMR spectrum of crystalline Form S16 of Sitagliptin sulfate in the 0-200 ppm range.
Figure 26:
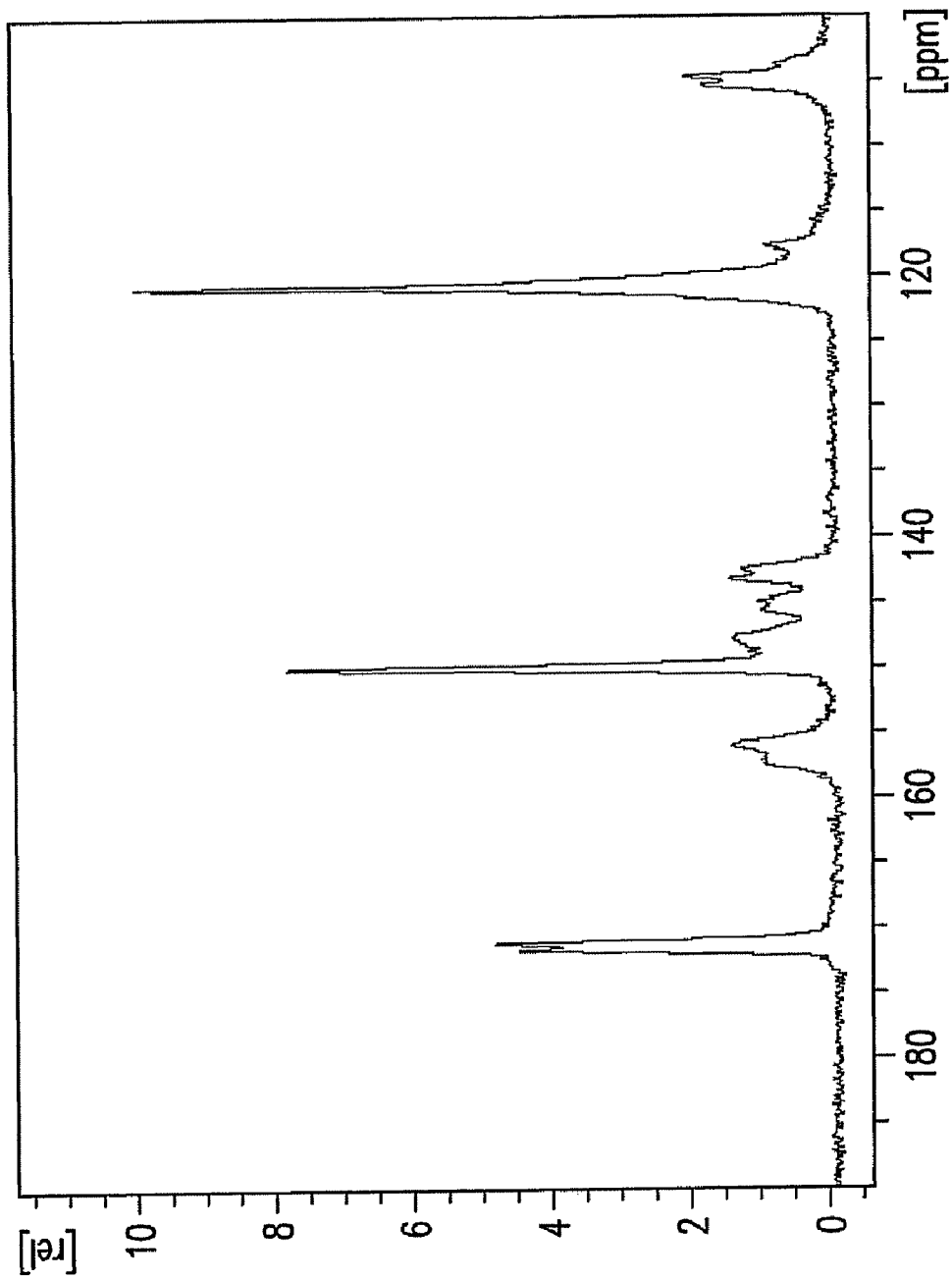
FIG. 26 provides a solid state $^{13}C$ NMR spectrum of crystalline Form S16 of Sitagliptin sulfate in the 100-190 ppm range.

In another embodiment, the invention provides a crystalline Sitagliptin sulfate, designated as Form S16. Form S16 is a hydrate, for example a sesquihydrate. Form S16 can be characterized by data selected from: a powder XRD pattern with peaks at 9.2°, 16.3°, 18.5°, 20.6°, and 23.8°±0.2° 2θ; a powder XRD as shown in FIG. 13; a solid-state $^{13}$C NMR spectrum with signals at 120.8, 150.0 and 171.1±0.2 ppm; a solid-state $^{13}$C NMR spectrum having chemical shift differences between the signal exhibiting the lowest chemical shift and another in the chemical shift range of 100 to 190 ppm of 16.1, 45.3 and 66.4±0.1 ppm; a solid-state $^{13}$C NMR spectrum as depicted in FIG. 25 or 26; and any combination thereof. In the above embodiment, the signal exhibiting the lowest chemical shift in the chemical shift area of 100 to 190 ppm is typically at about 104.7±1 ppm.

Alternatively, Form S16 can be characterized by a powder XRD pattern with peaks at 7.0°, 9.2°, 16.3°, 16.8°, 18.5°, 19.1°, 20.6°, 23.8°, 24.5°, and 26.1°±0.2° 2θ. In addition, Sitagliptin sulfate Form S16 can be characterized by any combination of the above data.

The X-ray powder diffraction pattern of Form S16 indicates that it is highly crystalline. Form S16 has further been found to be freely soluble according to the classification of the European Pharmacopoeia Commission 01/2008:5110. About 100 mg of Sitagliptin sulfate Form S16 has been found to be soluble in 1 mL of water.

Another advantage observed for Form S16 is that this crystal form demonstrates a constant water content (2.9%, which corresponds to the sesquihydrate). This property of being a stoichiometric hydrate is believed to correlate to the form's low hygroscopicity. Low hygroscopicity is believed to positively correlate with polymorphic stability and also to ease of handling during formulation processes.

Figure 19:
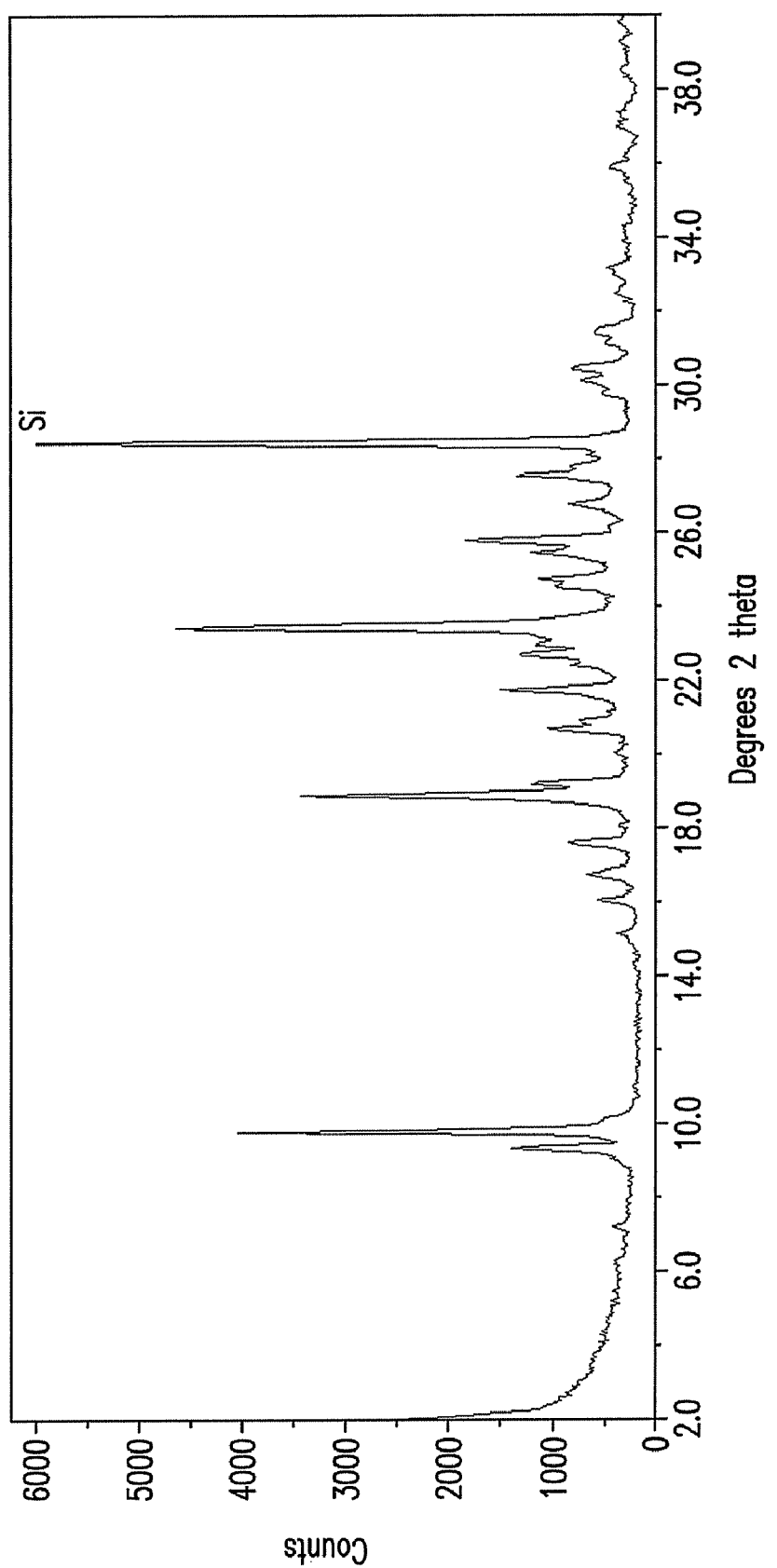
FIG. 19 provides a powder XRD pattern of crystalline Form S17 of Sitagliptin sulfate.

In another embodiment, the present invention provides a crystalline Sitagliptin sulfate, designated Form S17. Form S17 can be characterized by a powder XRD pattern with peaks at 9.3°, 9.8°, 18.9°, 21.8°, and 23.4°±0.2° 2θ; or by a powder XRD pattern as shown in FIG. 19; or by combinations thereof.

Alternatively, Sitagliptin sulfate Form S17 can be characterized by a powder XRD pattern with peaks at 9.3°, 9.8°, 17.6°, 18.9°, 19.2°, 21.8°, 22.7°, 23.4°, 25.8°, and 27.5°±0.2° 2θ. In addition, Sitagliptin sulfate Form S17 can be characterized by any combination of the above data.

Figure 20:
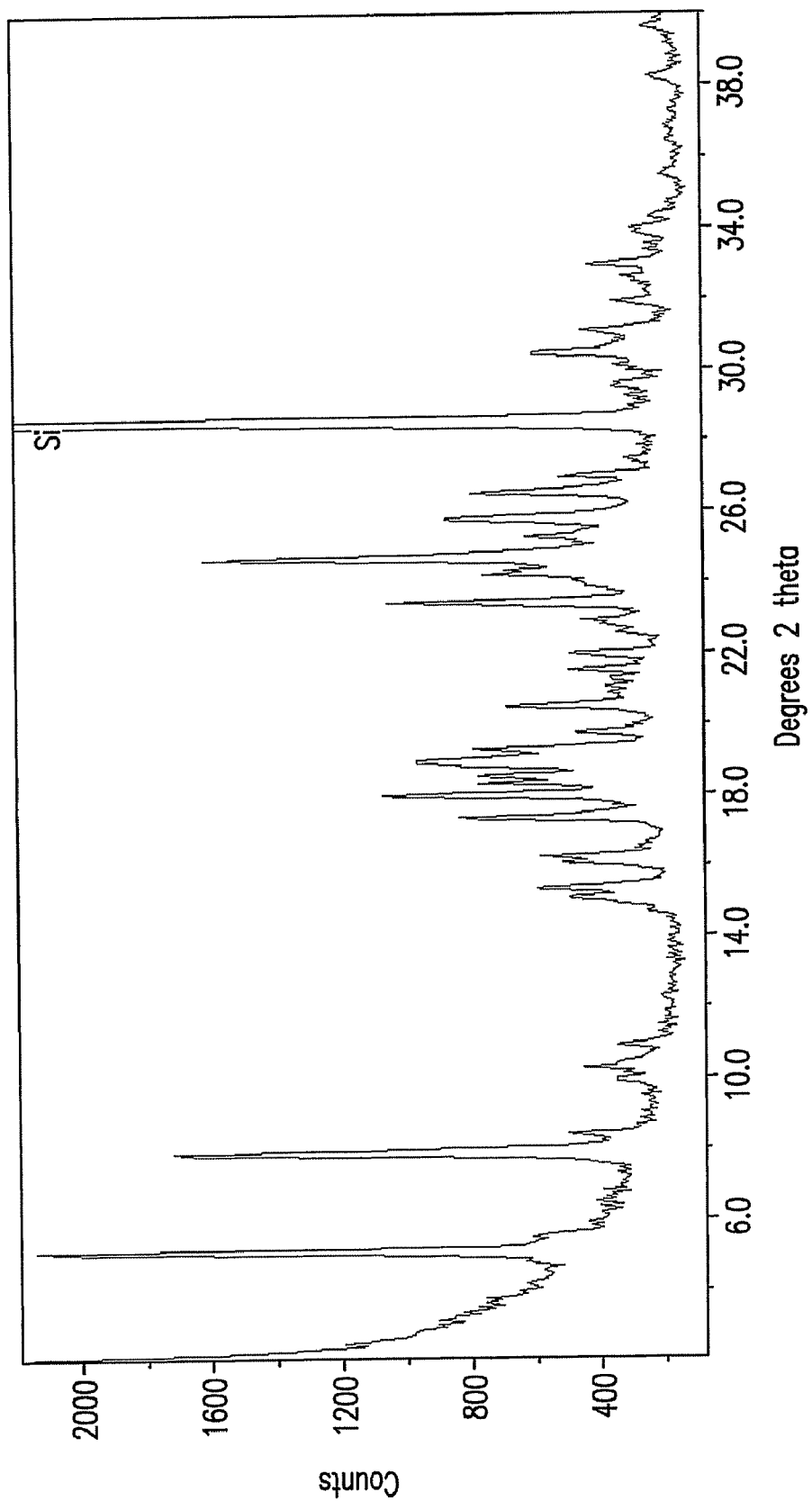
FIG. 20 provides a powder XRD pattern of crystalline Form S18 of Sitagliptin sulfate.

In another embodiment, the invention provides a crystalline Sitagliptin sulfate, designated as Form S18. Form S18 can be characterized by a powder XRD pattern with peaks at 5.1°, 7.9°, 17.9°, 23.4° and 24.6°±0.2° 2θ; or by a powder XRD as shown in FIG. 20; or by combinations thereof.

Alternatively, Form S18 can be characterized by a powder XRD pattern with peaks at 5.1°, 7.9°, 17.3°, 17.9°, 18.8°, 20.4°, 23.4°, 24.6°, 25.7°, and 26.5°±0.2° 2θ. In addition, Sitagliptin sulfate Form S18 can be characterized by any combination of the above data.

Figure 36:
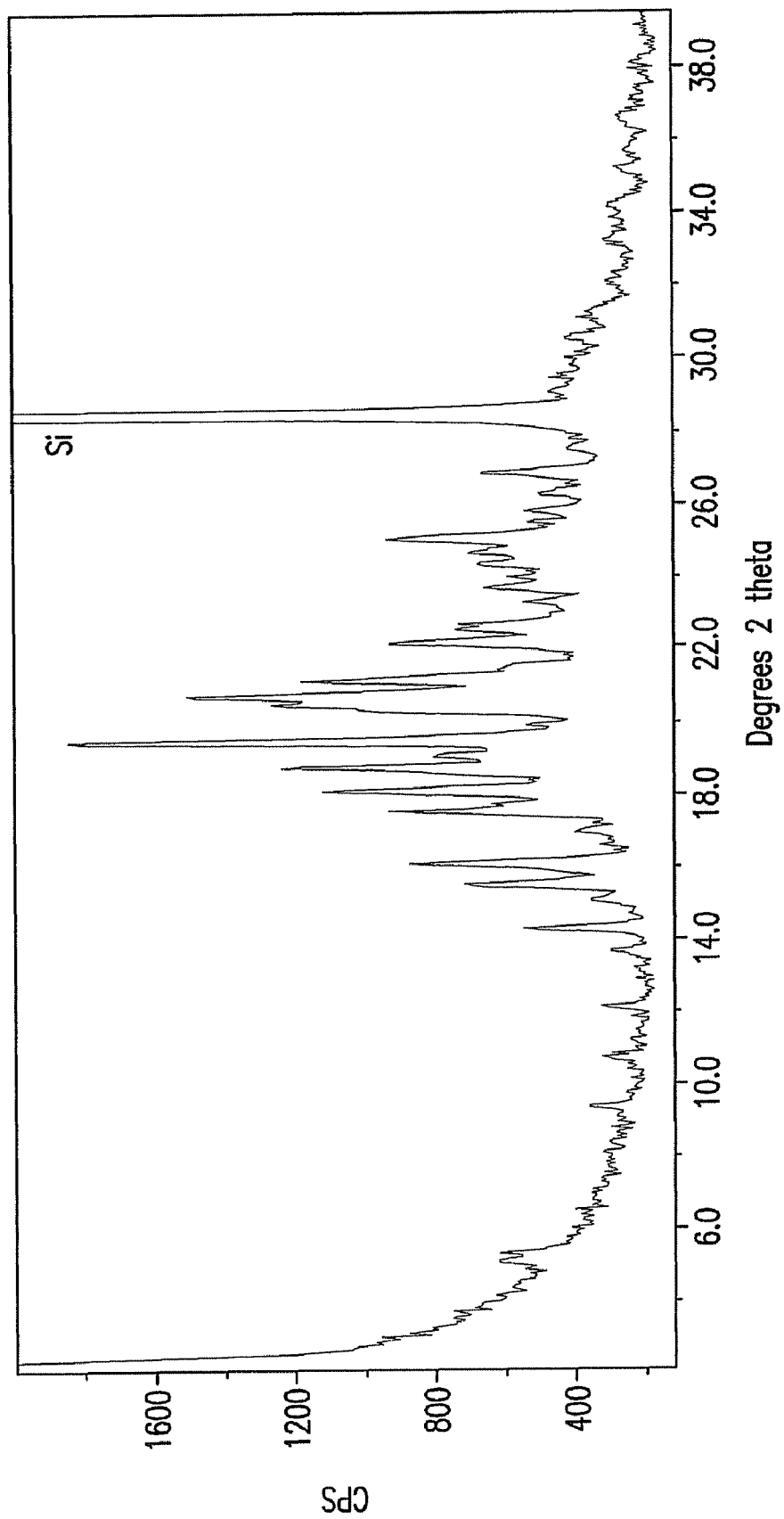
FIG. 36 provides a powder XRD pattern of crystalline Form S19 of Sitagliptin sulfate.

In another embodiment, the present provides a crystalline Sitagliptin sulfate, designated as Form S19. Form S19 can be characterized by a powder XRD pattern with peaks at 16.1°, 17.5°, 18.0°, 18.7°, and 19.4°±0.2° 2θ; or by a powder XRD as shown in FIG. 36; or by combinations thereof.

Form S19 can be further characterized by additional PXRD peaks at 14.2°, 15.4°, 20.7°, 21.1°, and 22.1°±0.2° 2θ.

Figure 42:
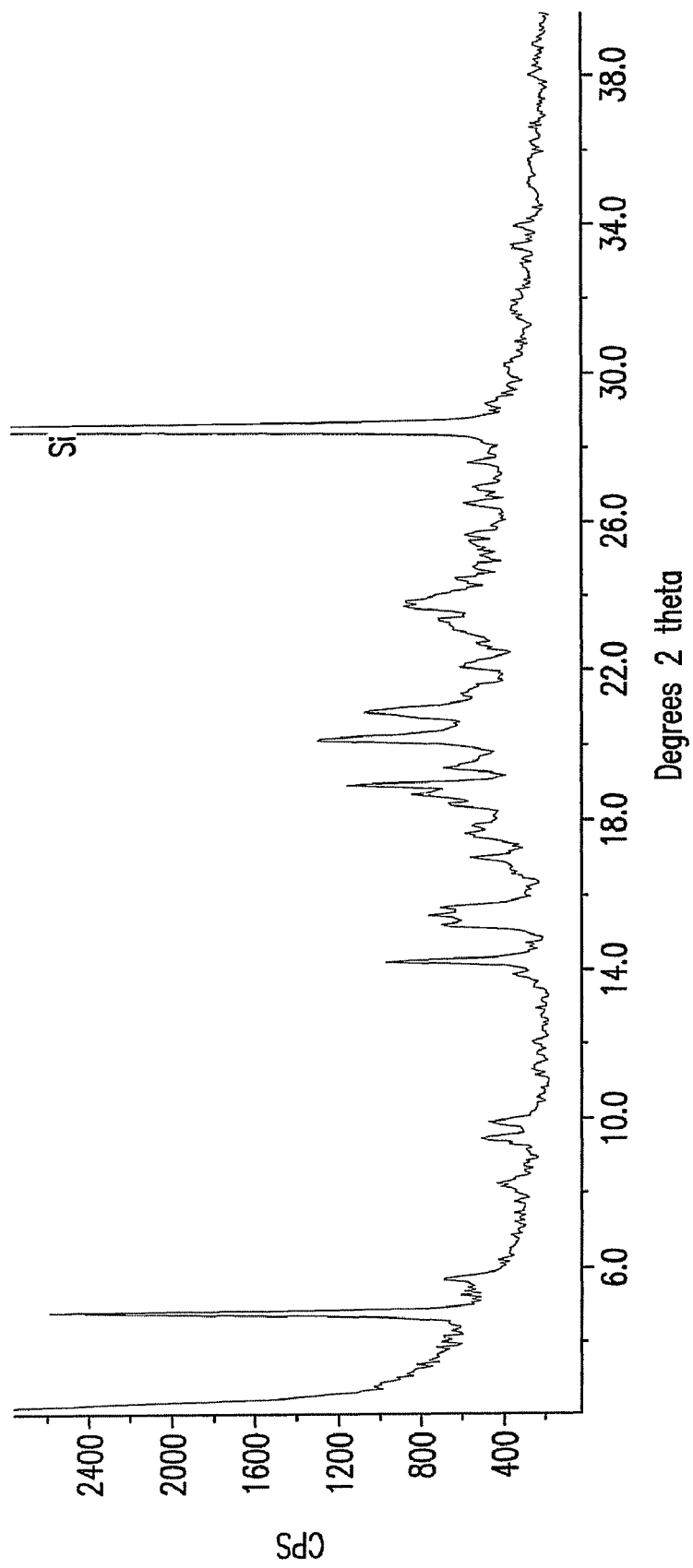
FIG. 42 provides a powder XRD pattern of crystalline Forms S20 of Sitagliptin sulfate.

In another embodiment, the invention provides a crystalline Sitagliptin sulfate, designated as Form S20. Form S20 can be characterized by a powder XRD pattern with peaks at 4.8°, 14.2°, 20.2°, 21.9°, and 22.2°±0.2° 2θ; or by a powder XRD as shown in FIG. 42; or by combinations thereof.

Alternatively, Form S20 can be characterized with additional powder XRD pattern at 5.7°, 9.4°, 9.9°, 17.0°, and 18.9°±0.2° 2θ. In addition, Sitagliptin sulfate Form S20 can be characterized by any combination of the above data.

The present invention provides novel crystalline forms of Sitagliptin L-malate. The provided new forms of Sitagliptin L-malate preferably have advantageous properties selected from at least one of: high crystallinity, solubility, dissolution rate, morphology, thermal and mechanical stability to polymorphic conversion and/or to dehydration, storage stability, low content of residual solvent, a lower degree of hygroscopicity, flowability, and advantageous processing and handling characteristics such as compressibility, and bulk density.

Figure 2:
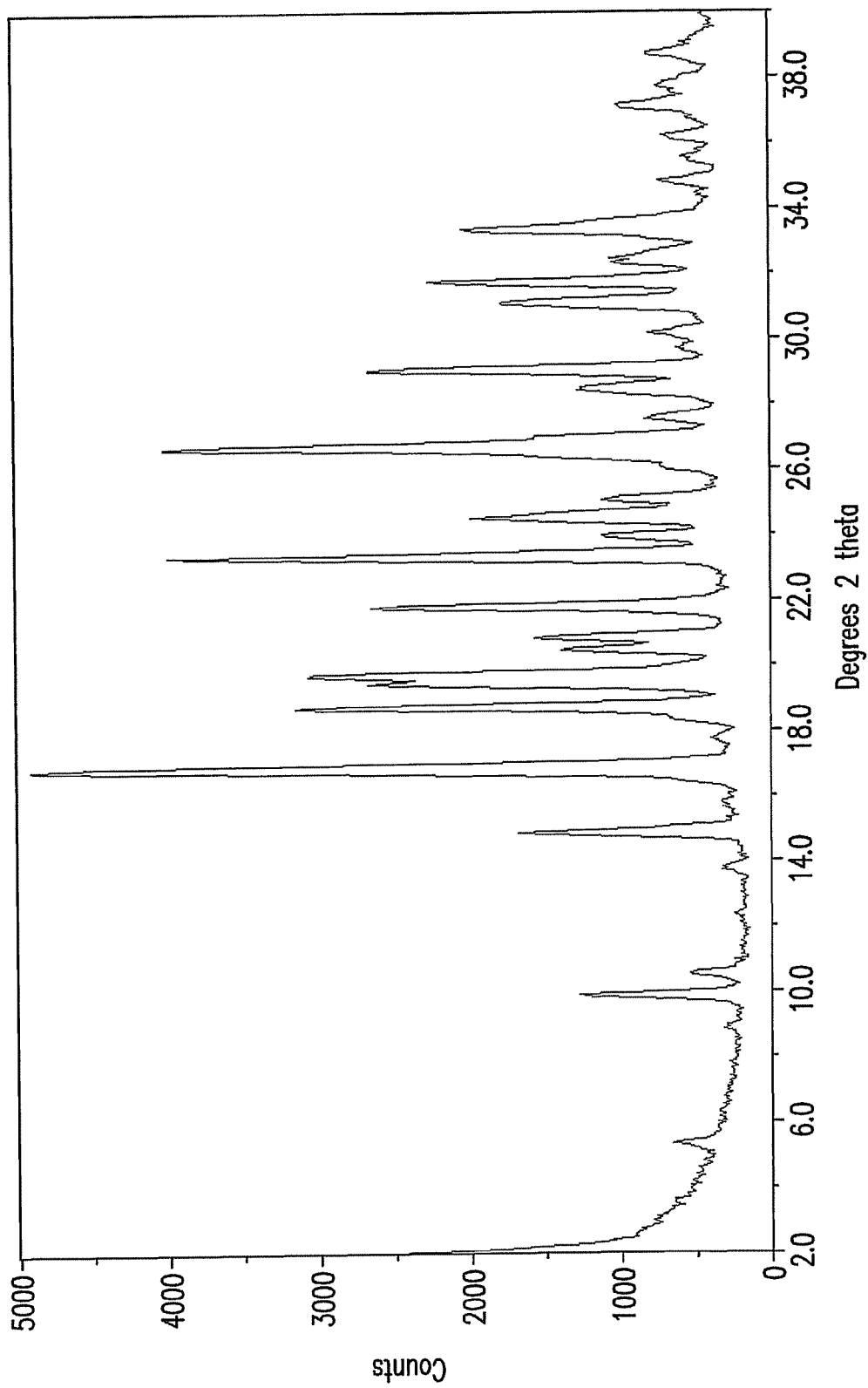
FIG. 2 provides a powder XRD pattern of crystalline Form I2 of Sitagliptin L-malate.

In another embodiment, the present invention provides a crystalline Sitagliptin L-malate, designated Form I2. Form I2 can be characterized by a powder XRD pattern with peaks at 16.8°, 18.7°, 19.7°, 23.3°, and 26.7°±0.2° 2θ; or by a powder XRD pattern as shown in FIG. 2; or by combinations thereof.

Alternatively, Sitagliptin L-malate Form I2 can be characterized by a powder XRD pattern with peaks at 9.9°, 14.8°, 16.8°, 18.7°, 19.7°, 20.8°, 21.8°, 23.3°, 26.7°, and 29.0°±0.2° 2θ. In addition, Sitagliptin L-malate Form I2 can be characterized by any combination of the above data.

In another embodiment, the present invention provides a crystalline Sitagliptin L-malate, designated Form I3.

Figure 29:
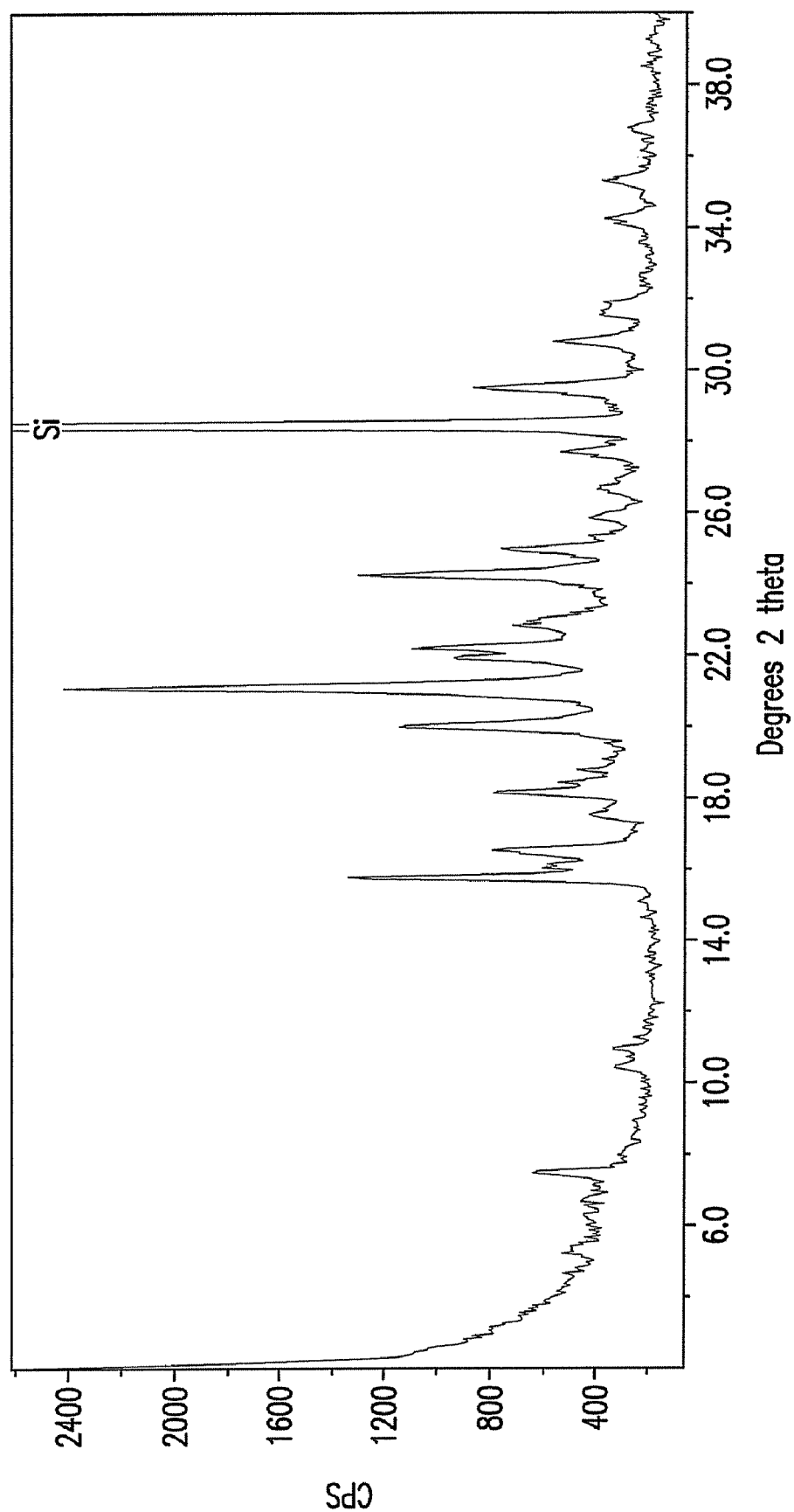
FIG. 29 provides a powder XRD pattern of crystalline Form I3 of Sitagliptin L-malate.

The skilled person may characterize Form I3 by selecting one, two, three, four, five or more characteristic peaks from the diffractogram depicted in FIG. 29, that includes peaks at 7.5°, 10.5°, 11.0°, 15.8°, 16.1°, 16.5°, 17.6°, 18.2°, 18.8°, 20.0°, 21.1°, 21.9°, 22.2°, 22.9°, 24.3°, 25.0°, 25.3°, 25.9°, 26.7°, 27.7°, and 29.5° two theta±0.2° two theta.

Figure 32:
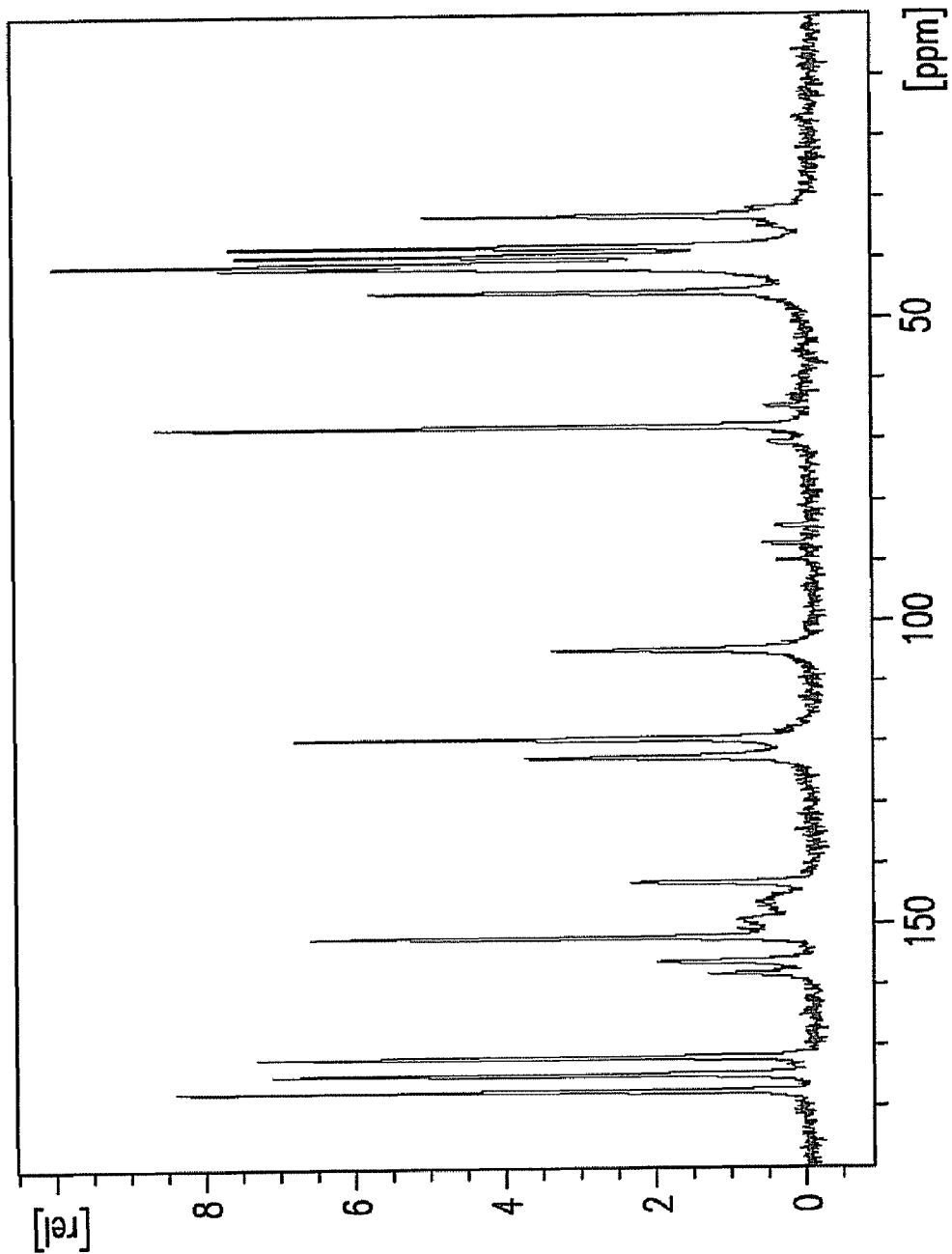
FIG. 32 provides a solid-state $^{13}C$ NMR spectrum of Sitagliptin acetate Form I3 in the 0-190 ppm range.
Figure 33:
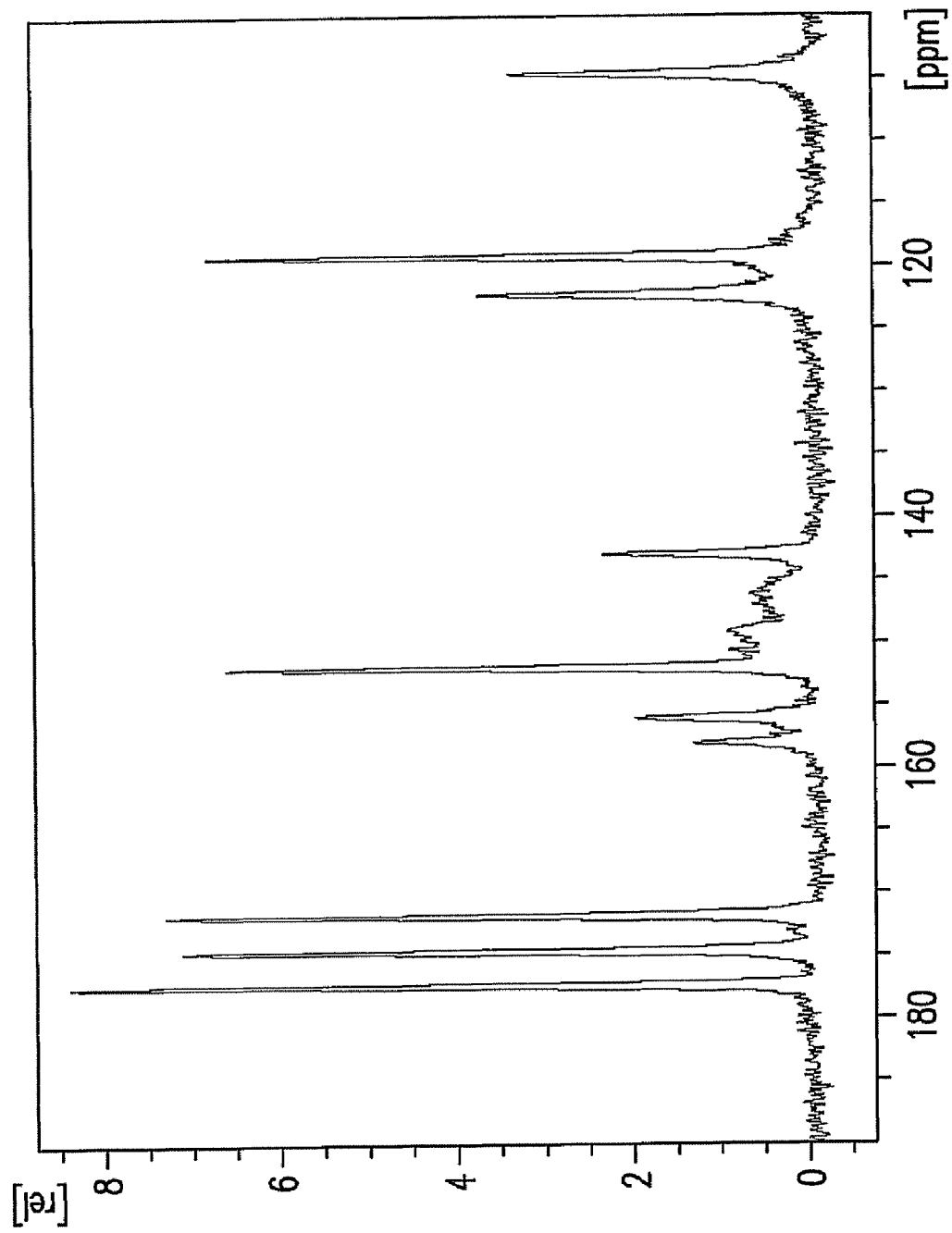
FIG. 33 provides a solid-state $^{13}C$ NMR spectrum of Sitagliptin acetate Form I3 in the 100-190 ppm range.

Form I3 can be characterized, for example by data selected from: an X-ray powder diffraction pattern having peaks at 15.8°, 20.0°, 21.1°, 22.2°, and 24.3° two theta±0.2 degrees two theta; an X-ray powder diffraction pattern substantially as depicted in FIG. 29; a solid-state $^{13}$C NMR spectrum with signals at about 119.2, 171.8 and 174.6±0.2 ppm; a solid-state $^{13}$C NMR spectrum having chemical shifts differences between the signal exhibiting the lowest chemical shift and another in the chemical shift range of 100 to 190 ppm of about 14.6, 67.2 and 70.0±0.1 ppm; $^{13}$C NMR spectrum is depicted in FIGS. 32 and 33; and by combinations thereof. Wherein, the signal exhibiting the lowest chemical shift in the chemical shift area of 100 to 190 ppm is typically at about 104.6±1 ppm.

Alternatively, Form I3 can characterized by an X-ray powder diffraction pattern having peaks at 15.8°, 20.0°, 21.1°, 22.2°, and 24.3° two theta±0.2 degrees two theta; and also having one, two, three, four or five peaks selected from 16.5°, 18.2°, 21.9°, 25.0°, and 29.5° two theta±0.2 degrees two theta. For example, Form I3 can be characterized by an X-ray powder diffraction pattern having peaks at 15.8°, 20.0°, 21.1°, 22.2°, and 24.3° two theta±0.2 degrees two theta, may be further characterized by an X-ray powder diffraction pattern having additional peaks at 16.5°, 18.2°, 21.9°, 25.0°, and 29.5° two theta±0.2 degrees two theta.

Figure 30:
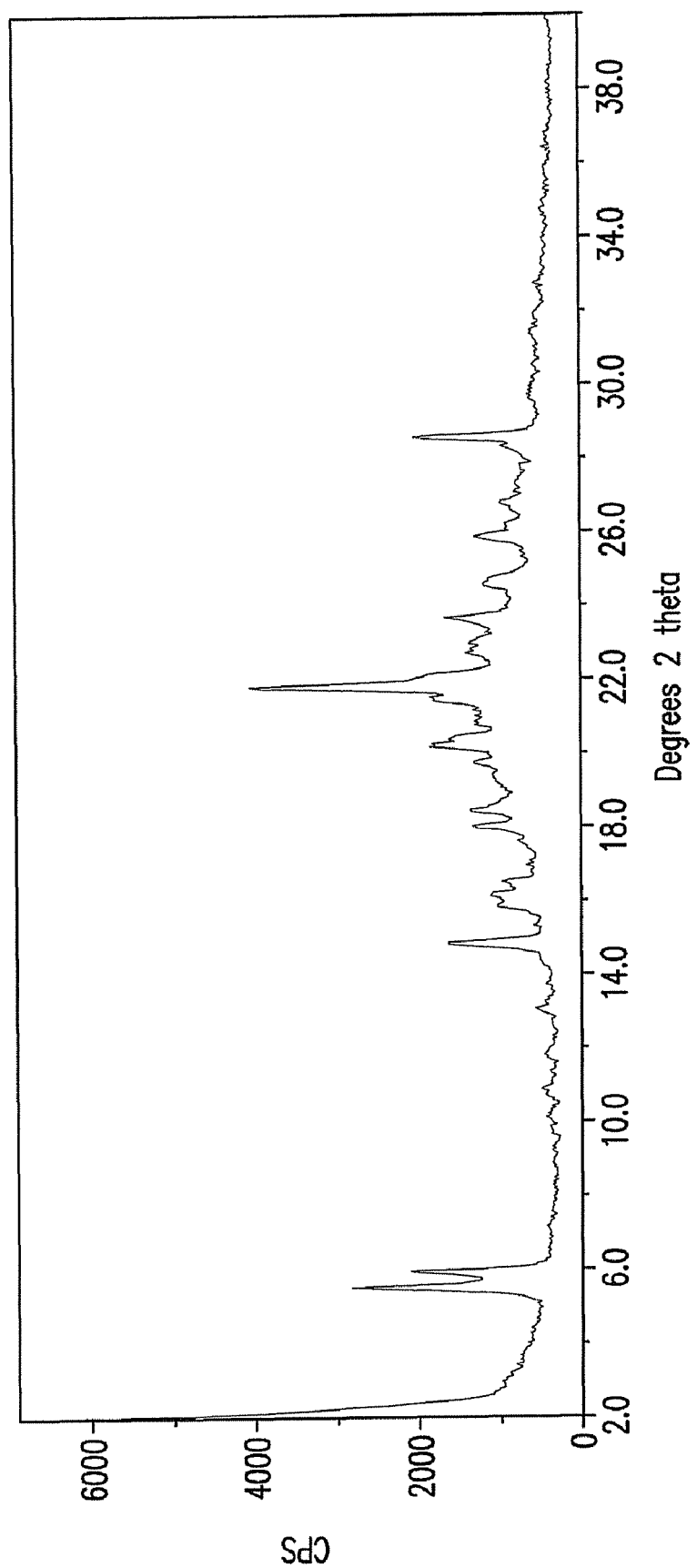
FIG. 30 provides a powder XRD pattern of crystalline Form I4 of Sitagliptin L-malate.
Figure 31:
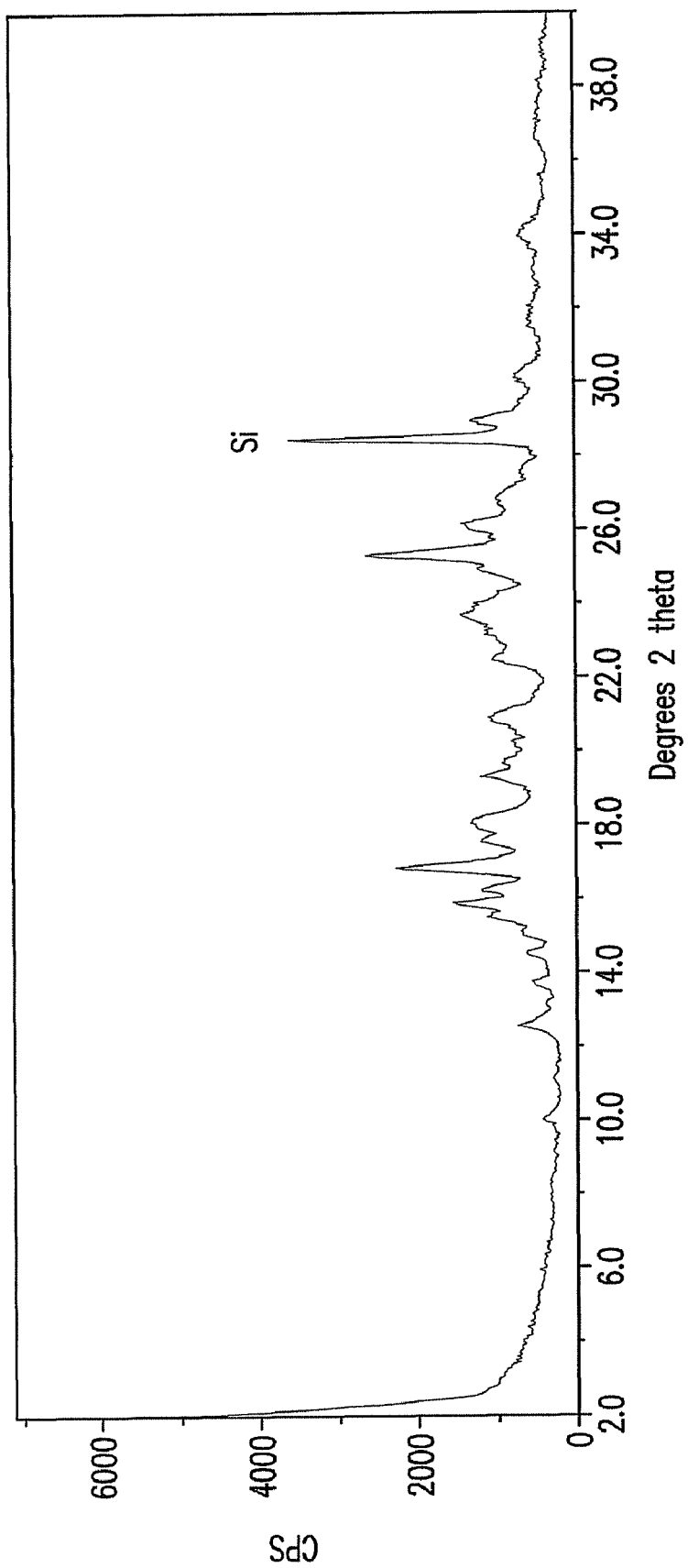
FIG. 31 provides a powder XRD pattern of crystalline Form I5 of Sitagliptin L-malate.
Figure 34:
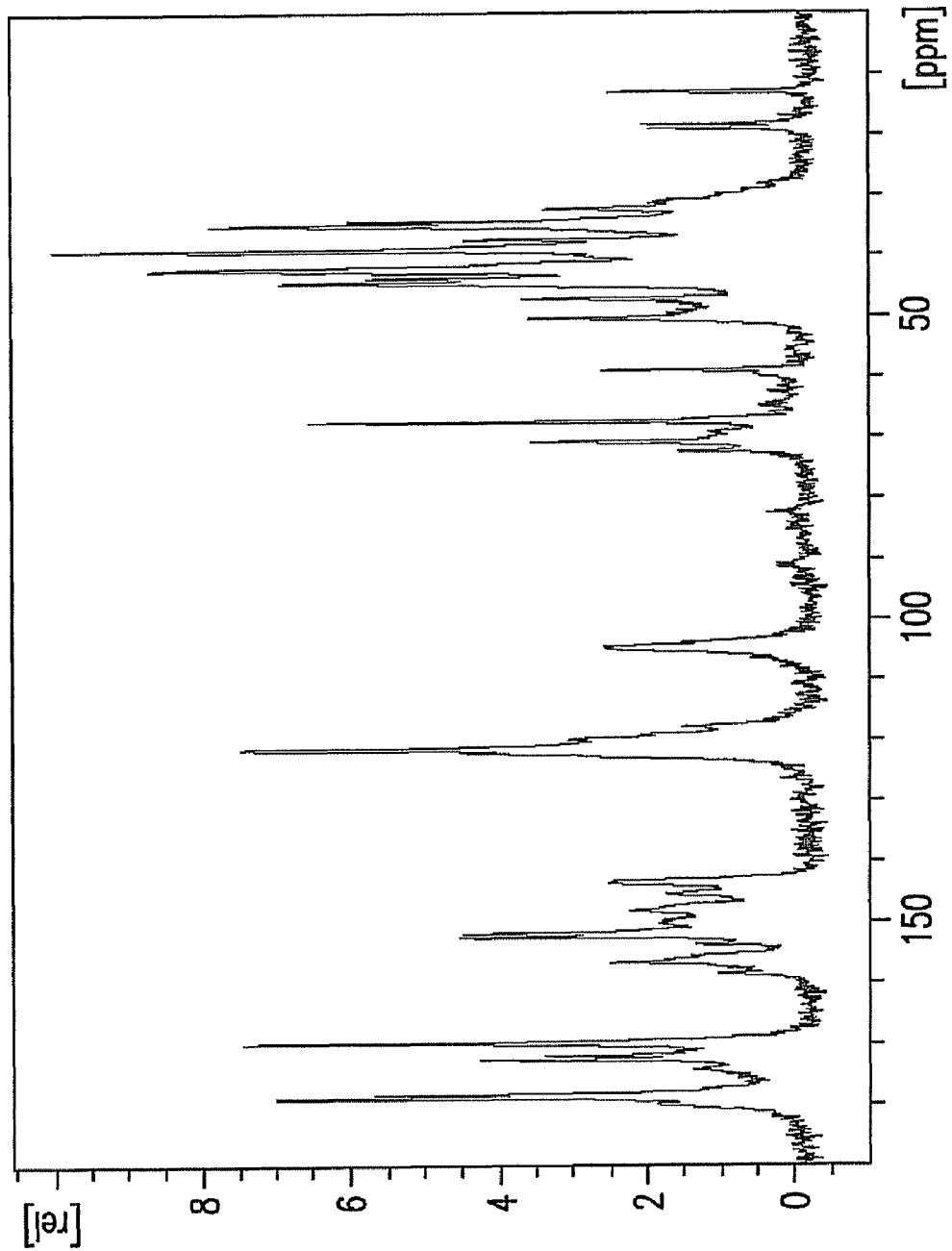
FIG. 34 provides a solid-state $^{13}C$ NMR spectrum of Sitagliptin acetate Form I4 in the 0-190 ppm range.
Figure 35:
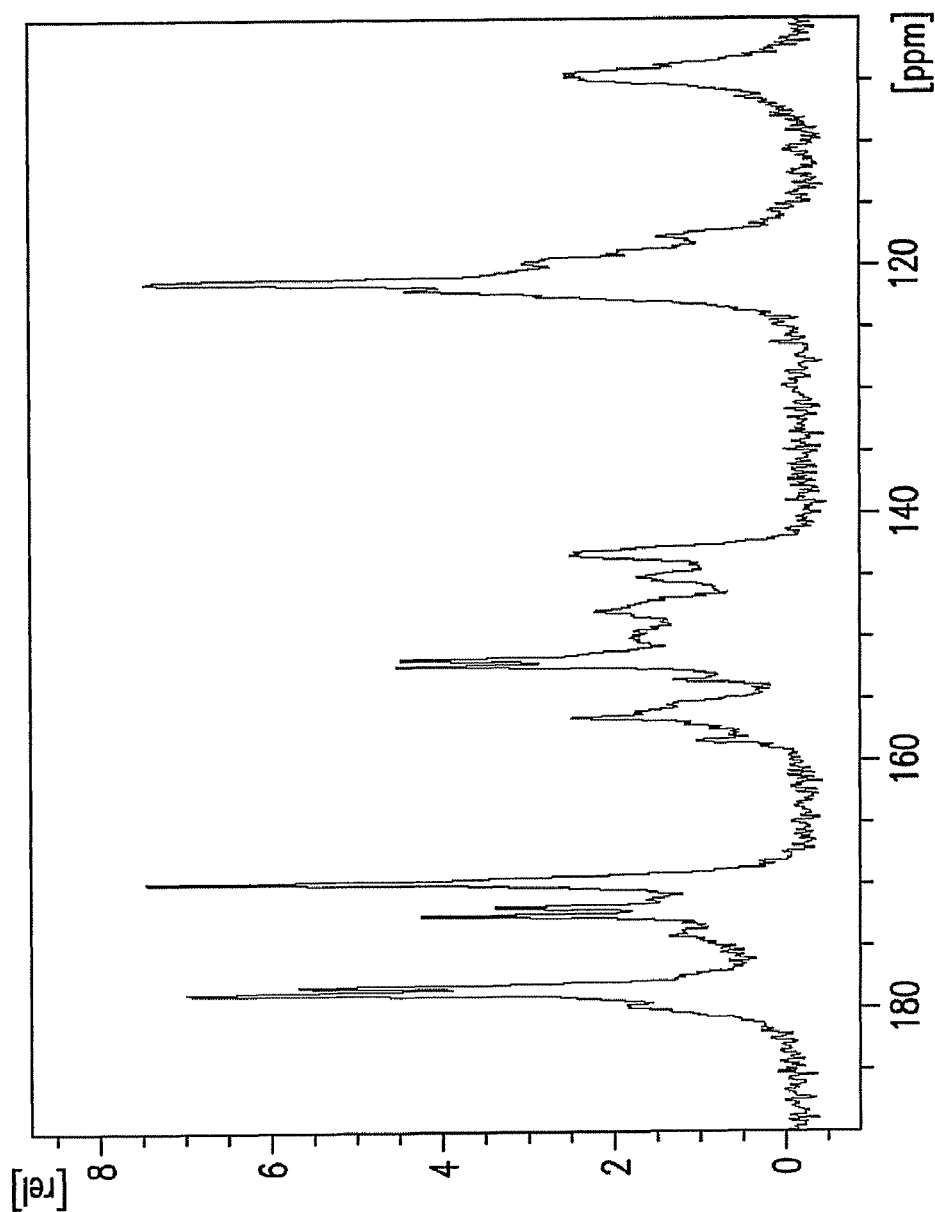
FIG. 35 provides a solid-state $^{13}C$ NMR spectrum of Sitagliptin acetate Form I4 in the 100-190 ppm range.

In another embodiment, the present invention provides crystalline Sitagliptin L-malate, designated Form I4. Form I4 can be characterized by data selected from: a powder XRD pattern with peaks at 5.4°, 5.8°, 14.7°, 21.7°, and 25.7°±0.2° 2θ; or a by a powder XRD pattern as shown in FIG. 30; a solid-state $^{13}$C NMR spectrum with signals at about 121.3, 169.8 and 178.8±0.2 ppm; a solid-state $^{13}$C NMR spectrum having chemical shifts differences between the signal exhibiting the lowest chemical shift and another in the chemical shift range of 100 to 190 ppm of about 16.9, 65.4 and 74.4±0.1 ppm; $^{13}$C NMR spectrum is depicted in FIGS. 34 and 35; and by combinations thereof. Wherein, the signal exhibiting the lowest chemical shift in the chemical shift area of 100 to 190 ppm is typically at about 104.4±1 ppm.

In a specific embodiment, Form I4 can be characterized by a powder XRD pattern with peaks at 5.4°, 5.8°, 14.7°, 17.9°, 18.3°, 20.1°, 21.7°, 23.5°, 25.7°, and 26.6° two theta±0.2 degrees two theta.

In addition, Form I4 can be characterized by any combination of the above data.

In another embodiment, the present invention provides crystalline Sitagliptin L-malate, designated Form I5. Form I5 can be characterized by a powder XRD pattern with peaks at 12.6°, 15.9°, 16.8°, 19.3°, and 25.3°±0.2° 2θ; or a by a powder XRD pattern as shown in FIG. 30; or by combination thereof.

In a specific embodiment, Form I5 can be characterized by a powder XRD pattern with peaks at 12.6°, 14.5°, 15.5°, 15.9°, 16.2°, 16.8°, 19.3°, 20.9°, 23.6°, and 25.3° two theta±0.2 degrees two theta.

In addition, Form I5 can be characterized by any combination of the above data.

The present invention provides novel crystalline forms of Sitagliptin acetate. The provided new forms of Sitagliptin acetate preferably have advantageous properties selected from at least one of: high crystallinity, solubility, dissolution rate, morphology, thermal and mechanical stability to polymorphic conversion and/or to dehydration, storage stability, low content of residual solvent, a lower degree of hygroscopicity, flowability, and advantageous processing and handling characteristics such as compressibility, and bulk density.

Figure 16:
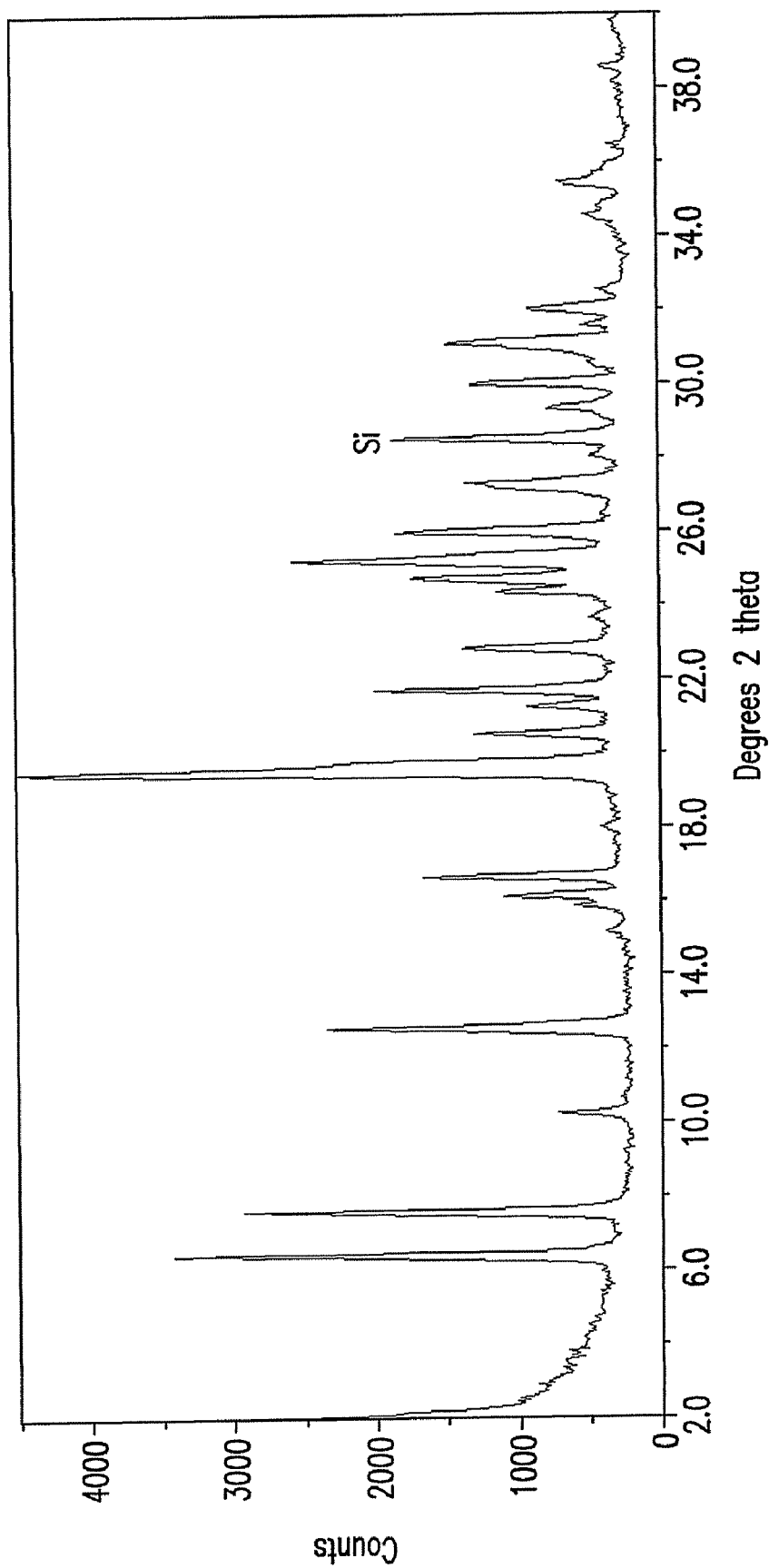
FIG. 16 provides a powder XRD pattern of crystalline Form E2 of Sitagliptin acetate.
Figure 17:
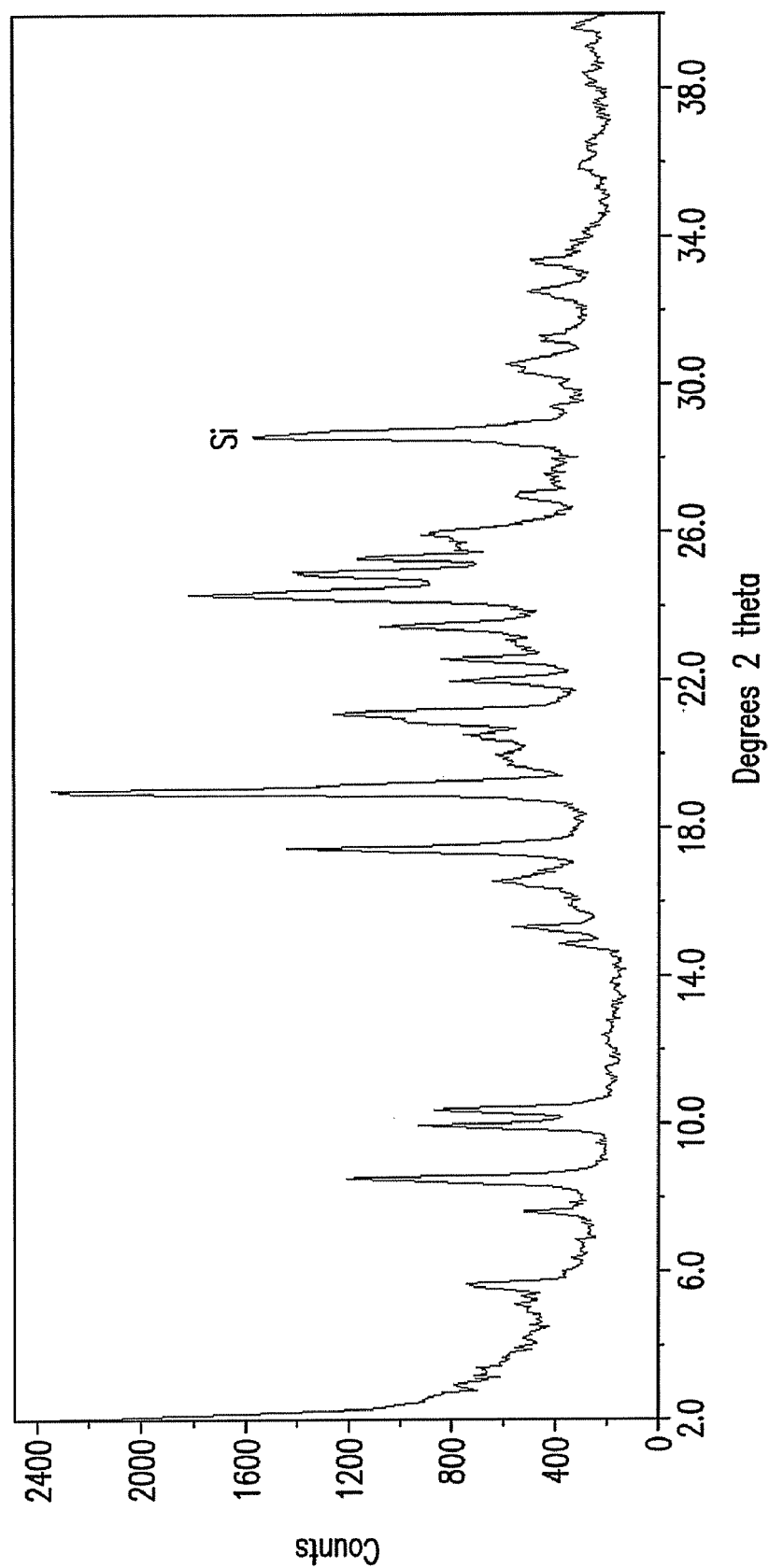
FIG. 17 provides a powder XRD pattern of crystalline Form S13 of Sitagliptin sulfate.

In another embodiment, the present invention provides a crystalline Sitagliptin acetate, designated Form E2. Form E2 can be characterized by a powder XRD pattern with peaks at 6.4°, 7.5°, 12.5°, 16.6°, and 19.4°±0.2° 2θ; or a by a powder XRD pattern as shown in FIG. 16; or by combinations thereof.

Alternatively, Form E2 can be characterized by a powder XRD pattern with peaks at 6.4°, 7.5°, 12.5°, 16.1°, 16.6°, 19.4°, 21.7°, 24.7°, 25.2°, and 25.9°±0.2° 2θ. In addition, Sitagliptin acetate Form E2 can be characterized by any combination of the above data.

Figure 14:
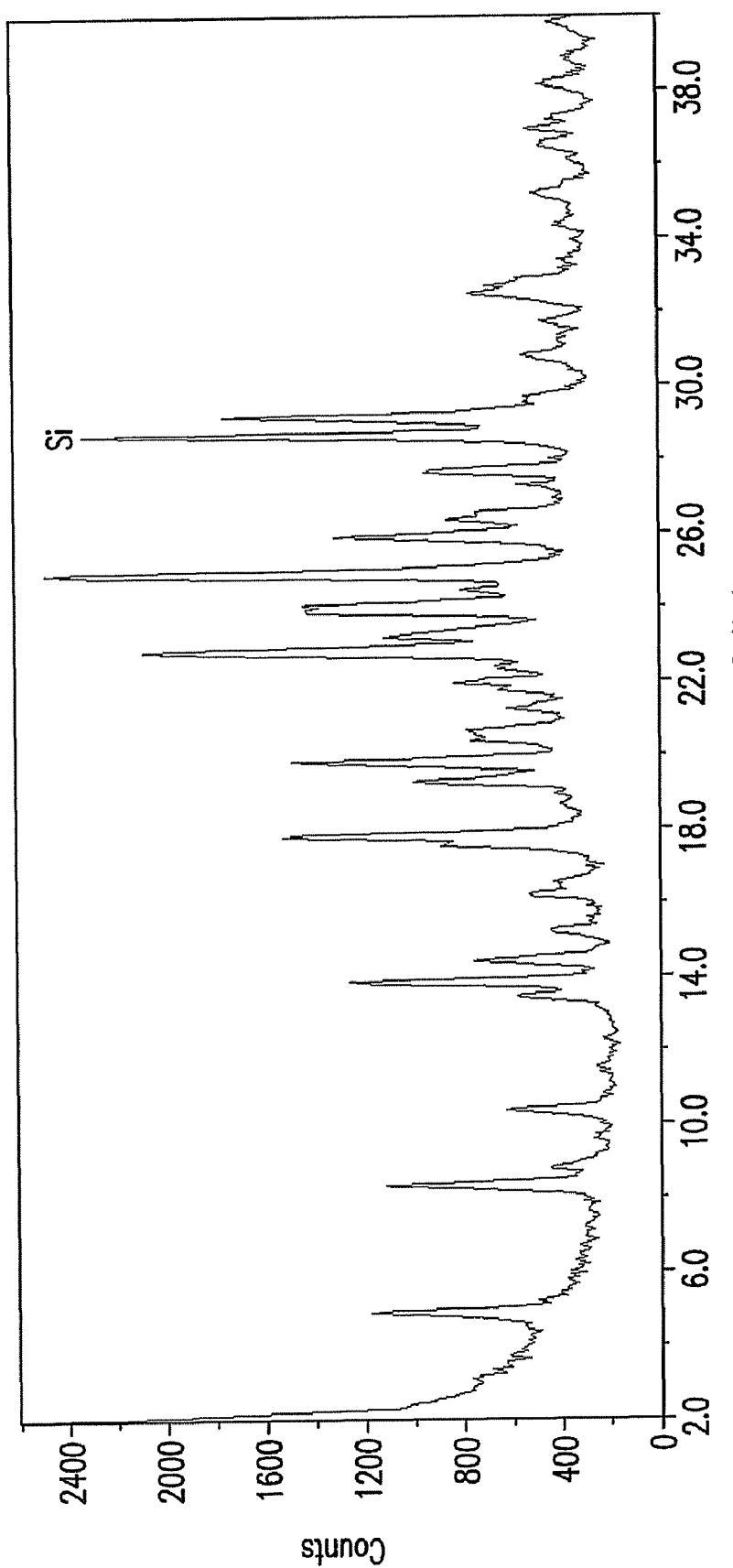

In another embodiment, the present invention provides a crystalline Sitagliptin acetate, designated Form E3. Form E3 can be characterized by a powder XRD pattern with peaks at 4.7°, 8.1°, 13.7°, 14.2°, and 17.6°±0.2° 2θ; or by a powder XRD pattern as shown in FIG. 14; or by combinations thereof.

Alternatively, Form E3 can be characterized by a powder XRD pattern with peaks at 4.7°, 8.1°, 13.7°, 14.2°, 17.6°, 19.1°, 19.6°, 22.6°, 24.7°, and 25.7°±0.2° 2θ. In addition, Sitagliptin acetate Form E3 can be characterized by any combination of the above data.

Figure 15:
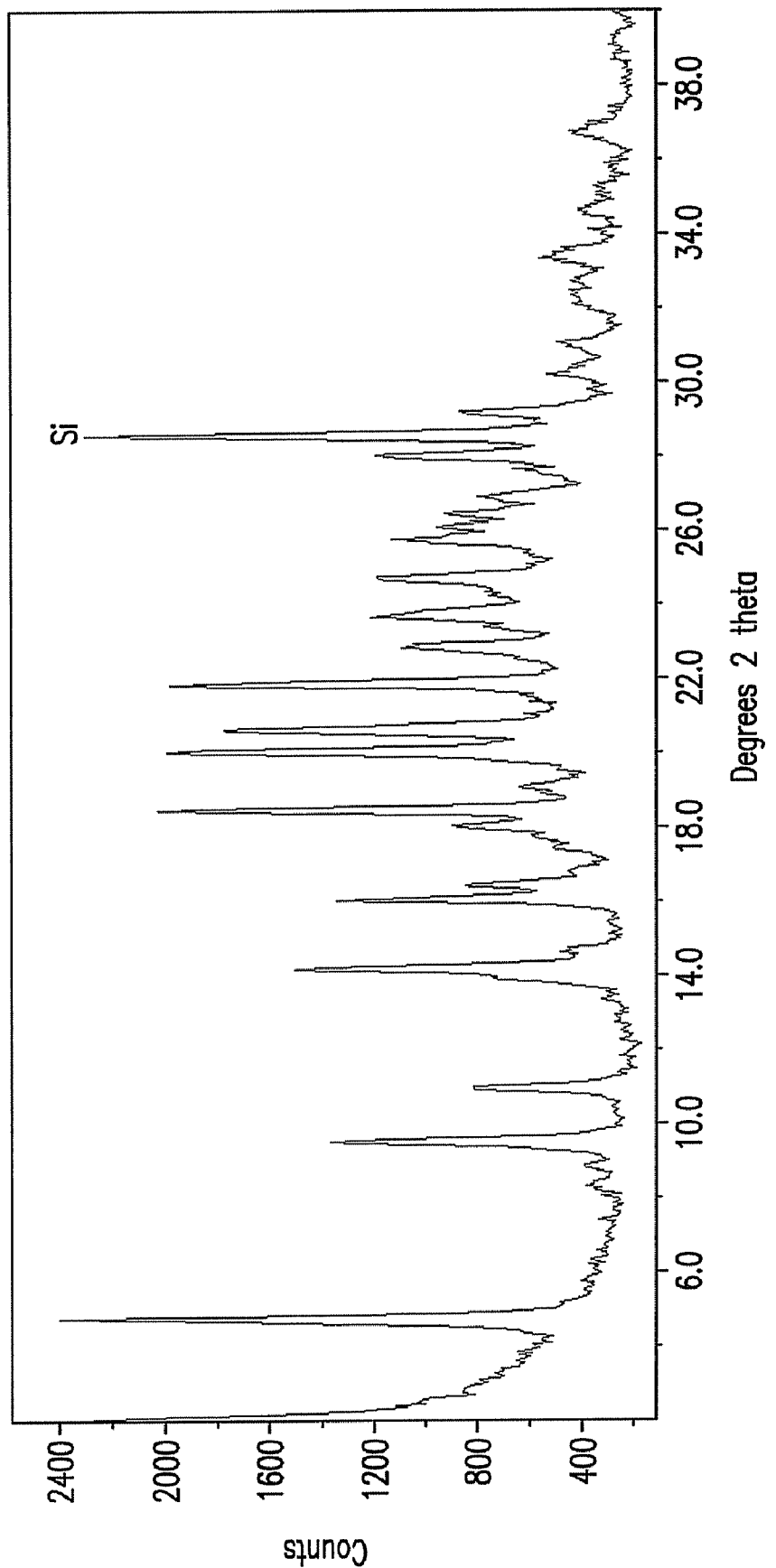
FIG. 15 provides a powder XRD pattern of crystalline Form E4 of Sitagliptin acetate.
Figure 21:
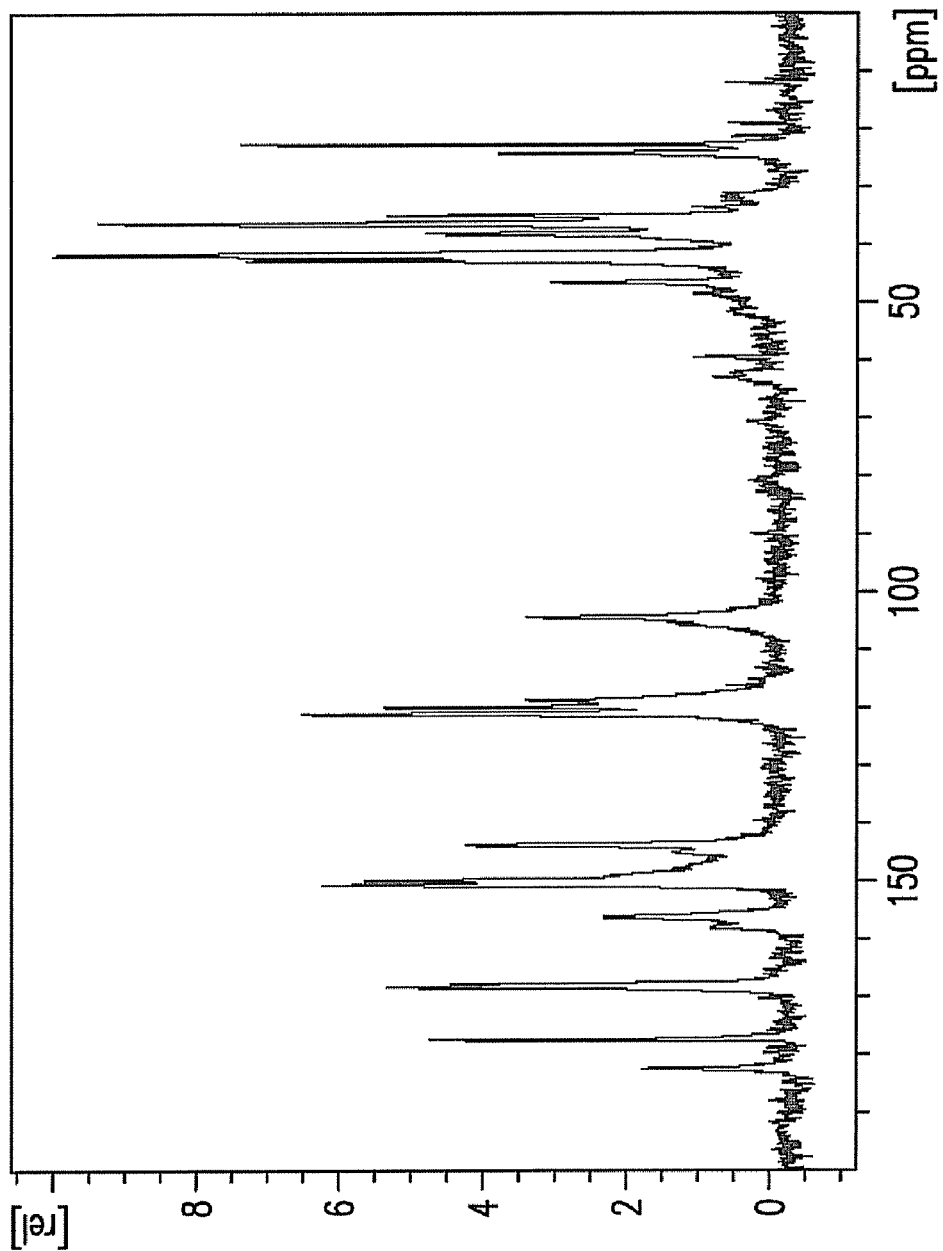
FIG. 21 provides a solid state $^{13}C$ NMR spectrum of crystalline Form E4 of Sitagliptin acetate in the 0-200 ppm range.
Figure 22:
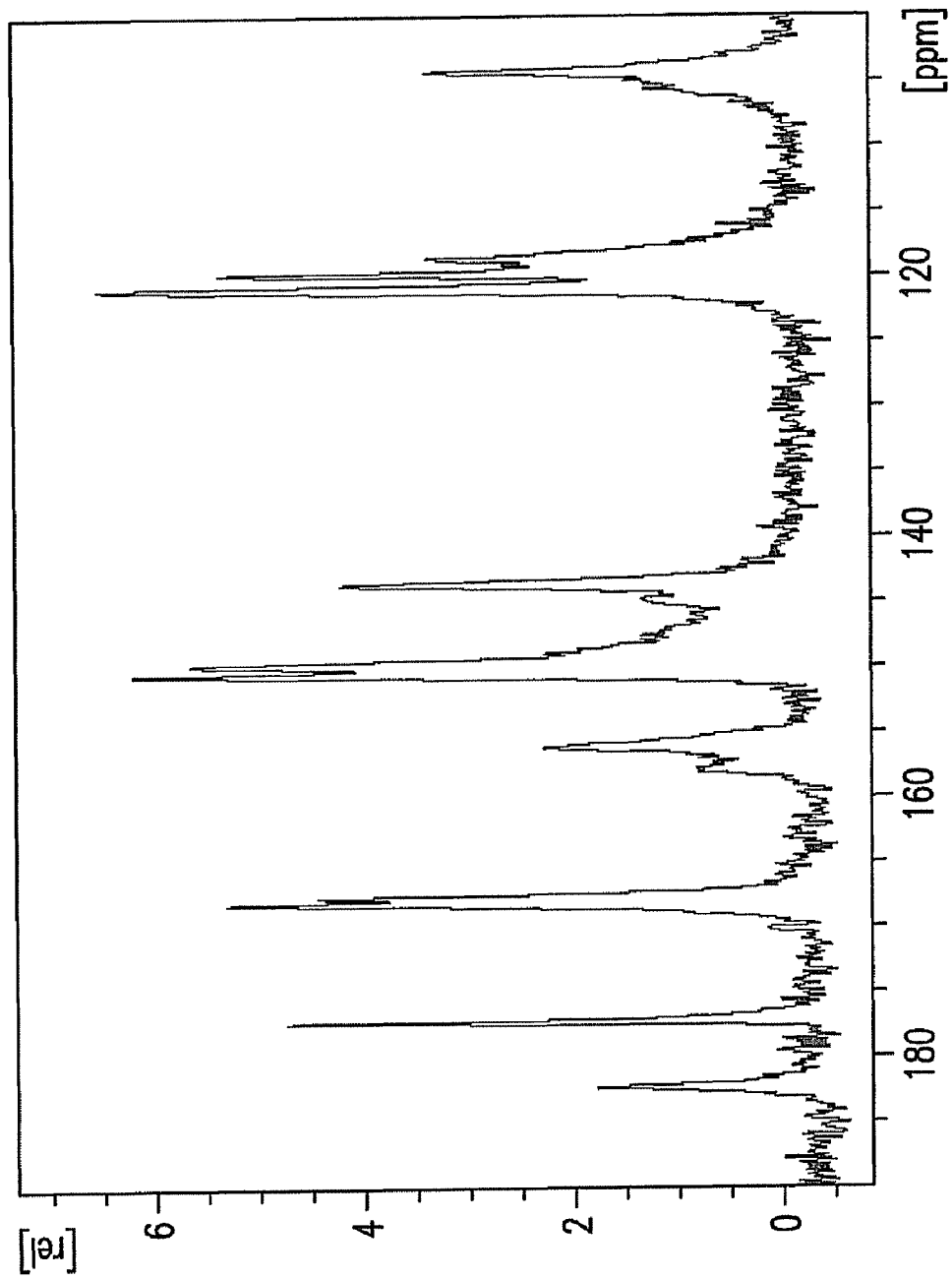
FIG. 22 provides a solid state $^{13}C$ NMR spectrum of crystalline Form E4 of Sitagliptin acetate in the 100-190 ppm range.

In another embodiment, the present invention provides a crystalline Sitagliptin acetate, designated Form E4. Form E4 can be characterized by data selected from: a powder XRD pattern with peaks at 4.7°, 9.4°, 14.1°, 16.0°, and 18.4°±0.2° 2θ; a powder XRD pattern as shown in FIG. 15; a solid-state $^{13}$C NMR spectrum with signals at 120.9, 177.2 and 182.2±0.2 ppm; a solid-state $^{13}$C NMR spectrum having chemical shift differences between the signal exhibiting the lowest chemical shift and another in the chemical shift range of 100 to 190 ppm of 16.6, 72.9 and 77.9±0.1 ppm; a solid-state $^{13}$C NMR spectrum as shown in FIG. 21 or 22; and any combination thereof. In the above embodiment, the signal exhibiting the lowest chemical shift in the chemical shift area of 100 to 190 ppm is typically at about 104.3±1 ppm.

Alternatively, Form E4 can be characterized by a powder XRD pattern with peaks at 4.7°, 9.4°, 10.9°, 14.1°, 16.0°, 18.4°, 20.0°, 20.5°, 21.8°, and 28.0°±0.2° 2θ. In addition, Sitagliptin acetate Form E4 can be characterized by any combination of the above data.

The present invention provides novel crystalline forms of Sitagliptin hydrochloride. The provided new forms of Sitagliptin hydrochloride preferably have advantageous properties selected from at least one of: high crystallinity, solubility, dissolution rate, morphology, thermal and mechanical stability to polymorphic conversion and/or to dehydration, storage stability, low content of residual solvent, a lower degree of hygroscopicity, flowability, and advantageous processing and handling characteristics such as compressibility, and bulk density.

Figure 4:
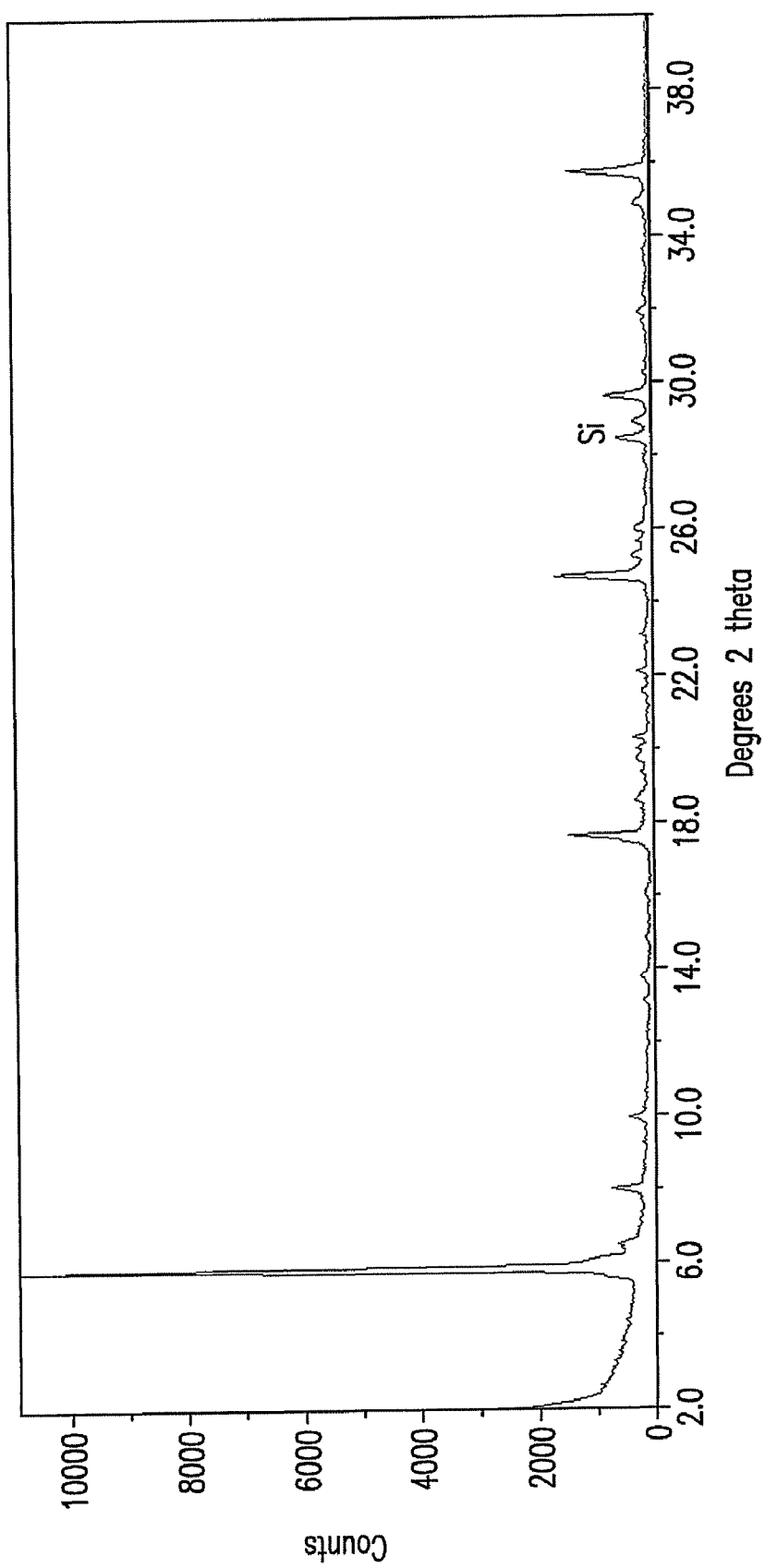
FIG. 4 provides a powder XRD pattern of crystalline Form III of Sitagliptin HCl.

In another embodiment, the invention provides a crystalline Sitagliptin hydrochloride, designated as Form III. Form III can be characterized by a powder XRD pattern with peaks at 5.8°, 17.6°, 24.7°, 29.6°, and 35.7°±0.2° 2θ; or by a powder XRD as shown in FIG. 4; or by combinations thereof.

Alternatively, Form III can be characterized by a powder XRD pattern with peaks at 5.8°, 8.0°, 9.9°, 17.6°, 24.7°, 25.2°, 28.9°, 29.6°, and 35.7°±0.2° 2θ. In addition, Sitagliptin hydrochloride Form III can be characterized by any combination of the above data.

Figure 5:
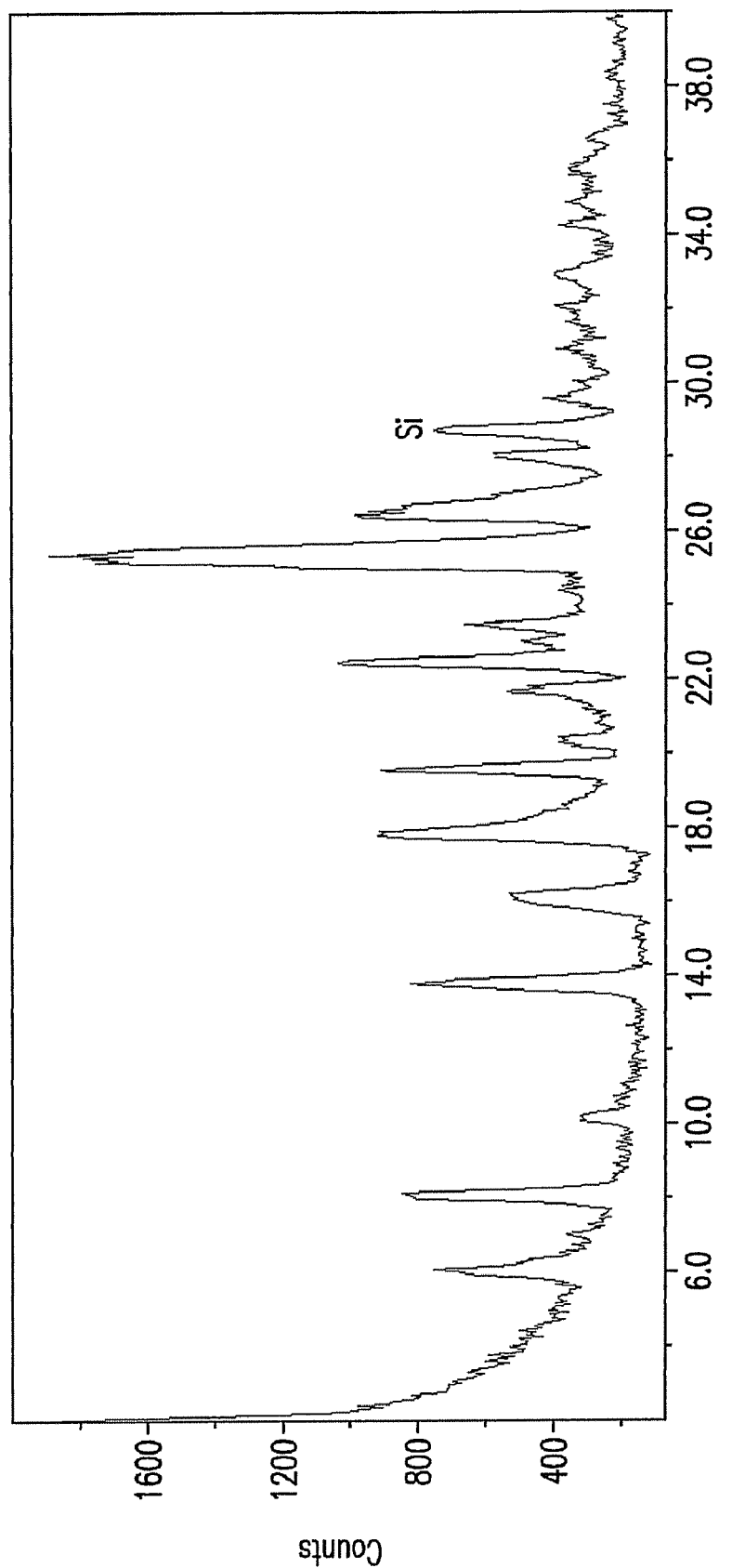
FIG. 5 provides a powder XRD pattern of crystalline Form IV of Sitagliptin HCl.

In another embodiment, the invention provides a crystalline Sitagliptin hydrochloride, designated as Form IV. Form IV can be characterized by a powder XRD pattern with peaks at 7.8°, 13.6°, 19.3°, 21.4°, and 22.2°±0.2° 2θ; or by a powder XRD as shown in FIG. 5; or by combinations thereof.

Alternatively, Form IV can be characterized by a powder XRD pattern with peaks at 5.9°, 7.8°, 13.6°, 15.8°, 17.6°, 19.3°, 21.4°, 22.2°, 24.9°, and 25.2°±0.2° 2θ. In addition, Sitagliptin hydrochloride Form IV can be characterized by any combination of the above data.

Figure 6:
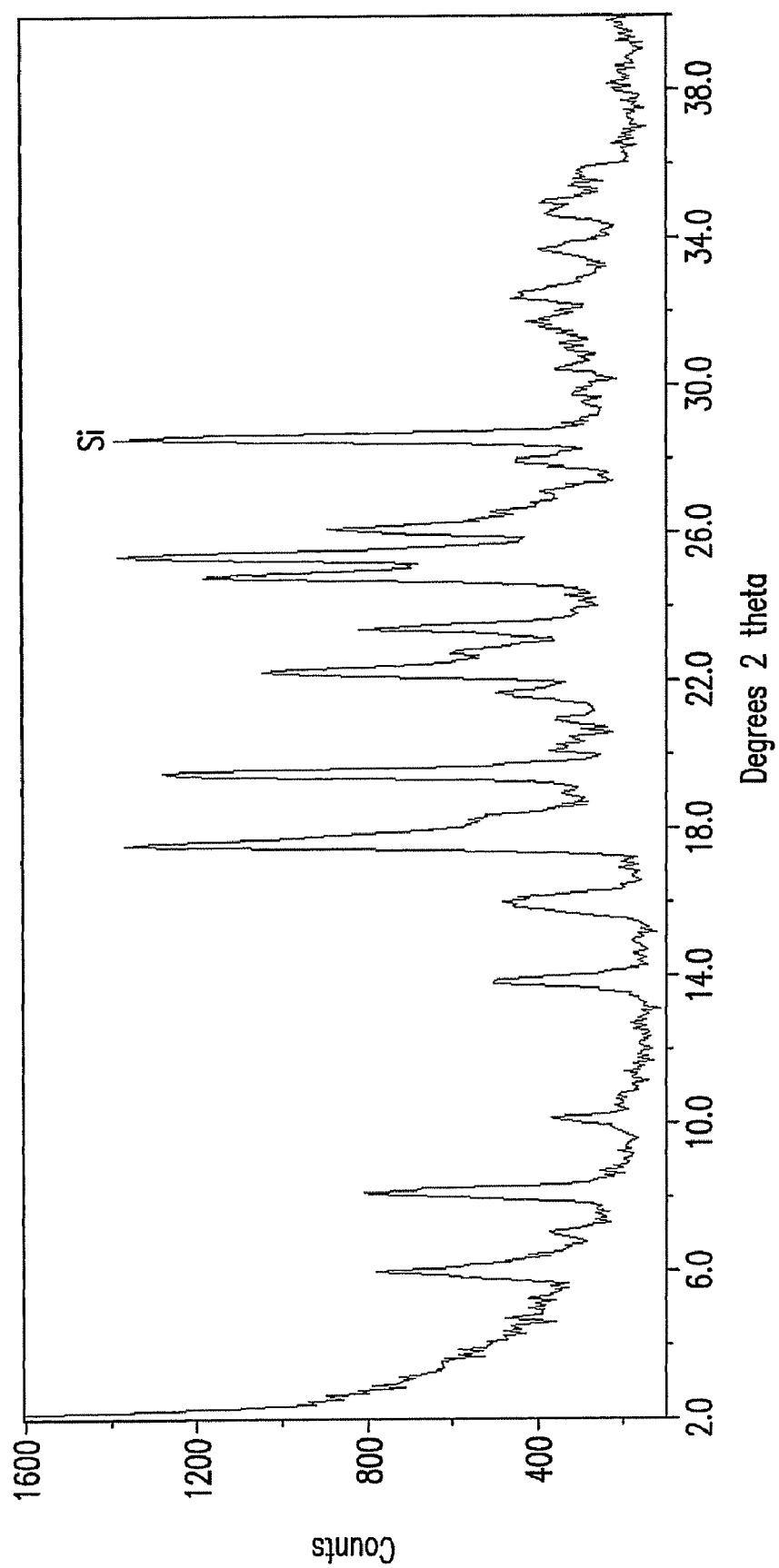
FIG. 6 provides a powder XRD pattern of crystalline Form V of Sitagliptin HCl.

In another embodiment, the invention provides a crystalline Sitagliptin hydrochloride, designated as Form V, characterized by a powder XRD pattern with peaks at 5.9°, 17.5°, 22.1°, 25.3°, and 26.0°±0.2° 2θ; or a powder XRD as shown in FIG. 6; or combinations thereof.

Alternatively, Form V can be characterized by a powder XRD pattern with peaks at 5.9°, 8.0°, 13.7°, 17.5°, 19.4°, 22.1°, 23.3°, 24.7°, and 25.3°±0.2° 2θ. In addition, Sitagliptin hydrochloride Form V can be characterized by any combination of the above data.

The above described crystalline forms of Sitagliptin salts can be used to prepare Sitagliptin phosphate, for example by reacting any of the above mentioned Sitagliptin salts with phosphoric acid. Alternatively, the above described forms of Sitagliptin salts can be used to prepare Sitagliptin phosphate by reacting any of the above mentioned Sitagliptin salt with a base to obtain free Sitagliptin free base, and to further react it with phosphoric acid.

The present invention further encompasses 1) a pharmaceutical composition comprising any one or combination of solid state Forms, as described above, and at least one pharmaceutically acceptable excipient and 2) the use of any one or combination of the above-described solid state Forms, in the manufacture of a pharmaceutical composition. The present invention also encompasses the use of any of the solid state forms described herein as a starting material or intermediate in the preparation of Sitagliptin phosphate. The pharmaceutical composition can be useful for the treatment of type 2 diabetes mellitus. Preferably, in the pharmaceutical compositions, the solid state forms contain 20% or less, for example 10% or less, or 5% or less, or 2% or less, or 1% or less of any other crystalline form of the respective Sitagliptin salt. The present invention also provides crystalline forms as described above for use as a medicament, preferably for the treatment of type 2 diabetes mellitus.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

X-Ray Power Diffraction:

Unless recited otherwise, X-Ray powder diffraction data was obtained by using methods known in the art using a SCINTAG powder X-Ray diffractometer model X'TRA equipped with a solid-state detector. Copper radiation of 1.5418 Å was used. A round sample holder with zero background was used. The scanning parameters included: range: 2-40 degrees two-theta; scan mode: continuous scan; step size: 0.05 deg.; and a rate of 3 degrees/minute.

Form S13 (FIG. 11) was analyzed on a Bruker X-Ray powder diffractometer model D8 advance equipped with lynxEye position sensitive detector at a CuKα radiation of 1.5418 Å. Scan range: 2-40°. Step size: 0.05°. Time per step: 26 seconds.

The peak positions are determined by using silicon powder as an internal standard in an admixture with the sample measured. The position of the silicon (111) peak was corrected to be 28.45 degrees two theta. The positions of the listed peaks were corrected respectively. (No correction was performed on the presented diffractograms in the Figure).

Solid State $^{13}$C NMR Spectra:

$^{13}$C NMR at 125 MHz using Bruker Avance II+500
SB probe using 4 mm rotors
Magic angle was set using KBr
Homogeneity of magnetic field checked using adamantane
Parameters for Cross polarization optimized using glycine
Spectral reference set according to glycine as external standard (176.03 ppm for low field carboxyl signal)
Scanning parameters:
Magic Angle Spinning Rate: 11 kHz
Pulse Program: cp with tppm 15 during decoupling
Delay time: for Sitagliptin sulfate: 5 s; for Sitagliptin acetate: 10 s.
Contact time: 2 ms
Number of Scans: 1024
For Sitagliptin acetate, the delay time was 10 s instead of 5 s.

EXAMPLES

Example A

Sitagliptin Base

Rhodium (I) chloride 1,5-cyclooctadiene complex (24.1 mg, 0.2%) and (R)-(−)-1-[(S)-2-diphenylphosphino)ferrocenyl]ethyl di-tert-butylphosphine (56.8 mg, 0.44%) were added to degassed methanol (20 mL). The resulting solution was stirred at 25° C., degassed again, and then stirred for one hour at 25° C. This catalyst solution was used in the hydrogenation described below.

(Z)-3-amino-1-(3-(trifluoromethyl)-5,6-dihydro-[1,2,4]triazolo[4,3-a]-pyrazyn-7(8H)-yl)-4-(2,4,5-trifluorophenyl)but-2-en-1-one (10 gr, 1 equivalent) and methanol (50 ml) were added to a 250 ml hydrogenation bottle at 25° C. and the bottle was subjected to vacuum and nitrogen backflush three times. The catalyst solution was added to the hydrogenation bottle and the bottle was again subjected to vacuum and nitrogen backflush three times and then to vacuum and backflush with hydrogen gas three times. The resulting reaction mixture was maintained under hydrogen at a pressure of 5 bar and heated to 55° C. The heated mixture was stirred at 5 bar pressure, at 55° C. for 3 days to obtain Sitagliptin base in methanol solution (optical purity by HPLC 97%, purity by HPLC 63.7%).

Example B

Sitagliptin L-Malate Form I1

STG base (5 g) was dissolved in acetonitrile (28.5 mL) at 25° C. (L)-Malic acid (1.65 g, 1 eq) was then added and the resulting mixture was heated to 50° C. After stirring at 50° C. for 3 hours it was cooled gradually to 25° C. and stirred overnight. The mixture formed was very viscous. It was cooled in an ice bath for 1 hour and then heated back to 25° C. N-Heptane (7 mL) was added and the resulting mixture was stirred at 25° C. for 2 hours. The product was isolated by vacuum filtration and dried at 40° C. overnight to obtain STG (L)-malate crystalline form I1 (3.01 g).

Example C

Sitagliptin Sulfate Form S2

STG base (350 mg) was dissolved in acetonitrile (2 mL) at 25° C. Sulfuric acid (95.6%, 24 µL, 0.5 eq) was then added and the mixture was heated to 50° C., stirred at 50° C. for 2 hours, then cooled gradually to 25° C. and stirred at 25° C. over a weekend. The product was isolated by vacuum filtration and dried at 40° C. for 16 hours to obtain STG sulfate crystalline form S2.

Example D

Sitagliptin Sulfate Form S6

STG base (5 g) was dissolved in ethyl acetate (65 mL) at 25° C., heated to 40° C. to dissolution, and then cooled to 25° C. Sulfuric acid (95.6%, 0.34 mL, 0.5 eq) was then added and the resulting mixture was heated to 50° C., stirred at 50° C. for 3 hours, and then cooled gradually to 25° C. and stirred at 25° C. for 1.5 hours. The product was isolated by vacuum filtration and dried at 40° C. overnight to obtain STG sulfate form S6 (5.23 g, 85% yield).

Example E

Sitagliptin Acetate Form E1

STG base (350 mg) was partially dissolved in ethyl acetate (3.5 mL) at 25° C. Acetic acid (50 µL, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to obtain STG acetate crystalline form E1.

Example F

Sitagliptin Sulfate Form S7

STG base (5 g) was added into isopropanol (IPA) (85 ml). The obtained mixture was heated to dissolution. The solution was cooled to room temperature and sulfuric acid 96.5% (0.6 gr, 0.5 eq) was added, and then the slurry was stirred for 4 hours. The product was isolated by vacuum filtration; the cake was washed with hexane (10 ml), and dried at 40° C. in a vacuum oven overnight to obtain Form S7 as shown in FIG. 1g; 5.76 gr (93% yield).

Example G

Amorphous Sitagliptin HCl

Sitagliptin base (8 g) was dissolved in methanol (50 ml) at about 25° C. A solution of HCl in methanol (13%, 8.27 ml) was added and the solution was stirred for 2 hours at about 25° C. Then the solvent was evaporated to obtain 9 g of Sitagliptin hydrochloride salt. The salt was dried in a vacuum oven at 20° C. for 24 hours to obtain amorphous Sitagliptin hydrochloride salt (8.3 g).

Example H

Sitagliptin Base

Sitagliptin phosphate (80 g) was mixed with water (720 ml) and MTBE (240 ml) and cooled to 0° C. The mixture was basified with 33% KOH solution to pH 11, and the mixture was then warmed to 20° C. The phases were separated and the aqueous phase was extracted with MTBE (120 ml×2). This procedure was performed on an additional Sitagliptin phosphate batch (80 g). The combined organic layers were stirred 18 hours at −15° C. A white slurry mixture was obtained. The product was isolated by vacuum filtration, washed with MTBE (500 ml) and dried in a vacuum oven at 40° C. for 3 days to obtain Sitagliptin base (110.19 g, 85% yield).

Example 1

Sitagliptin L-Malate Form I2

About 100 mg of Sitagliptin L-malate form I1 was put in an open yellow plastic cap, and kept at 100% relative humidity (RH) and room temperature for 6 days. It was then analyzed by powder XRD, and found to have transformed into form I2.

X-Ray powder diffraction data was obtained using a SCINTAG powder X-Ray diffractometer model X'TRA equipped with a solid-state detector. Copper radiation of 1.5418 Å was used. A round sample holder with zero background was used. The scanning parameters included: range: 2-40 degrees two-theta; scan mode: continuous scan; step size: 0.05 deg.; and a rate of 3 degrees/minute. All peak positions are within ±0.2 degrees two theta.

Example 2

Sitagliptin Sulfate Form S9

About 150 mg of Sitagliptin sulfate form S2 was put in an open Petri dish, and kept at 100±5% RH and room temperature for 12 days. It was then analyzed by powder XRD, and found to have transformed into form S9.

For the XRD measurement, the sample was mixed with a small amount of Si powder, and applied directly on a silicon plate holder. The X-ray powder diffraction pattern was measured with a Philips X'Pert PRO X-ray powder diffractometer, equipped with Cu irradiation source=1.54060 Å (Angstrom), X'Celerator (2.022° 2Q) detector. Scanning parameters: angle range: 3-40 deg., step size 0.0167, time per step 39 s, continuous scan.

Example 3

Sitagliptin Sulfate Form S9

About 150 mg of Sitagliptin sulfate form S6 was put in an open Petri dish, and kept at 100±5% RH and room temperature for 12 days. It was then analyzed by powder XRD, and found to have transformed into form S9.

For the XRD measurement, the sample was mixed with a small amount of Si powder, and applied directly on a silicon plate holder. The X-ray powder diffraction pattern was measured with a Philips X'Pert PRO X-ray powder diffractometer, equipped with Cu irradiation source=1.54060 Å (Angstrom), X'Celerator (2.022° 2Q) detector. Scanning parameters: angle range: 3-40 deg., step size 0.0167, time per step: 39 s, continuous scan.

Example 4

Sitagliptin Acetate, Form E2

Figure 3:
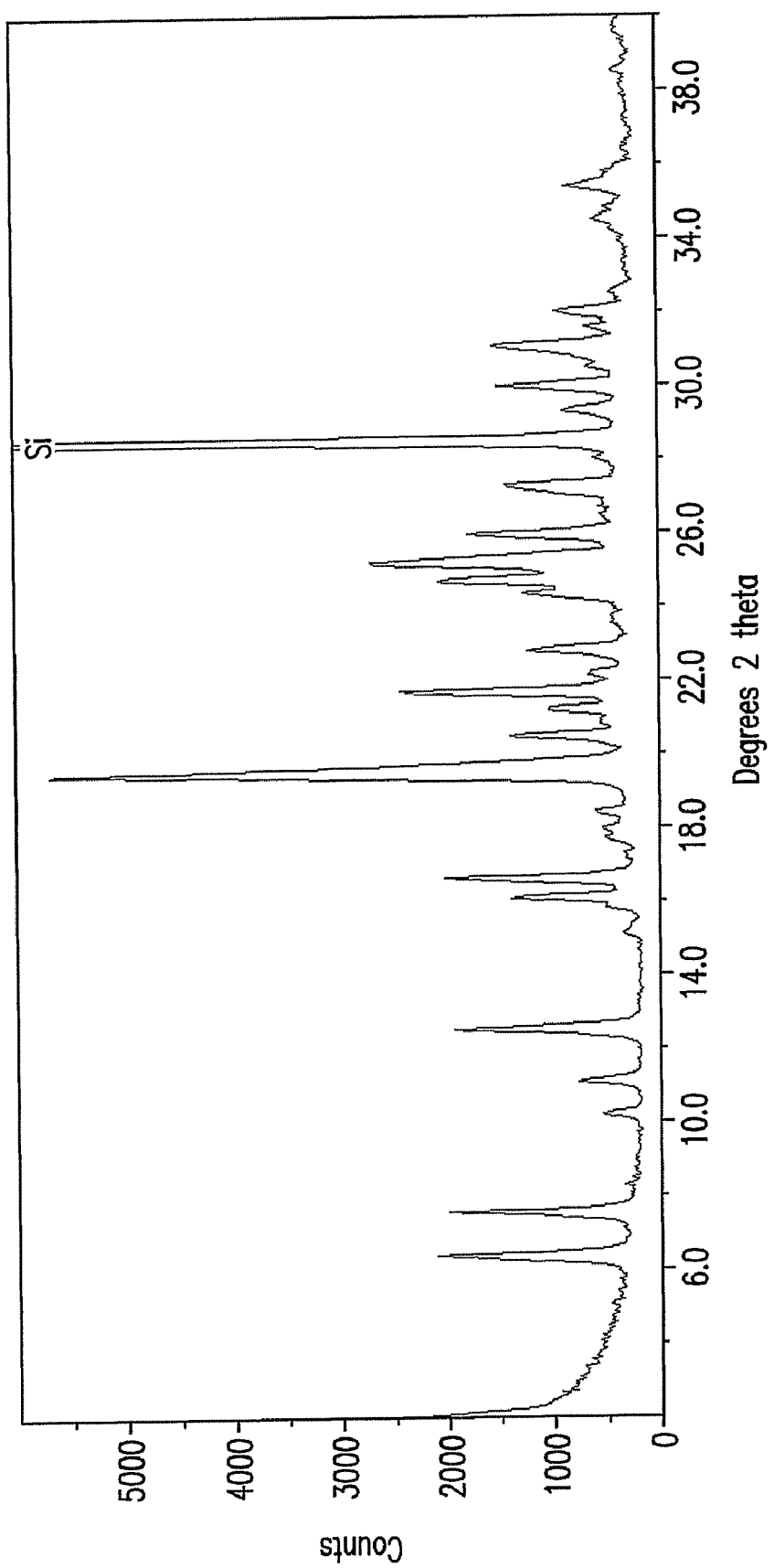
FIG. 3 provides a powder XRD pattern of crystalline Form E2 of Sitagliptin acetate.

About 0.4 g of Sitagliptin acetate form E1 was milled in a Ball-Mill instrument, Retch model-MM400. The experimental conditions were as follows: Frequency (1/s): 15; Time (minutes): 5. After the milling was finished, the sample was analyzed by XRD, and found to have transformed into form E2 of Sitagliptin acetate, as shown in FIG. 3.

Example 5

Crystalline Sitagliptin HCl Monohydrate Form III

STG base (5 g) was dissolved in IPA (50 mL) at 25° C., heated to 65° C. to dissolution, and then cooled to room temperature. HCl (1.5 mL) was then added dropwise over a period of 10 minutes. IPA (25 mL) was then added, and the resulting mixture was stirred for 45 minutes. The product precipitated, and was isolated by vacuum filtration to obtain form III of Sitagliptin HCl. The filtered product was then dried at 40° C. overnight to obtain crystalline STG-HCl monohydrate (5.3 g, 97% yield)

Example 6

Sitagliptin HCl, Form IV

About 200 mg of amorphous Sitagliptin HCl were stored in a glass vial under ethanol vapors for 7 days at room temperature. The sample was then analyzed in XRD, and found to have transformed into form IV of Sitagliptin HCl.

Example 7

Sitagliptin HCl, Form V

About 200 mg of amorphous Sitagliptin HCl were stored in a glass vial under isopropanol vapors for 7 days at RT. The sample was then analyzed in XRD, and found to have transformed into form V of Sitagliptin HCl.

Example 8

Sitagliptin Sulfate Form S10

To STG base (25 g), IPA (350 ml) was added, and the mixture was heated to 40° C. until dissolution, and then cooled to room temperature. A solution of $H_2SO_4$ (96.5%, 1.725 ml, 0.5 eq) in IPA (5 ml) was added dropwise. The resulting reaction mixture was stirred at room temperature overnight. A very dense (gel-like) slurry was formed. IPA (180 ml) was added to the slurry, and the product was isolated by vacuum filtration (slow filtration), dried at 40° C. under vacuum for 24 hours to obtain 19 g (67.8% yield) of Sitagliptin sulfate form S10.

Example 9

Sitagliptin Sulfate Form S7

STG base (5 g) was added to IPA (70 ml), and the resulting mixture was heated to 40° C. to dissolution, and then cooled to room temperature. A solution of $H_2SO_4$ (96.5%, 0.345 ml, 0.5 eq) in IPA (2 ml) and water (0.33 ml) was added dropwise to the cooled solution. During the addition a precipitate formed. The mixture was stirred for 4 days at room temperature. A very dense slurry was obtained. IPA (24 ml) was added to the slurry, and the product was isolated by vacuum filtration (slow filtration), dried at 40° C. in vacuum for 24 hours to obtain 4.74 g (84.6% yield) of Sitagliptin sulfate form S7.

Example 10

Sitagliptin Sulfate Form S12

A solution of $H_2SO_4$ (96.5%, 0.345 ml, 0.5 eq) in water (5 ml) was added to a mixture of STG base (5 g) in water (5 ml). After 30 minutes dissolution was obtained. The solution was stirred at room temperature for 5 days. The product precipitated, and was isolated by vacuum filtration to obtain form S11 of Sitagliptin sulfate. The product was then dried at 40° C. in vacuum for 24 hours to obtain 1.18 g (21% yield) of Sitagliptin sulfate form S12.

Example 11

Sitagliptin Sulfate Crystalline Form S13 and Form S14

STG base (5 g) was dissolved in methanol (25 mL) at 25° C. Sulfuric acid (66%, 0.5 eq, 0.5 mL) was added, and the resulting mixture was stirred for 4 hours at 25° C. The mixture was then seeded with STG-sulfate (crystalline form S10), and the resulting mixture was stirred overnight; and then cooled to 0° C., and stirred for an additional 3 hours at 0° C. The product that had precipitated was then isolated by vacuum filtration (crystalline form S13 was obtained), and dried in a vacuum oven at 40° C. overnight to obtain STG-sulfate crystalline form S14 (4.22 g, 75% yield).

Example 12

Sitagliptin Sulfate Crystalline Form S16

STG base (5 g) was dissolved in methanol (25 mL) at 25° C. Sulfuric acid (66%, 0.5 eq, 0.5 mL) was added, and the resulting mixture stirred for 4 hours at 25° C. MTBE (10 mL) was added, and the resulting mixture was stirred overnight at 25° C. No precipitation occurred; therefore the solution was cooled by ice bath. No precipitation occurred, therefore MTBE (10 mL) was added, white precipitation was obtained, and the mixture was stirred at 25° C. overnight. The product precipitated, was isolated by vacuum filtration, and dried in a vacuum oven at 40° C. overnight to obtain STG-sulfate crystalline form S16 (4.64 g, 83% yield).

Example 13

Sitagliptin Acetate Form E2

Sitagliptin acetate form E1 (400 mg) stored under IPA vapors at room temperature for 7 days. XRD analysis was preformed, and form E2 was obtained, as shown in FIG. 16.

Example 14

Sitagliptin Acetate Forms E3 and E4

STG base (20 g) was dissolved in ethyl acetate (200 mL) at 40° C., and cooled to 0° C. Acetic acid (2.95 g) was added, the mixture was stirred at 0° C. for about 20 hours, and precipitation occurred after one hour. The product was isolated by vacuum filtration (at 0-3° C.), and washed with EtOAc (190 ml) to obtain crystalline form E3. The thus formed form E3 was then dried at 40° C. 24 hours to obtain STG-acetate crystalline form E4 (13.6 g, 59% yield).

Example 15

Sitagliptin Sulfate Forms S13 and S14

STG base (5 g) was dissolved in methanol (25 mL) at 25° C. Sulfuric acid (66%, 0.5 eq, 0.5 mL) was added, and the mixture was stirred for 4 hours. STG-sulfate (crystalline form S14) was seeded, and a thick slurry was obtained. MeOH (8 ml) was added, and the mixture was stirred overnight. The mixture was then cooled to 0° C., and stirred for one hour. The product was isolated by vacuum filtration, and washed with cold MeOH (4 ml) to obtain crystalline form S13. The crystalline form S13 was then dried in a vacuum oven at 40° C. for 24 hours to obtain STG-sulfate crystalline form S14—(4.6 g, 83% yield).

Example 16

Sitagliptin Sulfate Forms S13 and S14

STG base (5 g) was dissolved in methanol (25 mL) at 25° C. Sulfuric acid (66%, 0.5 eq, 0.5 mL) was added, after 30 minutes the mixture became a slurry. The mixture was stirred overnight. The mixture was then cooled to 0° C., and stirred for one hour. The product was isolated by vacuum filtration, and washed with cold MeOH (6 ml) to obtain crystalline form S13. The thus formed form S13 was then dried in a vacuum oven at 40° C. for 24 hours to obtain STG-sulfate crystalline form S14 (4.49 gr, 81% yield).

Example 17

Sitagliptin Sulfate Forms S17 and S14

STG base (19.21 g) was dissolved in methanol (96 mL) at 25° C. Sulfuric acid (66%, 0.48 eq, 2.15 mL) was added dropwise, and the resulting mixture was stirred for 1.5 hours. The mixture was then seeded with STG-sulfate (crystalline form S14) and a thick slurry was obtained. The slurry was stirred overnight. The mixture was then cooled to 0° C., and stirred for 1.5 hours. The product was isolated by vacuum filtration, washed with MeOH (10 ml) to obtain crystalline form S16, and dried in vacuum oven at 40° C. overnight to obtain STG-sulfate crystalline form S17 (11.93 g, 56% yield). After additional drying at 50° C. for 24 hours STG-sulfate crystalline form S14 was obtained.

Example 18

Sitagliptin Sulfate Form S18 and Form S14

STG base (4 g) was dissolved in methanol (20 mL) at 25° C. Sulfuric acid (95.1%, 0.22 ml, 0.4 eq) was then added, and the mixture was stirred for 10 minutes and seeded with STG sulfate (Form S14). The mixture was stirred at 25° C. overnight. The product was isolated by vacuum filtration to obtain wet STG sulfate crystalline form S18, which was dried in a vacuum oven at 40° C. overnight to obtain Sitagliptin sulfate Form S14 (60% yield).

Example 19

Sitagliptin Sulfate Form S13 and S14

STG base (4 g) was dissolved in MeOH (20 mL) at 25° C. Sulfuric acid (95.1%, 0.248 ml, 0.45 eq) was then added. The mixture was stirred for 10 minutes and seeded with STG sulfate (Form S14). The mixture was stirred at 25° C. overnight. The product was isolated by vacuum filtration to obtain wet STG sulfate crystalline form S13, which was dried in a vacuum oven at 40° C. for 24 hours to obtain Sitagliptin sulfate Form S14 (66% yield).

Example 20

Sitagliptin Sulfate Form S1

About 150 mg of Sitagliptin sulfate form S14 was stored under 80% RH at 25° C. for 7 days. The sample was then tested by XRPD and determined to be crystal form Si of Sitagliptin sulfate.

Example 21

Sitagliptin Sulfate Forms S1 and S11

About 150 mg of Sitagliptin sulfate form S14 was stored under 100% RH at 25° C. for 7 days. The sample was then tested by XRPD and the crystal form was a polymorphic mixture of form S1 and form S11 of Sitagliptin sulfate.

Example 22

Sitagliptin Sulfate Forms S11 and S3

About 700 mg of Sitagliptin sulfate form S14 was ball-milled with 5 drops of water. Ball-mill conditions: Frequency-15 Hz, Time-5 minutes. The sample was then tested by XRPD and determined to be crystal form S11.

The sample was then dried in a vacuum oven at 40° C. overnight. The sample was then tested by XRPD and determined to be crystal form S3 of Sitagliptin sulfate.

Example 23

Mixture of Sitagliptin Sulfate Forms S13, S16, and S18

About 700 mg of Sitagliptin sulfate form S14 was ball-milled with 5 drops of methanol. Ball-mill conditions: Frequency-15 Hz, Time-5 minutes. The sample was then tested by XRPD and determined to be a polymorphic mixture of forms S13, S16, and S18 of Sitagliptin sulfate.

Example 24

Sitagliptin Sulfate Form S18

About 700 mg of Sitagliptin sulfate form S14 was ball-milled with 5 drops of ethanol. The conditions were: Frequency-15 Hz, Time-5 minutes. The sample was then tested by XRPD and determined to be crystal form S18 of Sitagliptin sulfate.

Example 25

Sitagliptin Sulfate Form S1

About 150 mg of Sitagliptin sulfate form S14 was stored under 70% RH at 25° C. for 7 days. The sample was then tested by XRPD and determined to be crystal form S1 of Sitagliptin sulfate.

Example 26

Sitagliptin Sulfate Form S1

About 150 mg of Sitagliptin sulfate form S14 was stored under 60% RH at 40° C. for 3 days. The sample was then tested by XRPD and determined to be crystal form S1 of Sitagliptin sulfate.

Example 27

Sitagliptin Sulfate Form S9

Figure 27:
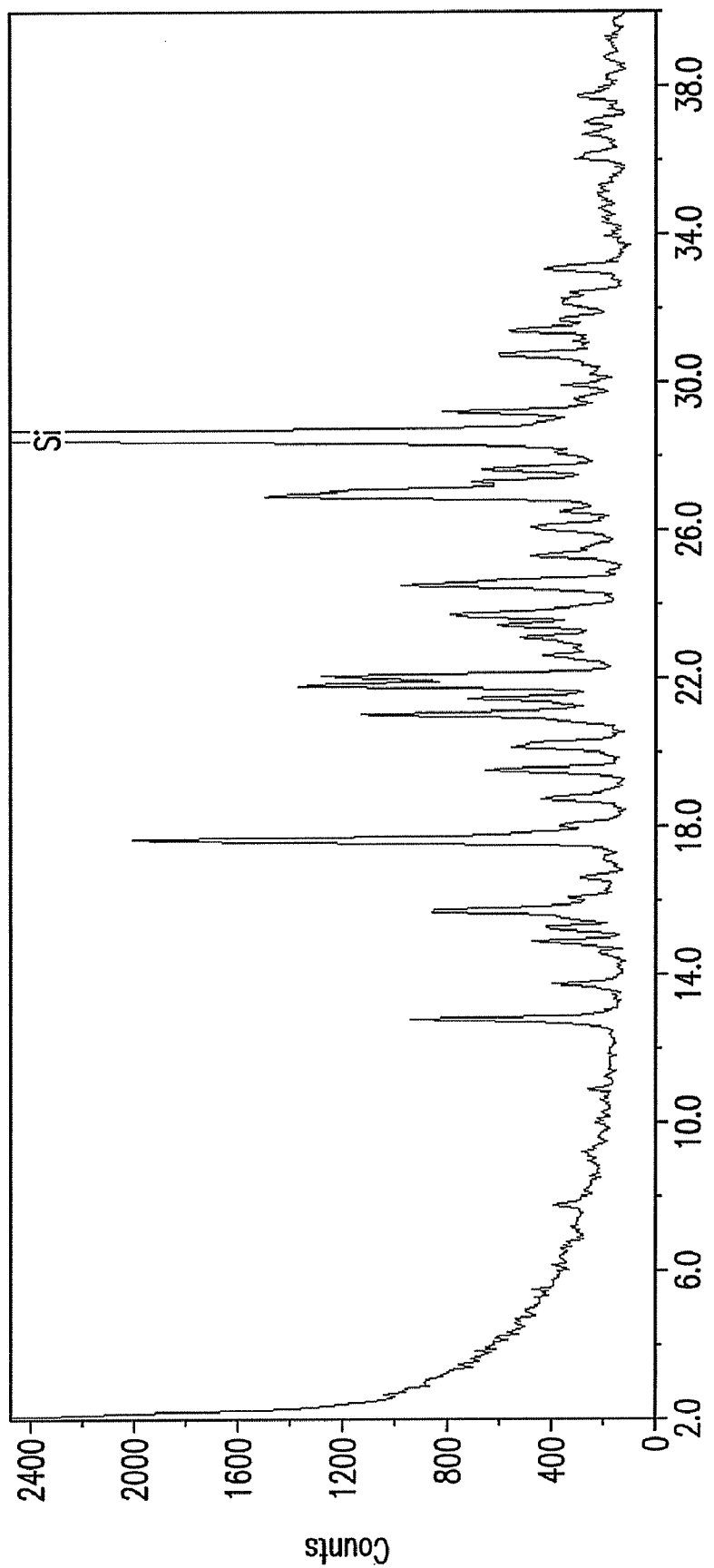
FIG. 27 provides a powder XRD pattern of crystalline Form S9 of Sitagliptin sulfate.
Figure 28:
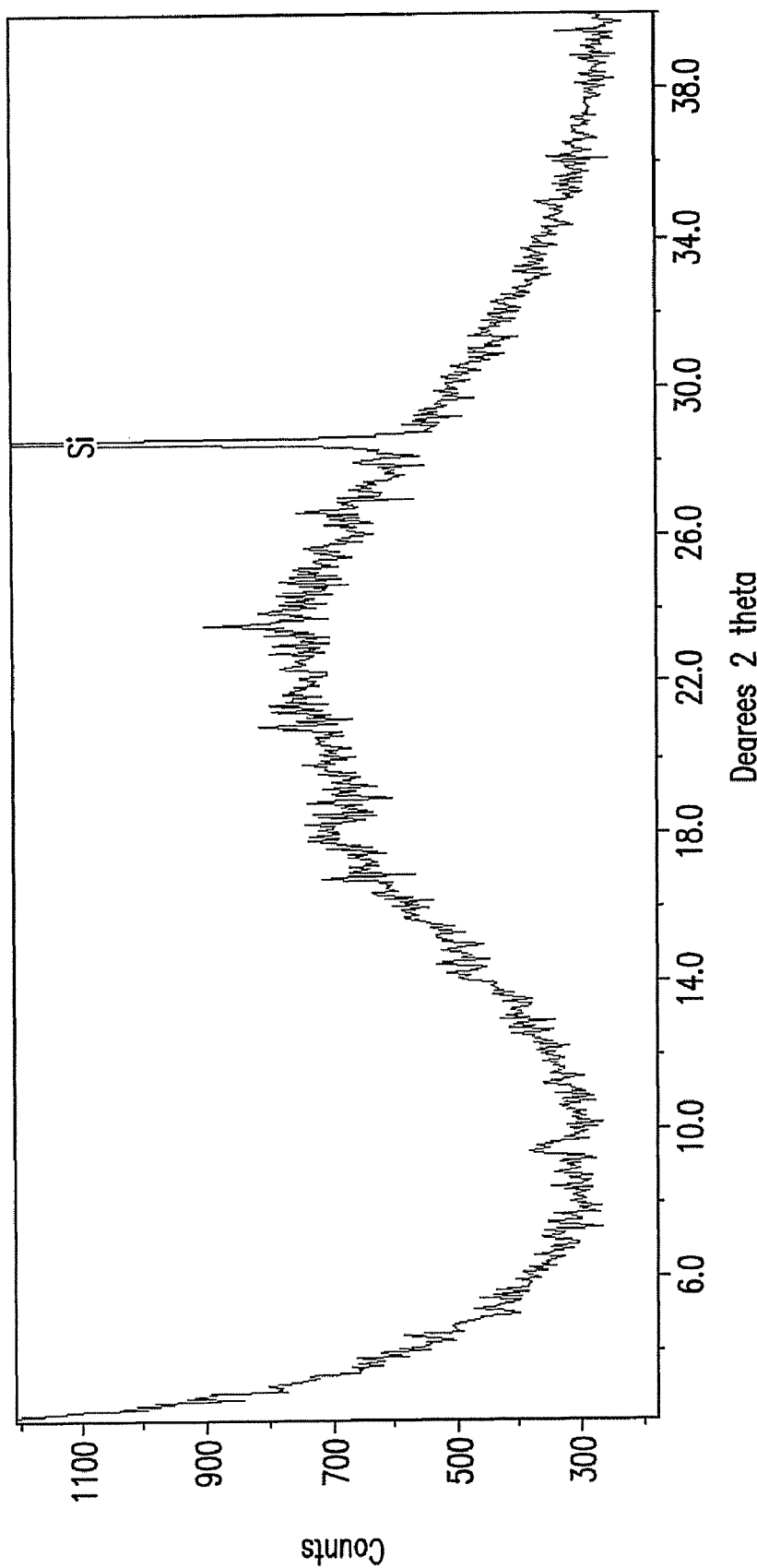
FIG. 28 provides a powder XRD pattern of amorphous Sitagliptin sulfate.

STG sulfate (2.5 gr) was dissolved in water (3.75 ml) and stirred at room temperature for 14 hours. Then, isopropanol (10 ml) was added. After 15 minutes, a solution was obtained and the solution was stirred at room temperature for 14 hours. The reaction mixture was cooled to 4° C. (with ice/water bath) for 2 hours. The product was isolated by vacuum filtration. The flask+cake were washed with cold isopropanol (15 ml). The product was dried at 40° C. under vacuum for 24 hours to obtain 1.86 g (74.4% yield) of STG sulfate form S9 as shown in FIG. 27.

Example 28

Mixture of Sitagliptin Sulfate Form S9 and Amorphous Sitagliptin Sulfate

STG sulfate Form S14 (1 g) and water were combined (1.5 ml, 1.5 Vol). The resulting slurry was stirred overnight at room temperature. Acetone was added (4 ml, 4 Vol) and a clear solution was observed. The solution was stirred at room temperature overnight. The solution was kept at 4° C. for 24 hours and a solid precipitated. The solid was filtered to give amorphous Sitagliptin sulfate. The product was dried in a vacuum oven at 40° C. for 16 hours to give 0.8 g of a mixture of Sitagliptin sulfate crystalline form S9 and amorphous Sitagliptin sulfate.

Example 29

Sitagliptin L-Malate Form I3

To a 250 ml round bottom flask, equipped with a magnetic stirrer and a reflux condenser, was added Sitagliptin base (12.0 g) and ethyl acetate (120 ml). The mixture was heated to 60° C. for dissolution. A solution of L-malic acid (3.95 g) in absolute ethanol (24 ml) was added to the above solution dropwise over 15 minutes. During the addition, the heating was stopped and the mixture was cooled slowly. When the addition was completed the temperature in the oil bath was 43° C. The solution was cooled to room temperature (~20° C.) and stirred overnight. After 3 days about 60 g of solvents were distilled out and the solution was stirred at room temperature over 10 days, during this time precipitation as a soft white block occurred. Ethyl acetate (110 ml) was added in order to facilitate filtration and the mixture was stirred for several minutes. The product was isolated by vacuum filtration, washed with ethyl acetate (40 ml) and dried in a vacuum oven at 50° C. for 24 hours and then for additional 48 hours at room temperature (15-25° C.) to obtain Sitagliptin L-malate crystalline form I3 (13.86 g, 87% yield).

Example 30

Sitagliptin L-Malate Form I4

A 250 mL round flask was charged with Sitagliptin free base (5 g, 12 mmol) and a mixture of ethyl acetate:ethanol (5:0.8 v/v, 25 mL) was added. The mixture was mechanically stirred and heated to 60° C. until complete dissolution. The solution was then cooled to room temperature. In parallel, L-malic acid (1.65 g, 12 mmol) was completely dissolved in a mixture of ethyl acetate:ethanol (5:0.8 v/v, 10 mL) at 60° C. and then cooled to room temperature. The solution of the L-malic acid was then added dropwise to the solution of Sitagliptin free base over a period of 10 minutes while stirring at room temperature with the rotation speed of 310 rpm. The obtained white gel-paste reaction mixture was stirred at room temperature for about 69 hours. The obtained massive white precipitate was isolated by vacuum filtration, washed with cold mixture of ethyl acetate:ethanol (5:0.8 v/v, 2×10 mL) and dried in a vacuum oven at 40° C. for 23 hours to give Sitagliptin L-malate (5.99 g, 92% w/w yield).

Example 31

Sitagliptin L-Malate Form I5

A 100 mL reactor was charged with Sitagliptin free base (10 g, 25 mmol) and a mixture of ethyl acetate:ethanol (5:1 v/v, 50 mL). The mixture was heated to 60° C. until complete dissolution and then cooled to room temperature. In parallel, L-malic acid (3.3 g, 25 mmol) was completely dissolved in a mixture of ethyl acetate:ethanol (5:1 v/v, 20 mL) at 60° C. and then cooled to room temperature. The solution of the L-malic acid was then added dropwise to the solution of Sitagliptin free base over a period of 15 minutes while stirring at room temperature with the rotation speed of 320 rpm. The mixture was seeded with Sitagliptin L-malate (crystalline form II) followed by cooling to −10° C. over a period of 6 h. The stirring at −10° C. was discontinued after 49.5 h and then warmed to 25° C. since no precipitation was observed. The mixture was stirred at 25° C. for about 44 h. The obtained massive white precipitate was isolated by vacuum filtration, washed with cold mixture of ethyl acetate:ethanol (5:1 v/v, 2×15 mL) and dried in a vacuum oven at 40° C. for 24 h to give Sitagliptin L-malate (9.46 g, 70% w/w yield.

Example 32

Stability Test of Sitagliptin Sulfate Form S14

A sample of form S14 was equilibrated in 0-100% relative humidity cells for 7 days at room temperature. The samples were analyzed by XRPD and TGA. Form S14 was found to be polymorphically stable up to 60% RH. The following table shows the results:

| % RH | % weight loss (TGA) | Form |
|---|---|---|
| Before the experiment | 3.4% | S14 |
| 0% | 2.3% | S14 |
| 20% | 2.0% | S14 |
| 40% | 1.9% | S14 |
| 60% | 2.4% | S14 |
| 80% | 4.4% | S1 |
| 100% | 8.9% | S11 + S1 |

According to the results, the equilibrium amount of water in form S14 is about 2%, corresponding to the theoretical value of 1.9% for monohydrate stoichiometry. However, form S14 is hygroscopic and can adopt higher amount of water before it transforms to the dehydrate form S1.

For TGA measurement METTLER TOLEDO TGA/DSC STARe System was used. 10-15 mg samples were placed into 150 μL alumina crucibles and scanned between 25-250° C. at 10°/minute heating rate under 40 ml/minute N2 flow rate.

For XRPD the ARL instrument was used.

Example 33

Stability Test of Sitagliptin Sulfate Form S16

A sample of form S16 was equilibrated in 0-100% relative humidity cells for 7 days at room temperature. The samples were analyzed by XRPD and TGA. Form S16 was found to be polymorphically stable up to 60% RH. The following table shows the results:

| % RH | % weight loss (TGA) | From !!!! form |
|---|---|---|
| Before the experiment | 3.0% | S16 |
| 0% | 2.9% | S16 |
| 20% | 2.9% | S16 |
| 40% | 2.9% | S16 |
| 60% | 2.9% | S16 |
| 80% | 4.4% | S1 |
| 100% | 8.9% | S9 + S1 |

According to the results, the equilibrium amount of water in form S16 is about 2.9%, corresponding to the theoretical value of 2.9% for sesquihydrate stoichiometry.

For TGA measurement METTLER TOLEDO TGA/DSC STARe System was used. 10-15 mg samples were placed into 150 μL alumina crucibles and scanned between 25-250° C. at 10°/minute heating rate under 40 ml/minute N2 flow rate.

For XRPD the ARL instrument was used.

Example 34

Stability Test of Sitagliptin Sulfate Form S19

A sample of Sitagliptin Sulfate form S16 was heated in TGA oven. Temperature range 25-180° C., heating rate 10° C./min, and sample size ~50 mg. The heating was performed in TGA/DSC 1 by METTLER TOLEDO.

Example 35

Sitagliptin Sulfate Form S14

Sitagliptin base (100 g) was dissolved in MeOH (500 ml) at room temperature.

Sulfuric acid (95.1% according to assay, 6.9 ml) was added dropwise. After seeding (half of a small spatula) the mixture was stirred at room temperature over a weekend.

The mixture was cooled to −5° C. for 3 hours. The Sitagliptin sulfate salt was isolated by vacuum filtration, washed with MeOH (60 ml) and dried in vacuum oven at 40° C. for 24 hours to obtain crystalline form S14 (74.33 g, 66.3% yield, total impurities—LT 0.03%, enantiomeric purity LT 0.03%).

Example 36

Sitagliptin L-Malate Form I1

A 1 L reactor was charged with Sitagliptin free base (70 g, 172 mmol), L-malic acid (23.1 g, 172 mmol) and a mixture of ethyl acetate:ethanol (5:1 v/v, 700 mL). The reaction mixture was heated to 40° C. until complete dissolution and then cooled to 25° C. over a period of 30 minutes with the rotation speed of 356 rpm. Seeding with Sitagliptin L-malate (crystalline form II) was performed followed by stirring at 25° C. over a period of 22.5 h. A massive white precipitate was obtained. The product was isolated by vacuum filtration, washed with cold mixture of ethyl acetate:ethanol (5:1 v/v, 1×70 mL) and dried in vacuum oven at 40° C. for 24 h to give Sitagliptin L-malate crystalline form II (89 g, 95.6% w/w yield).

Example 37

A sample of form I5 was equilibrated in humidity cells according to the condition detailed in the following table. Transformation to Sitagliptin L-malate Form II was observed by XRPD.

| RH | Temperate | Form |
|---|---|---|
| 60% | 40° C. | II |
| 100% | RT | II |

Example 38

A sample of form I5 was heated according to the condition detailed in the following table. Transformation to Sitagliptin L-malate Form II was observed by XRPD.

| TEMP. | TIME | RESULT |
|---|---|---|
| 130° C. by TGA | 10° C./min | II |

Example 39

A reactor of 1 L was charge with Sitagliptin free base (70 g, 172 mmol), L-malic acid (23.1 g, 172 mmol) and a mixture of ethyl acetate:ethanol (5:1 v/v, 700 mL). The reaction mixture was heated to 40° C. until complete dissolution and then cooled to 25° C. over a period of 30 minutes with the rotation speed of 356 rpm. Seeding with Sitagliptin L-malate (crystalline Sitagliptin L-malate Form II) was performed followed by stirring at 25° C. over a period of 21 h. A massive white precipitate was obtained. The product was isolated by vacuum filtration, washed with cold mixture of ethyl acetate:ethanol (5:1 v/v, 70 mL) and dried in vacuum oven at 40° C. for 23.5 h to give Sitagliptin L-malate form I5>II (88 g, 91.2% w/w yield). Re-drying in vacuum oven at 60° C. for 24 h produced pure Sitagliptin L-malate Form II.

Example 40

A 50 mL round flask was charge with Sitagliptin L-malate form I5>II (3 g, 5.44 mmol) and a mixture of ethyl acetate:ethanol (5:1 v/v, 30 mL). The obtained slurry was stirred at 50° C. over a period of 3.25 h and then cooled to room temperature. The slurry continued to stir at room temperature for additional 68 h. The product was isolated by vacuum filtration, washed with cold mixture of ethyl acetate:ethanol (5:1 v/v, 6 mL) and dried in vacuum oven at 40° C. for 24 h to give Sitagliptin L-malate Form II (2.83 g, 94.3% w/w yield).

Example 41

A 50 mL round flask was charge with Sitagliptin L-malate form I5>II (3 g, 5.44 mmol) and a mixture of ethyl acetate:ethanol (5:1 v/v, 30 mL). The obtained slurry was stirred at room temperature over a period of 71 h. The product was isolated by vacuum filtration, washed with cold mixture of ethyl acetate:ethanol (5:1 v/v, 7 mL) and dried in vacuum oven at 40° C. for 24 h to give Sitagliptin L-malate Form II (2.94 g, 98% w/w yield).

Example 42

A 50 mL round flask was charge with Sitagliptin sulfate form S7 (2 g, 96.4% assay) and methanol (10 mL). The obtained slurry was stirred at room temperature over a period of 22 h. The product was isolated by vacuum filtration, washed with the mother liquid and dried in vacuum oven at 40° C. for 24 h to give Sitagliptin sulfate crystalline form S14 (1.15 g).

Example 43

Sitagliptin free base (5 g, 12 mmol) and a mixture of methanol:water (95:5 v/v, 20 mL) were charged in a three neck round bottom flask and stirred at room temperature until complete dissolution. Sulfuric acid (95.1%, 0.35 mL) was added followed by seeding with crystalline Sitagliptin sulfate form S16 (0.05 g). The obtained turbid mixture was stirred at room temperature for about 20 hours. A portion of 4 mL of a mixture of methanol:water (95:5 v/v, 4 mL) was added and the stirring mixture was discontinued after additional 15 minutes. The product was isolated by vacuum, washed with a mixture of methanol:water (95:5 v/v, 4 mL) and dried in vacuum oven at 40° C. for 23.5 h to give Sitagliptin sulfate crystalline form S16 (3.79 g,).

Example 44

Sitagliptin free base (5 g, 12 mmol) and a mixture of methanol:water (95:5 v/v, 20 mL) were charged in a three neck round bottom flask and stirred at room temperature until complete dissolution. Sulfuric acid (95.1% according to assay, 0.35 mL) was added followed by seeding with crystalline Sitagliptin sulfate form S16 (0.05 g, 1% w/w). The obtained turbid mixture was stirred at room temperature for about 16 hours. Then, IPA (40 mL) was added drop-wise to the obtained massive white precipitate and the stirring at room temperature was discontinued after additional 5 h. The product was isolated by vacuum filtration, washed with cold IPA (10 mL) and dried in vacuum oven at 40° C. for 24 h to give Sitagliptin sulfate crystalline form S16 (5.16 g).

Example 45

Sitagliptin free base (5 g, 12 mmol) and methanol (20 mL) were charged in a three neck round bottom flask and stirred at room temperature until complete dissolution. Sulfuric acid (95.1% according to assay, 0.35 mL, 0.5 eq.) was added followed by seeding with crystalline Sitagliptin sulfate form S14 (0.05 g, 1% w/w). Methyl tert-butyl ether (30 mL) was added drop wise to the stirred solution over a period of 10 minutes. The obtained turbid mixture was stirred at room temperature for about 24 hours and produced massive white precipitate, which was isolated by vacuum filtration, washed with cold methyl tert-butyl ether (2×10 mL) and dried in vacuum oven at 40° C. for 22 h to give Sitagliptin sulfate crystalline form S20 (4.23 g, 76% w/w yield).

What is claimed:

1. Crystalline sitagliptin sulfate Form S9, characterized by data selected from: a powder XRD pattern with peaks at 12.7°, 15.7°, 17.7°, 21.0°, and 21.9°±0.2° 2θ; a powder XRD pattern as shown in FIG. 1; and any combination thereof.

2. Crystalline sitagliptin sulfate Form S11, characterized by data selected from: a powder XRD pattern with peaks at 3.9°, 7.9°, 11.8°, 16.4°, and 17.8°±0.2° 2θ; a powder XRD pattern as shown in FIG. 8; and any combination thereof.

3. Crystalline sitagliptin sulfate Form S13, characterized by data selected from: a powder XRD pattern with peaks at 5.6°, 8.5°, 16.6°, 17.4°, and 19.0°±0.2° 2θ; a powder XRD pattern as shown in FIG. 18; and any combination thereof.

4. Crystalline sitagliptin sulfate Form S14, characterized by data selected from: a powder XRD pattern with peaks at 9.1°, 10.3°, 18.6°, 21.6°, and 22.7°±0.2° 2θ; a powder XRD pattern as shown in FIG. 11; a solid-state $^{13}$C NMR spectrum with signals at 122.3, 151.2 and 170.2±0.2 ppm; a solid-state $^{13}$C NMR spectrum having chemical shift differences between the signal exhibiting the lowest chemical shift in the chemical shift range of 100 to 190 ppm and another in the chemical shift range of 100 to 190 ppm of 18.8, 47.7 and 66.7±0.1 ppm; a solid-state $^{13}$C NMR spectrum is depicted in FIG. 23 or 24; and any combination thereof.

5. Crystalline sitagliptin sulfate Form S16, characterized by data selected from: a powder XRD pattern with peaks at 9.2°, 16.3°, 18.5°, 20.6°, and 23.8°±0.2° 2θ; a powder XRD pattern as shown in FIG. 13; a solid-state $^{13}$C NMR spectrum with signals at 120.8, 150.0 and 171.1±0.2 ppm; a solid-state $^{13}$C NMR spectrum having chemical shift differences between the signal exhibiting the lowest chemical shift in the chemical shift range of 100 to 190 ppm and another signal in the chemical shift range of 100 to 190 ppm of 16.1, 45.3 and 66.4±0.1 ppm; a solid-state $^{13}$C NMR spectrum as depicted in FIG. 25 or 26; and any combination thereof.

6. Crystalline sitagliptin sulfate Form S14, characterized by data selected from: a powder XRD pattern with peaks at 9.1°, 10.3°, 18.6°, 21.6°, and 22.7°±0.2° 2θ; a powder XRD pattern as shown in FIG. 11; and any combination thereof.

7. Crystalline sitagliptin sulfate Form S14 of claim 6, further characterized by data selected from: a solid-state $^{13}$C NMR spectrum with signals at 122.3, 151.2 and 170.2±0.2 ppm; a solid-state $^{13}$C NMR spectrum having chemical shift differences between the signal exhibiting the lowest chemical shift in the chemical shift range of 100 to 190 ppm and another signal in the chemical shift range of 18.8, 47.7 and 66.7±0.1 ppm; a solid-state $^{13}$C NMR spectrum is depicted in FIG. 23 or 24; and any combination thereof.

8. Crystalline sitagliptin sulfate Form S16, characterized by data selected from: a powder XRD pattern with peaks at 9.2°, 16.3°, 18.5°, 20.6°, and 23.8°±0.2° 2θ; a powder XRD pattern as shown in FIG. 13; and any combination thereof.

9. Crystalline sitagliptin sulfate Form S16 of claim 8, further characterized by data selected from: a solid-state $^{13}$C NMR spectrum with signals at 120.8, 150.0 and 171.1±0.2 ppm; a solid-state $^{13}$C NMR spectrum having chemical shift differences between the signal exhibiting the lowest chemical shift in the chemical shift range of 100 to 190 ppm and another signal in the chemical shift range of 100 to 190 ppm of 16.1, 45.3 and 66.4±0.1 ppm; a solid-state $^{13}$C NMR spectrum as depicted in FIG. 25 or 26; and any combination thereof.

* * * * *